(12) United States Patent
Jeong et al.

(10) Patent No.: US 11,597,972 B2
(45) Date of Patent: Mar. 7, 2023

(54) METHOD OF ANALYZING MICROHAPLOTYPE USING NEXT GENERATION SEQUENCING

(71) Applicant: Republic of Korea (National Forensic Service Director Ministry of Interior and Safety), Wonju-si (KR)

(72) Inventors: Kyu Sik Jeong, Jeju-si (KR); Byung Won Chun, Busan (KR); Yang Han Lee, Wonju-si (KR); Ki Won Park, Paju-si (KR); Kyoung Jin Shin, Seoul (KR); Eun Young Lee, Seoul (KR); Bo Min Kim, Uiwang-si (KR)

(73) Assignee: REPUBLIC OF KOREA (NATIONAL FORENSIC SERVICE DIRECTOR MINISTRY OF INTERIOR AND SAFETY), Wonju-si (KR)

( * ) Notice: Subject to any disclaimer, the term of this patent is extended or adjusted under 35 U.S.C. 154(b) by 137 days.

(21) Appl. No.: 16/286,255

(22) Filed: Feb. 26, 2019

(65) Prior Publication Data
US 2019/0264266 A1    Aug. 29, 2019

(30) Foreign Application Priority Data
Feb. 27, 2018 (KR) .................. 10-2018-0023522

(51) Int. Cl.
*C12Q 1/6874* (2018.01)
*C12Q 1/6888* (2018.01)
*G16B 20/20* (2019.01)
*G16B 50/30* (2019.01)
*G16B 25/20* (2019.01)
*G16B 30/00* (2019.01)

(52) U.S. Cl.
CPC ......... *C12Q 1/6874* (2013.01); *C12Q 1/6888* (2013.01); *G16B 20/20* (2019.02); *G16B 25/20* (2019.02); *G16B 30/00* (2019.02); *G16B 50/30* (2019.02); *C12Q 2600/156* (2013.01); *C12Q 2600/16* (2013.01); *C12Q 2600/172* (2013.01)

(58) Field of Classification Search
CPC .............. C12Q 1/6874; C12Q 1/6888; C12Q 2600/156; C12Q 2600/172; C12Q 1/6827; C12Q 1/6869; C12Q 2537/143
See application file for complete search history.

(56) References Cited

FOREIGN PATENT DOCUMENTS

| KR | 10-1457983 B1 | 11/2014 |
|----|---------------|---------|
| KR | 10-1533792 B1 | 7/2015  |
| KR | 10-1667526 B1 | 10/2016 |

OTHER PUBLICATIONS

Shin, Kyoung-Jin. A pilot study of microhaplotype analysis for degraded DNA and mixed DNA using in-house next generation sequencing panels. Dec. 1, 2020. (Year: 2020).*
Lee et al. Sequence Variations of 51 Microhaplotypes in Koreans Detected by Massively Parallel Sequencing. 2017. (Year: 2017).*
Kidd et al. Forensic Science International. 2013. Genetic Supplement Series 4: e123-e124. (Year: 2013).*
Shin, Kyoung-Jin. Next Generation Sequencing of Microhaplotypes for Forensic DNA Typing. Nov. 1, 2017 (Year: 2017).*
Ge et al. In J Legal Med. 2010. 124:353-361. (Year: 2010).*
Kidd et al. Investigative Genetics. 2015. 6:1. (Year: 2015).*
Pang et al. Scientific Reports. 2020. 10:1945. (Year: 2020).*
Hui Wang et al., "NGS technology makes microhaplotype a potential forensic marker". Forensic Science International: Genetics Supplement Series, vol. 5, Available online Sep. 24, 2015, pp. e233-e234.
Kyung-Jin Shin, "Next Generation Sequencing of Microhaplotypes for Forensic DNA typing". Nov. 1, 2017, pp. 1-12, Dept. of Forensic Medicine Yonsei University College of Medicine Seoul, Republic of Korea.
So Yeun Kwon et al., "Investigation into the sequence structure of 23 Y chromosomal STR loci using massively parallel sequencing". Forensic Science International: Genetics, vol. 25, Available online Aug. 28, 2016, pp. 132-141.
Kenneth K. Kidd et al., "Evaluating 130 microhaplotypes across a global set of 83 populations". Forensic Science International: Genetics, vol. 29, Available online Mar. 16, 2017, pp. 29-37.
Kenneth K. Kidd et al., "Current sequencing technology makes microhaplotypes a powerful new type of genetic marker for forensics". Forensic Science International: Genetics, vol. 12, Available online Jun. 23, 2014, pp. 215-224.
Eun Hye Kim et al., "Sequence-based diversity of 23 autosomal STR loci in Koreans investigated using an in-house massively parallel sequencing panel". Forensic Science International: Genetics, vol. 30, Available online Jul. 9, 2017, pp. 134-140.

* cited by examiner

*Primary Examiner* — Joseph G. Dauner
(74) *Attorney, Agent, or Firm* — Novick, Kim & Lee PLLC; Jae Youn Kim

(57) ABSTRACT

Provided is a method of analyzing microhaplotypes by using a next generation sequencing (NGS). The method of analyzing microhaplotypes by using the NGS includes: (a) performing a multiplex PCR for simultaneously amplifying the microhaplotypes; (b) performing an indexing PCR by using a product of the multiplex PCR; and (c) performing the NGS by using a product of the indexing PCR.

3 Claims, 14 Drawing Sheets

Specification includes a Sequence Listing.

METHOD OF ANALYZING MICROHAPLOTYPE USING NEXT GENERATION SEQUENCING

CROSS-REFERENCE IN THE RELATED APPLICATIONS

This application claims priority to and benefit of Korean Patent Application No. 10-2018-0023522, filed Feb. 27, 2018, of which disclosure is incorporated herein by reference in its entirety.

INCORPORATION OF SEQUENCE LISTING

This application contains a sequence listing submitted in Computer Readable Form (CRF). The CFR file containing the sequence listing is entitled "8-PK0053032-SequenceListing.txt", which was created and modified on Feb. 26, 2019, and is 38,001 bytes in size. The information in the sequence listing is incorporated herein by reference in its entirety.

BACKGROUND OF THE INVENTION

1. Field of the Invention

The present invention relates to a method of analyzing microhaplotypes by using a next generation sequencing.

2. Description of the Related Art

Analyzing DNA extracted from a cell refers to comparing a specific gene site that is different from each person and called a DNA marker. The DNA marker typically includes a short tandem repeat (STR) having been used conventionally and a single nucleotide polymorphism (SNP) having been used widely and recently.

Each person has the different number of repeated specific sequences of DNA, in which the site is called the STR. The STR exists in a non-encrypted domain of human genome, in which the STR shows that the sequence of 2 bp to 7 bp is repeated. The SNP is a much shorter sequence than STR, in which every person has the same length of SNP and a different nucleotide order.

A capillary electrophoresis (CE) analysis is performed by irradiating an STR amplicon, which is PCR-amplified by using a primer to which fluorescence is attached, with laser. Although the size of a PCR product may be analyzed conveniently and quickly, the number of analyzable STRs is limited and a nucleotide sequence variation of STR cannot be checked.

As an approach to complement or replace the disadvantages of the CE analysis, there has also been an attempt to analyze the STR by using a next generation sequencing (NGS) technology in a forensic science field.

SUMMARY OF THE INVENTION

The discriminating power for a simple SNP composed of two alleles is generally lower than that of the STR. The conventional SNP analysis shows the low discriminating power when a degraded sample or a mixed sample is analyzed, and shows a limit to simultaneously estimate an identification and a biogeographic origin.

A microhaplotype refers to the presence of at least two bases, which are different in each person, within each base pair of 200 bp or less. Multiple alleles of the microhaplotype show the discriminating power higher than that of the simple SNP, and are expected to complement the limitations of the existing SNP analysis.

Because a multiplex PCR system capable of simultaneously analyzing major microhaplotypes is not developed, and a method of generating an NGS library is complicated, the simpler analyzing method performable in forensic science laboratories is required.

The present invention provides a method of simultaneously analyzing a plurality of microhaplotypes by using a next generation sequencing.

The present invention provides a method of analyzing microhaplotypes by using a next generation sequencing which is effective for analyzing a sample to which DNAs of different species are mixed.

The present invention provides a method of analyzing microhaplotypes by using a next generation sequencing which is effective for analyzing degraded DNA.

The method of analyzing microhaplotypes by using a next generation sequencing (NGS) according to the present invention includes the steps of: (a) performing a multiplex PCR for simultaneously amplifying the microhaplotypes; (b) performing an indexing PCR by using a product of the multiplex PCR; and (c) performing the next generation sequencing by using a product of the indexing PCR.

In step (a), a specific sequence of each microhaplotype may be amplified by using first primers complementarily binding to the microhaplotypes.

In step (b), a bar-coded NGS library may be generated by using second primers complementarily binding to the product of the multiplex PCR.

In step (a), the microhaplotypes may be simultaneously amplified to a size of 270 bp or less. Specifically, in step (a), the microhaplotypes may be simultaneously amplified to a size between 115 bp and 263 bp.

In step (c), the maximum NGS read counts obtained for each microhaplotype do not exceed two times the minimum NGS read counts.

The DNA sample may include a mixture of a first sample and a second sample, and the first sample and the second sample are obtained from objects which are different species from each other.

The DNA sample may include a degraded DNA sample. As a result of the NGS analysis, the read counts are shown at least 50% on average as compared to a non-degraded DNA sample.

The microhaplotypes may include at least two among COG2, ITGB6, D18S1122, GFI1B, D21S1263, D5S1970, LOC642852, COL4A1, IGSF21, RXRA, SGCG, LINC0111, LRRN2, CPNE4, GNGT2, COL4A3, SUDS3, D13S169, PLCG2, D22S1159, KIF16B, ADH7, C14ORF43, FAM99A, FRMD4A, OR52S1P, ARHGAP27, LRRC63, KLK5, USH2A, D13S1320, SEMA6D, MYO5C, TOM1L1, HERC1, DRD2NCAM, ELK2B, FRMD3, CEBPB, LINC01233, STATP1, RBFOX1-1, NELFA, ZC3H7B, EDAR, KANK1, RBFOX1, PFKP, LPPR1, CYYR1, HRH4, LOC28716, D125290, TENM4, CNTN5, and CEP104.

The first primer may include a primer 12 of SEQ ID NO: 1 and SEQ ID NO: 2 complementarily binding to a locus of the COG2, a primer 34 of SEQ ID NO: 3 and SEQ ID NO: 4 complementarily binding to a locus of the ITGB6, a primer 56 of SEQ ID NO: 5 and SEQ ID NO: 6 complementarily binding to a locus of the D18S1122, a primer 78 of SEQ ID NO: 7 and SEQ ID NO: 8 complementarily binding to a locus of the GFI1B, a primer 910 of SEQ ID NO: 9 and SEQ ID NO: 10 complementarily binding to a locus of the D21S1263, a primer 1112 of SEQ ID NO: 11 and SEQ ID NO: 12 complementarily binding to a locus of the D5S1970, a primer 1314 of SEQ ID NO: 13 and SEQ ID NO: 14 complementarily binding to a locus of the LOC642852, a primer 1516 of SEQ ID NO: 15 and SEQ ID NO: 16 complementarily binding to a locus of the COL4A1, a primer 1718 of SEQ ID NO: 17 and SEQ ID NO: 18 complementarily binding to a locus of the IGSF21, a primer 1920 of SEQ ID NO: 19 and SEQ ID NO: 20 complementarily binding to a locus of the RXRA, a primer 2122 of SEQ ID NO: 21 and SEQ ID NO: 22 complementarily binding to a genome locus of the SGCG, a primer 2324 of SEQ ID NO: 23 and SEQ ID NO: 24 complementarily binding to a locus of the LINC0111, a primer 2526 of SEQ ID NO: 25 and SEQ ID NO: 26 complementarily binding to a locus of the LRRN2, a primer 2728 of SEQ ID NO: 27 and SEQ ID NO: 28 complementarily binding to a locus of the CPNE4, a primer 2930 of SEQ ID NO: 29 and SEQ ID NO: 30 complementarily binding to a locus of the GNGT2, a primer 3132 of SEQ ID NO: 31 and SEQ ID NO: 32 complementarily binding to a locus of the COL4A3, a primer 3334 of SEQ ID NO: 33 and SEQ ID NO: 34 complementarily binding to a locus of the SUDS3, a primer 3536 of SEQ ID NO: 35 and SEQ ID NO: 36 complementarily binding to a locus of the D13S169, a primer 3738 of SEQ ID NO: 37 and SEQ ID NO: 38 complementarily binding to a locus of the PLCG2, a primer 3940 of SEQ ID NO: 39 and SEQ ID NO: 40 complementarily binding to a locus of the D22S1159, a primer 4142 of SEQ ID NO: 41 and SEQ ID NO: 42 complementarily binding to a locus of the KIF16B, a primer 4344 of SEQ ID NO: 43 and SEQ ID NO: 44 complementarily binding to a locus of the ADH7, a primer 4546 of SEQ ID NO: 45 and SEQ ID NO: 46 complementarily binding to a locus of the C14ORF43, a primer 4748 of SEQ ID NO: 47 and SEQ ID NO: 48 complementarily binding to a locus of the FAM99A, a primer 4950 of SEQ ID NO: 49 and SEQ ID NO: 50 complementarily binding to a locus of the FRMD4A, a primer 5152 of SEQ ID NO: 51 and SEQ ID NO: 52 complementarily binding to a locus of the OR52S1P, a primer 5354 of SEQ ID NO: 53 and SEQ ID NO: 54 complementarily binding to a locus of the ARHGAP27, a primer 5556 of SEQ ID NO: 55 and SEQ ID NO: 56 complementarily binding to a locus of the LRRC63, a primer 5758 of SEQ ID NO: 57 and SEQ ID NO: 58 complementarily binding to a locus of the KLK5, a primer 5960 of SEQ ID NO: 59 and SEQ ID NO: 60 complementarily binding to a locus of the USH2A, a primer 6162 of SEQ ID NO: 61 and SEQ ID NO: 62 complementarily binding to a locus of the D13S1320, a primer 6364 of SEQ ID NO: 63 and SEQ ID NO: 64 complementarily binding to a locus of the SEMA6D, a primer 6566 of SEQ ID NO: 65 and SEQ ID NO: 66 complementarily binding to a locus of the MYO5C, a primer 6768 of SEQ ID NO: 67 and SEQ ID NO: 68 complementarily binding to a locus of the TOM1L1, a primer 6970 of SEQ ID NO: 69 and SEQ ID NO: 70 complementarily binding to a locus of the HERC1, a primer 7172 of SEQ ID NO: 71 and SEQ ID NO: 72 complementarily binding to a locus of the DRD2NCAM, a primer 7374 of SEQ ID NO: 73 and SEQ ID NO: 74 complementarily binding to a locus of the ELK2B, a primer 7576 of SEQ ID NO: 75 and SEQ ID NO: 76 complementarily binding to a locus of the FRMD3, a primer 7778 of SEQ ID NO: 77 and SEQ ID NO: 78 complementarily binding to a locus of the CEBPB, a primer 7980 of SEQ ID NO: 79 and SEQ ID NO: 80 complementarily binding to a locus of the LINC01233, a primer 8182 of SEQ ID NO: 81 and SEQ ID NO: 82 complementarily binding to a locus of the STATP1, a primer 8384 of SEQ ID NO: 83 and SEQ ID NO: 84 complementarily binding to a locus of the RBFOX1-1, a primer 8586 of SEQ ID NO: 85 and SEQ ID NO: 86 complementarily binding to a locus of the NELFA, a primer 8788 of SEQ ID NO: 87 and SEQ ID NO: 88 complementarily binding to a locus of the ZC3H7B, a primer 8990 of SEQ ID NO: 89 and SEQ ID NO: 90 complementarily binding to a locus of the EDAR, a primer 9192 of SEQ ID NO: 91 and SEQ ID NO: 92 complementarily binding to a locus of the KANK1, a primer 9394 of SEQ ID NO: 93 and SEQ ID NO: 94 complementarily binding to a locus of the RBFOX1, a primer 9596 of SEQ ID NO: 95 and SEQ ID NO: 96 complementarily binding to a locus of the PFKP, a primer 9798 of SEQ ID NO: 97 and SEQ ID NO: 98 complementarily binding to a locus of the LPPR1, a primer 99100 of SEQ ID NO: 99 and SEQ ID NO: 100 complementarily binding to a locus of the CYYR1, a primer 101102 of SEQ ID NO: 101 and SEQ ID NO: 102 complementarily binding to a locus of the HRH4, a primer 103104 of SEQ ID NO: 103 and SEQ ID NO: 104 complementarily binding to a locus of the LOC28716, a primer 105106 of SEQ ID NO: 105 and SEQ ID NO: 106 complementarily binding to a locus of the D12S290, a primer 107108 of SEQ ID NO: 107 and SEQ ID NO: 108 complementarily binding to a locus of the TENM4, a primer 109110 of SEQ ID NO: 109 and SEQ ID NO: 110 complementarily binding to a locus of the CNTN5, and a primer 111112 of SEQ ID NO: 111 and SEQ ID NO: 112 complementarily binding to a locus of the CEP104.

The primer 12 may have a concentration of 0.18 μM to 0.38 μM, the primer 34 may have a concentration of 0.06 μM to 0.36 μM, the primer 56 may have a concentration of 0.08 μM to 0.28 μM, the primer 78 may have a concentration of 0.08 μM to 0.28 μM, the primer 910 may have a concentration of 0.24 μM to 0.55 μM, the primer 1112 may have a concentration of 0.90 μM to 1.10 μM, the primer 1314 may have a concentration of 0.22 μM to 0.42 μM, the primer 1516 may have a concentration of 0.15 μM to 0.35 μM, the primer 1718 may have a concentration of 0.30 μM to 0.50 μM, the primer 1920 may have a concentration of 0.15 μM to 0.35 μM, the primer 2122 may have a concentration of 0.40 μM to 0.60 μM, the primer 2324 may have a concentration of 0.30 μM to 0.60 μM, the primer 2526 may have a concentration of 0.15 μM to 0.35 μM, the primer 2728 may have a concentration of 1.90 μM to 2.10 μM, the primer 2930 may have a concentration of 0.14 μM to 0.34 μM, the primer 3132 may have a concentration of 0.27 μM to 0.47 μM, the primer 3334 may have a concentration of 0.19 μM to 0.39 μM, the primer 3536 may have a concentration of 0.45 μM to 0.65 μM, the primer 3738 may have a concentration of 0.18 μM to 0.38 μM, the primer 3940 may have a concentration of 0.08 μM to 0.28 μM, the primer 4142 may have a concentration of 0.19 μM to 0.39 μM, the primer 4344 may have a concentration of 0.26 μM to 0.46 μM, the primer 4546 may have a concentration of 0.28 μM to 0.48 μM, the primer 4748 may have a concentration of 0.50 μM to 0.70 μM, the primer 4950 may have a concentration of 0.21 μM to 0.41 μM, the primer 5152 may have a concentration of 1.30 μM to 1.50 μM, the primer 5354 may have a concentration of 0.40 μM to 0.60 μM, the primer 5556 may have a concentration of 0.45 μM to 0.65 μM, the primer 5758 may have a concentration of 0.19 μM to 0.39 μM, the primer 5960 may have a concentration of 0.35 μM to 0.55 μM, the primer 6162 may have a concentration of 0.26 μM to 0.46 μM, the primer 6364 may have a concentration of 0.15 μM to 0.35 μM, the primer 6566 may have a concentration of 0.40 μM to 0.60 μM, the primer 6768 may have a concentration of 0.40 μM to 0.60 μM, the primer 6970 may have a concentration of 0.25 μM to 0.45 µM, the primer 7172 may have a concentration of 0.14 µM to 0.34 µM, the primer 7374 may have a concentration of 1.00 µM to 1.20 µM, the primer 7576 may have a concentration of 0.40 µM to 0.60 µM, the primer 7778 may have a concentration of 0.28 µM to 0.48 µM, the primer 7980 may have a concentration of 0.70 µM to 0.90 µM, the primer 8182 may have a concentration of 0.30 µM to 0.50 µM, the primer 8384 may have a concentration of 1.20 µM to 1.40 µM, the primer 8586 may have a concentration of 0.18 µM to 0.38 µM, the primer 8788 may have a concentration of 0.25 µM to 0.45 µM, the primer 8990 may have a concentration of 0.05 µM to 0.25 µM, the primer 9192 may have a concentration of 0.15 µM to 0.35 µM, the primer 9394 may have a concentration of 0.17 µM to 0.37 µM, the primer 9596 may have a concentration of 0.50 µM to 0.70 µM, the primer 9798 may have a concentration of 0.20 µM to 0.40 µM, the primer 99100 may have a concentration of 0.45 µM to 0.65 µM, the primer 101102 may have a concentration of 1.70 µM to 1.90 µM, the primer 103104 may have a concentration of 0.17 µM to 0.37 µM, the primer 105106 may have a concentration of 0.35 µM to 0.55 µM, the primer 107108 may have a concentration of 0.28 µM to 0.48 µM, the primer 109110 may have a concentration of 0.55 µM to 0.75 µM, and the primer 111112 may have a concentration of 0.19 µM to 0.39 µM.

As a gene identifying method of identifying a human object according to the present invention, the method of analyzing microhaplotypes by using the NGS may be used.

The present invention can provide a method of simultaneously analyzing a plurality of microhaplotypes by using a next generation sequencing.

The present invention can provide a method of analyzing microhaplotypes by using a next generation sequencing, which is effective for analyzing a sample to which DNAs of different species are mixed.

The present invention can provide a method of analyzing microhaplotypes by using a next 5 generation sequencing, which is effective for analyzing degraded DNA.

DETAILED DESCRIPTION OF THE INVENTION

Figure 1:
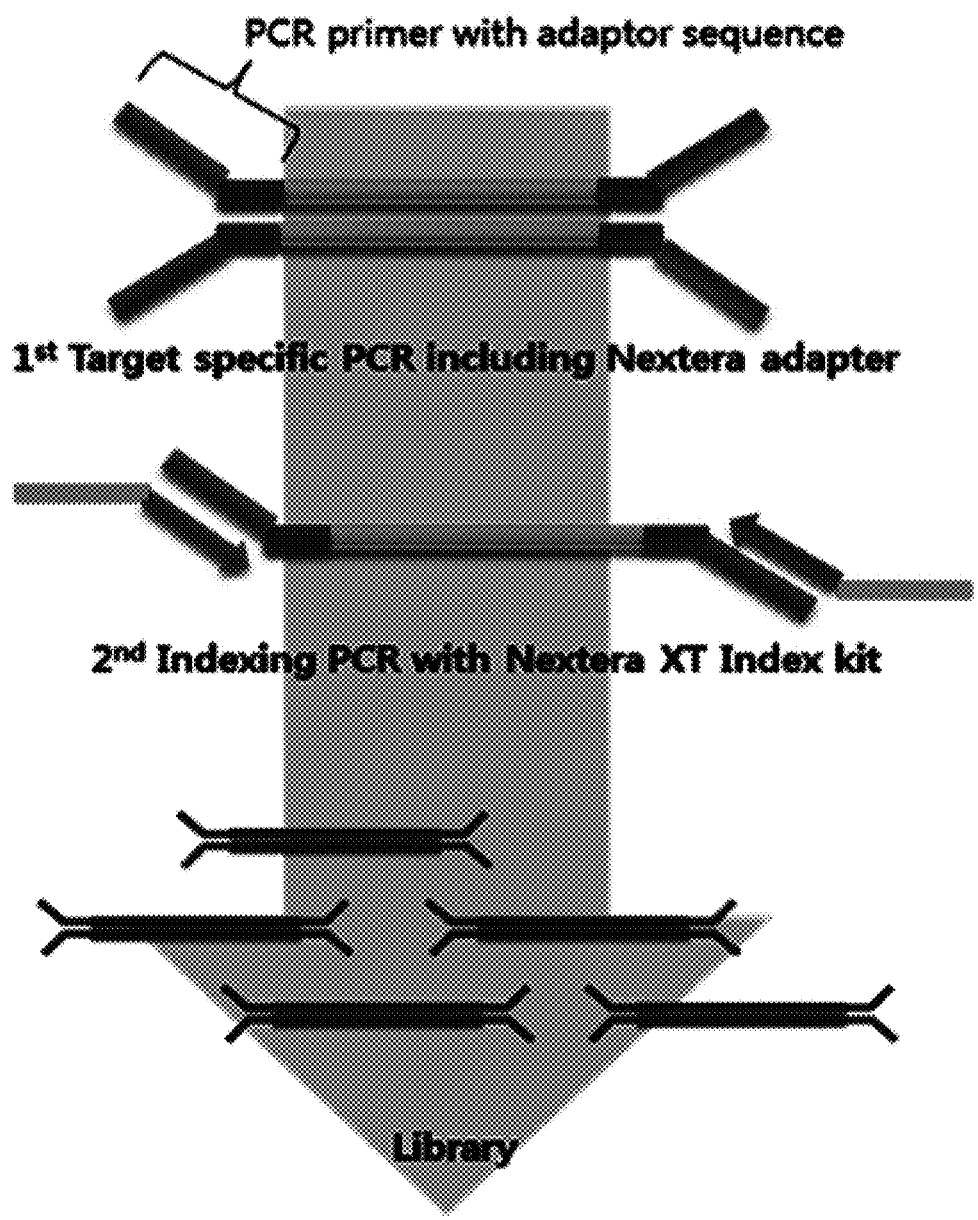
FIG. 1 is a schematic view of generating an NGS library according to a PCR scheme.
Figure 2:
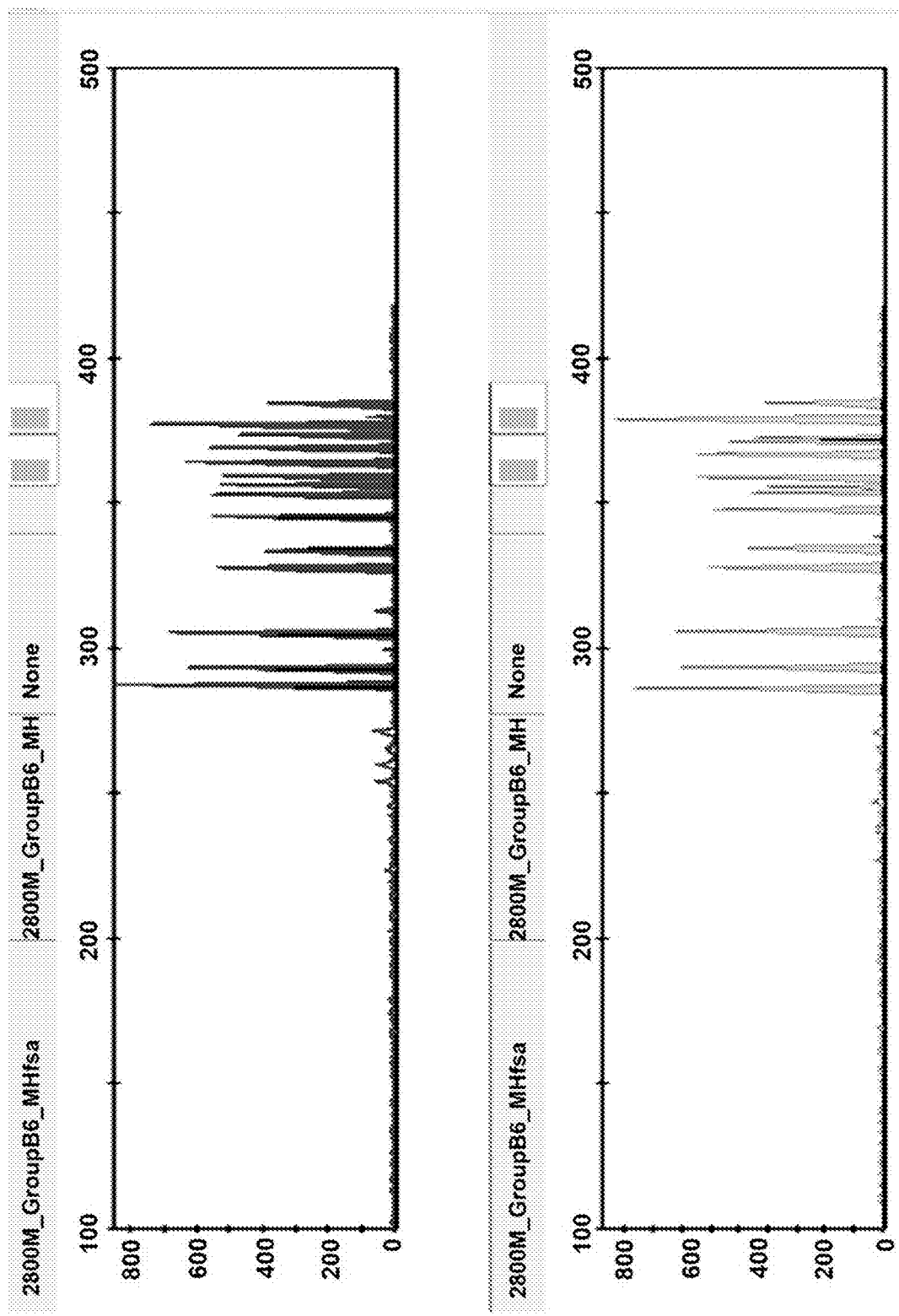
FIG. 2 is a result of capillary electrophoresis of a multi-plex PCR group 1 subject to 2800M.
Figure 3:
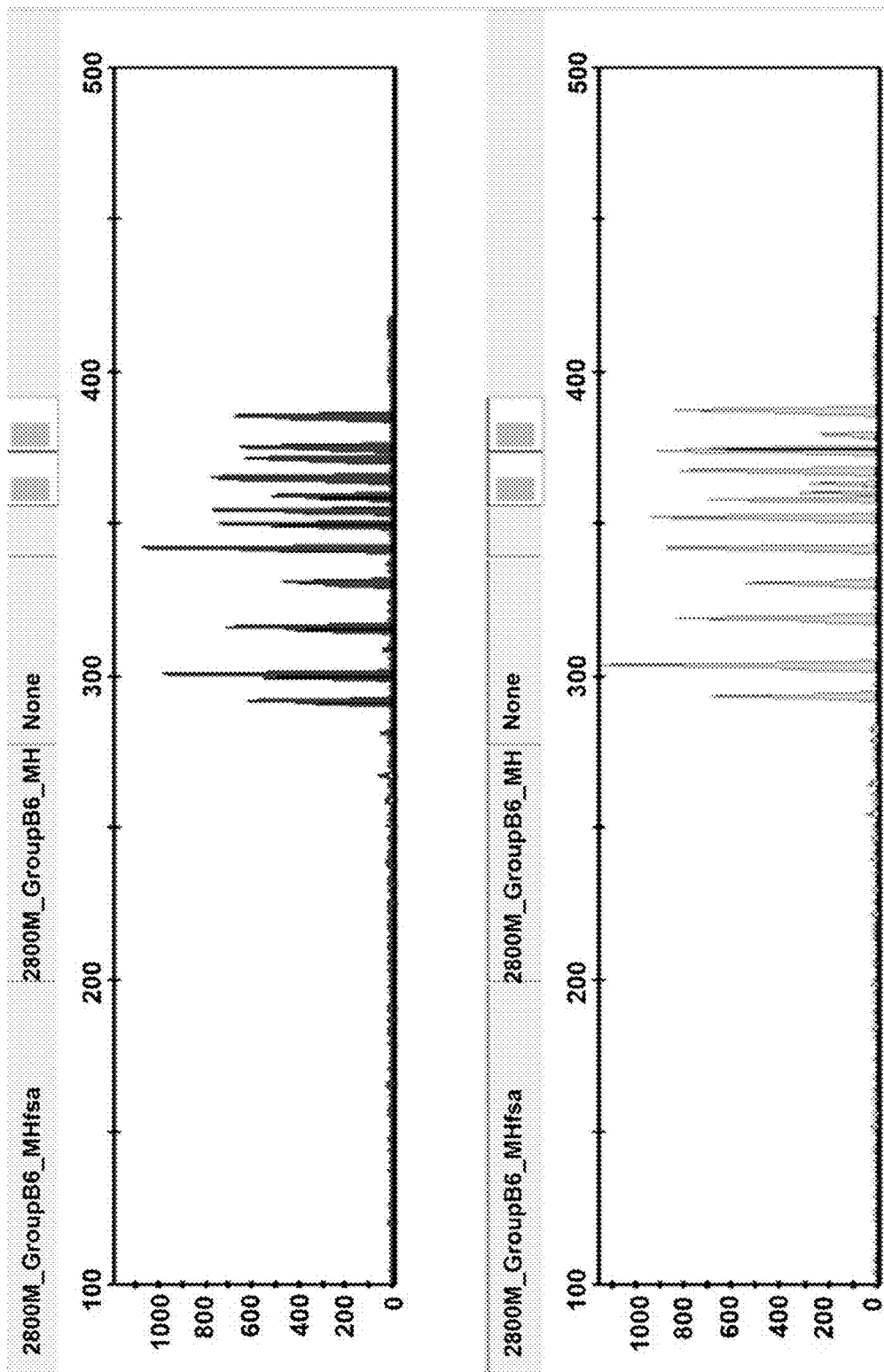
FIG. 3 is a result of capillary electrophoresis of a multi-plex PCR group 2 subject to 2800M.
Figure 4:
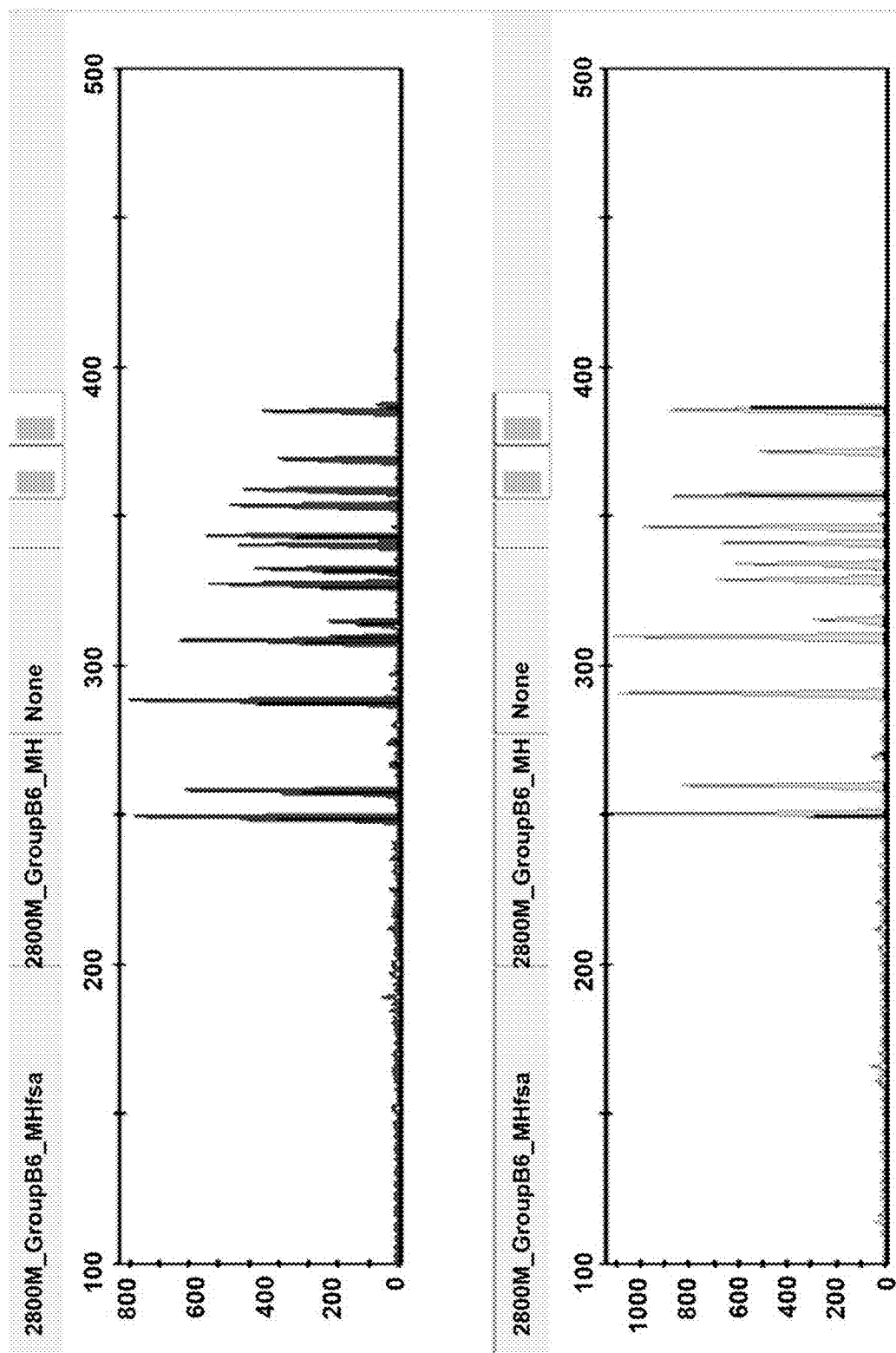
FIG. 4 is a result of capillary electrophoresis of a multi-plex PCR group 3 subject to 2800M.
Figure 5:
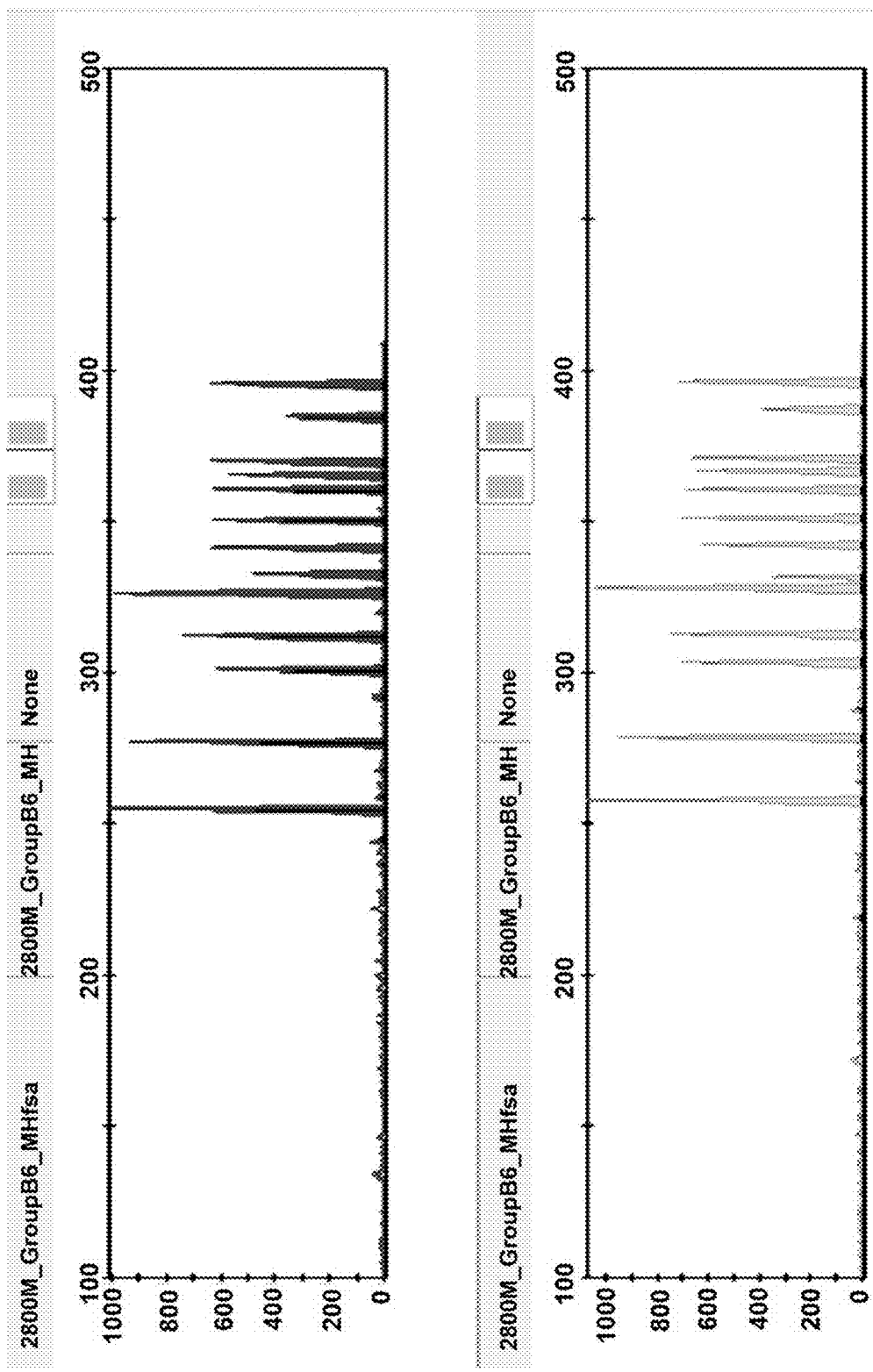
FIG. 5 is a result of capillary electrophoresis of a multi-plex PCR group 4 subject to 2800M.

Hereinafter, the present invention will be described in further detail with reference to examples. It will be obvious to a person having ordinary skill in the art that those examples are illustrative purposes only and are not to be construed as a limitation or change for the scope of the present invention.

1. Collecting Information On Microhaplotypes

Information on microhaplotypes was collected as shown in Tables 1 and 2 below, including 24 microhaplotypes ranked at top 1st to 51st in Ae rank and top 1st to 25th in I_n rank among MH presented the paper disclosed by Kidd et al. (Foresic Sci Int. Genet, 2017).

The nucleotide sequence information on the microhaplotypes was collected with reference to ALFRED (medicine.yale.edu/lab/kidd/research/alfred/), UCSC Genome Browser (GRCh37/hg19), and dbSNP (ncbi.nlm.nih.gov/projects/SNP/).

TABLE 1

| MH | Extent in bo | Ae rank | I_n rank | SNPs | #SNPs |
|---|---|---|---|---|---|
| D13S169 | 145 | 1 | 8 | rs1927847/rs9536429/rs7492234/rs9536430 | 4 |
| D5S1970 | 136 | 2 | 7 | rs10906617/rs74865590/rs438055/rs370672/rs6555108 | 4 |
| FRMD4A | 291 | 3 | 9 | rs10796164/rs10796165/rs17154765/rs1079616 | 5 |
| LINC0111 | 185 | 4 | 46 | rs2838081/rs2838082/rs78902658/rs2838083 | 4 |
| PFKP | 259 | 5 | 12 | rs3814588/rs6602026/rs3814589/rs3814590/rs9423466 | 5 |
| ITGB6 | 103 | 6 | 3 | rs12469721/rs3101043/rs3111398/rs72623112 | 4 |
| RBFOX1-1 | 173 | 7 | 16 | rs9937467/rs17670098/rs17670111/rs12929083/rs9926495 | 5 |
| FAM99A | 193 | 8 | 25 | rs12802112/rs28631755/rs7112918/rs4752777 | 4 |
| D21S1263 | 145 | 9 | 65 | rs8126597/rs8131148/rs6517971 | 3 |
| LRRC63 | 192 | 10 | 35 | rs7320507/rs9562648/rs9562649/rs2765614 | 4 |
| LRRN2 | 186 | 11 | 20 | rs17413714/rs2772234/rs1610401/rs1610400 | 4 |
| LOC642852 | 158 | 12 | 5 | rs6518223/rs2838868/rs7279250/rs8133697 | 4 |
| LINC01233 | 153 | 13 | 14 | rs12985452/rs4932999/rs4932769/rs2361019/rs2860462 | 5 |
| COL4A1 | 153 | 14 | 45 | rs1192204/rs1192205/rs3825483/rs3825481 | 4 |
| IGSF21 | 154 | 15 | 93 | rs11810587/rs1336130/rs1533623/rs1533622 | 4 |
| COL4A3 | 70 | 16 | 63 | rs6714835/rs6756898/rs12617010 | 3 |
| STATP1 | 200 | 17 | 24 | rs13131164/rs3775866/rs11725922/rs3775867/rs17088476 | 5 |
| SGCG | 140 | 18 | 53 | rs8181845/rs679482/rs9510616 | 3 |
| PLCG2 | 142 | 19 | 21 | rs16956011/rs3934955/rs3934956/rs4073828 | 4 |
| D13S1320 | 96 | 20 | 58 | rs4884651/rs9529023/rs7329287 | 3 |
| D18S1122 | 82 | 21 | 18 | rs621320/rs621340/rs678179/rs621766 | 4 |
| KIF16B | 140 | 22 | 49 | rs6044080/rs17674942/rs6044081/rs16997830 | 4 |
| GFI1B | 153 | 23 | 32 | rs606141/rs8193001/rs56256724/rs2073578/rs633153 | 5 |
| D22S1159 | 146 | 24 | 74 | rs763040/rs5764924/rs763041 | 3 |
| CPNE4 | 184 | 25 | 68 | rs1225051/rs1225050/rs1225049/rs1225048 | 4 |

TABLE 1-continued

| MH | Extent in bo | Ae rank | I_n rank | SNPs | #SNPs |
|---|---|---|---|---|---|
| COG2 | 279 | 26 | 26 | rs2479135/rs2296796/rs2296797/rs2296798 | 4 |
| CNTN5 | 189 | 27 | 42 | rs12421109/rs12289401/rs12420819/rs770566 | 4 |
| CEP104 | 259 | 28 | 4 | rs4648344/rs6663840/rs58111155/rs6688969 | 4 |
| LPPR1 | 112 | 29 | 6 | rs10125791/rs2987741/rs7047561 | 3 |
| D12S290 | 153 | 30 | 84 | rs10506052/rs4931233/rs10506053/rs4931234 | 4 |
| CYYR1 | 134 | 31 | 15 | rs961302/rs17002090/rs961301/rs2830208 | 4 |
| RBFOX1 | 113 | 32 | 17 | rs1395579/rs1395580/rs1395582/rs9939248 | 4 |
| FRMD3 | 141 | 33 | 54 | rs10867949/rs4282648/rs10780576/rs7046769 | 4 |
| TOM1L1 | 130 | 34 | 66 | rs2934897/rs7207239/rs16955257/rs7212184 | 4 |
| SUDS3 | 71 | 35 | 81 | rs1503767/rs11068953 | 2 |
| KANK1 | 77 | 36 | 77 | rs10815466/rs9408671/rs17431629 | 3 |
| MYO5C | 74 | 37 | 56 | rs1063902/rs4219 | 2 |
| NELFA | 34 | 38 | 70 | rs3135123/rs495367 | 2 |
| SEMA6D | 121 | 39 | 31 | rs701463/rs701464 | 2 |
| C14ORF43 | 158 | 40 | 55 | rs12717560/rs12878166 | 3 |
| CEBPB | 105 | 41 | 73 | rs6122890/rs6095836/rs6012881 | 4 |
| TENM4 | 181 | 42 | 27 | rs493442/rs17137917/rs551850/rs17137926 | 2 |
| ARHGAP27 | 186 | 43 | 108 | rs1059504/rs8327 | 3 |
| ADH7 | 152 | 44 | 43 | rs4699748/rs2584461/rs1442492 | 2 |
| RXRA | 193 | 45 | 129 | rs3118582/rs10776839 | 4 |
| HRH4 | 135 | 47 | 39 | rs16940823/rs17187688/rs17187695/rs1945150 | 2 |
| OR52S1P1 | 122 | 49 | 115 | rs10500616/rs2499936 | 2 |
| GNGT2 | 42 | 51 | 112 | rs2233362/rs634370 | 2 |
| ESRRG | 17 | 53 | 22 | rs4528199/rs6604596 | 4 |
| LOC28716 | 170 | 54 | 23 | rs12123330/rs16840876/rs56212601/rs4468133 | 4 |
| DRD2-NCAM | 261 | 64 | 13 | rs1107162/rs2075654/rs1079727/rs2002453 | 3 |
| HERC1 | 137 | 80 | 10 | rs11631544/rs10152453/rs80047978 | 3 |
| EDAR | 124 | 97 | 2 | rs260694/rs11123719/rs11691107 | 3 |
| ZC3H7B | 78 | 101 | 11 | rs8137373/rs2235845 | 2 |
| KLK5 | 63 | 106 | 19 | rs10408594/rs11084040/rs10408037/rs8104441 | 4 |
| ELK2B | 95 | 115 | 1 | rs28529526/rs10134526 | 2 |

TABLE 2

| MH | Chr # | SNP positions (build37) |
|---|---|---|
| D13S169 | 13 | 54060827 54060881 54060892 54060972 |
| D5S1970 | 5 | 2448024 2448052 2448146 2448160 |
| FRMD4A | 10 | 14208361 14208510 14208588 14208611 14208652 |
| LINC0111 | 21 | 43062859 43062929 43063018 43063044 |
| PFKP | 10 | 3162410 3162423 3162486 3162525 3162669 |
| ITGB6 | 2 | 161079411 161079435 161079450 161079514 |
| RBFOX1-1 | 16 | 7209208 7209247 7209267 7209311 7209381 |
| FAM99A | 11 | 1690791 1690911 1690969 1690984 |
| D21S1263 | 21 | 21880086 21880191 21880231 |
| LRRC63 | 13 | 46865930 46865970 46866084 46866122 |
| LRRN2 | 1 | 204633340 204633397 204633500 204633526 |
| LOC642852 | 21 | 46714549 46714641 46714692 46714707 |
| LINC01233 | 19 | 22729500 22729551 22729582 22729613 22729653 |
| COL4A1 | 13 | 110806699 110806742 110806759 110806852 |
| IGSF21 | 1 | 18722692 18722713 18722801 18722846 |
| COL4A3 | 2 | 228092389 228092406 228092459 |
| STATP1 | 4 | 68444102 68444180 68444192 68444257 68444302 |
| SGCG | 13 | 23765541 23765635 23765681 |
| PLCG2 | 16 | 81970353 81970366 81970407 81970495 |
| D13S1320 | 13 | 66712732 66712790 66712828 |
| D18S1122 | 18 | 76089886 76089907 76089945 76089968 |
| KIF16B | 20 | 16513260 16513316 16513342 16513400 |
| GFI1B | 9 | 135862479 135862495 135862563 135862592 135862632 |
| D22S1159 | 22 | 44763606 44763651 44763752 |
| CPNE4 | 3 | 131645972 131646001 131646087 131646156 |
| COG2 | 1 | 230820351 230820578 230820605 230820630 |
| CNTN5 | 11 | 99880163 99880224 99880282 99880352 |
| CEP104 | 1 | 3743132 3743319 3743350 3743391 |
| LPPR1 | 9 | 103969740 103969775 103969852 |
| D12S290 | 12 | 30170229 30170306 30170359 30170382 |
| CYYR1 | 21 | 27782968 27782992 27783039 27783102 |
| RBFOX1 | 16 | 7587734 7587746 7587804 7587847 |
| FRMD3 | 9 | 85808649 85808708 85808730 85808790 |
| TOM1L1 | 17 | 52942428 52942456 52942491 52942558 |
| SUDS3 | 12 | 118889488 118889559 |
| KANK1 | 9 | 680714 680763 680791 |
| MYO5C | 15 | 52484950 52485024 |
| NELFA | 4 | 1986938 1986972 |
| SEMA6D | 15 | 46870734 46870855 |
| C14ORF43 | 14 | 74250557 74250715 |
| CEBPB | 20 | 48844260 48844293 48844365 |
| TENM4 | 11 | 78947596 78947625 78947645 78947777 |
| ARHGAP27 | 17 | 43472321 43472507 |
| ADH7 | 4 | 100321443 100321573 100321595 |
| RXRA | 9 | 137417115 137417308 |
| HRH4 | 18 | 22137319 22137396 22137412 22137454 |
| OR52S1P1 | 11 | 5109946 5110068 |
| GNGT2 | 17 | 47287067 47287109 |
| ESRRG | 1 | 216634428 216634445 |
| LOC28716 | 1 | 4227464 4227561 4227624 4227634 |
| DRD2-NCAM | 11 | 113289037 113289066 113289182 113289298 |
| HERC1 | 15 | 64098557 64098613 64098694 |
| EDAR | 2 | 109586313 109586371 109586437 |
| ZC3H7B | 22 | 41729216 41729294 |
| KLK5 | 19 | 51441744 51441759 51441783 51441807 |
| ELK2B | 14 | 106009477 106009572 |

2. Designing Primer And Establishing Multiplex PCR System

A candidate primer was designed using the pimer3 (frodo.wi.mit.edu/primer3/) and so on to amplify a site representing the microhaplotype into an amplificon of 270 bp or less, based on the collected information on a microhaplotype marker.

The designed candidate primer was synthesized by including Nextera™ adapter sequence in a 5' terminal, so that an NGS runnable library in a MiSeg™ system (Illumina, Inc, San Diego, Calif., USA) is generated according to a PCR scheme (FIG. 1, Table 3, Table 4, Table 5, and Table 6).

TABLE 3

Group A

| Marker | | Sequence (5'→3') |
|---|---|---|
| COG2 | F190 | tcgtcggcagcgtcagatgtgtataagagacagCAGCCCATGTTTGTCGATT |
| | R340 | gtctcgtgggctcggagatgtgtataagagacagGCCACAATCCAAGTTCCCTA |
| ITGB6 | F201 | tcgtcggcagcgtcagatgtgtataagagacagGAACTGTACCCTTGGCAGGA |
| | R358 | gtctcgtgggctcggagatgtgtataagagacagCAATGTCCTTGAGGCTCGTA |
| D18S1122 | F222 | tcgtcggcagcgtcagatgtgtataagagacagCACCCACTGAAGTTTGAGCA |
| | R390 | gtctcgtgggctcggagatgtgtataagagacagTGATCCTAATCAAGGCTATGGA |
| GFI1B | F230 | tcgtcggcagcgtcagatgtgtataagagacagGACTGGTCCAAAGTCTTCCC |
| | R424 | gtctcgtgggctcggagatgtgtataagagacagCCATCAGCATCAATAGCCAC |
| D21S1263 | F271 | tcgtcggcagcgtcagatgtgtataagagacagGGAGCCTAAAAGAAGGTCACA |
| | R468 | gtacgtgggctcggagatgtgtataagagacagCCTGAACACTTTGGGGCAG |
| D5S1970 | F254 | tcgtcggcagcgtcagatgtgtataagagacagCACATGGAGGACAAAAGTGAA |
| | R463 | gtctcgtgggctcggagatgtgtataagagacagGTGCTGGTGATGACAAGTGAG |
| LOC642852 | F216 | tcgtcggcagcgtcagatgtgtataagagacagGTCATCTGGGAAACGTGGG |
| | R435 | gtctcgtgggctcggagatgtgtataagagacagCGTCTGCATTTCCGCTGAC |
| COL4A1 | F206 | tcgtcggcagcgtcagatgtgtataagagacagAGTGTATCAAACAGGGGCCTT |
| | R431 | gtctcgtgggctcggagatgtgtataagagacagCACGTGGGGAGTACACATTC |
| IGSF21 | F208 | tcgtcggcagcgtcagatgtgtataagagacagGTAATTTGGGGTCCAGAGCA |
| | R434 | gtctcgtgggctcggagatgtgtataagagacagAATTCGCAACAGTGAAAGCA |
| RXRA | F231 | tcgtcggcagcgtcagatgtgtataagagacagCACAGCAATCCCCCTTGAG |
| | R463 | gtctcgtgggctcggagatgtgtataagagacagGGCTCTGATCTGACGGCAA |
| SGCG | F212 | tcgtcggcagcgtcagatgtgtataagagacagGAGGAGAGACAGCAAGGAGAA |
| | R447 | gtctcgtgggcttggagatgtgtataagagacagTCTGCCAAGTGATCAACTCAA |
| LINC0111 | F280 | tcgtcggcagcgtcagatgtgtataagagacagGAGGGTGTGTTTAGGATGGG |
| | R519 | gtctcgtgggctcggagatgtgtataagagacagCTCCCCTGGCCAAACATTA |
| LRRN2 | F227 | ccgtcggcagcgtcagatgtgtataagagacagGTTTGTCTCCCCACAAAGCA |
| | R472 | gtctcgtgggctcggagatgtgtataagagacagGTCACATCACCATCTCCGTC |
| CPNE4 | F222 | tcgtcggcagcgtcagatgtgtataagagacagCTATCTTATTTAATATTCAT-AACAACCTT |
| | R473 | gtctcgtgggctcggagatgtgtataagagacogGAAAGTGCCTGGGATCCACT |

TABLE 4

Group B

| Marker | | Sequence (5'→3') |
|---|---|---|
| GNGT2 | F158 | tcgtcggcagcgtcagatgtgtataagagacagACACCCATCCAATGACAAGG |
| | R314 | gtctcgtgggctcggagatgtgtataagagacagGAGCACGGAAGTTAGGATGG |
| COL4A3 | F216 | tcgtcggcagcgtcagatgtgtataagagacagTCCTTAGCCTCTCAAAATCC |
| | R382 | gtctcgtgggctcggagatgtgtataagagacagGGAAATGAACTTCCATCAGCA |
| SUDS3 | F215 | tcgtcggcagcgtcagatgtgtataagagacagAGGAACACTGGTATAGGAGGAGA |
| | R394 | gtctcgtgggctcggagatgtgtataagagacagGGAGGGTTGTTTCCTTTGTG |
| D13S169 | F277 | tcgtcggcagcgtcagatgtgtataagagacagCTGGAATCATAAGCATAGCACA |
| | R469 | gtctcgtgggctcggagatgtgtataagagacagAATGCAGAACTCACATGTTAAGG |
| PLCG2 | F212 | tcgtcggcagcgtcagatgtgtataagagacagGGGCTTTCTGCTCAGACTTT |
| | R416 | gtctcgtgggctcggagatgtgtataagagacagGTTCCATTCTGTGGAATCCG |
| D22S1159 | F220 | tcgtcggcagcgtcagatgtgtataagagacagCTCCTTTAGGGGTGGCAAGT |
| | R435 | gtctcgtgggctcggagatgtgtataagagacagTAGGGACTGGGGAACTCCTT |
| KIF16B | F227 | tcgtcggcagcgtcagatgtgtataagagacagAAGAGAACAAACCACCTGGG |
| | R447 | gtctcgtgggctcggagatgtgtataagagacagCAAGTCAATGTGAGCATTACCA |
| ADH7 | F213 | tcgtcggcagcgtcagatgtgtataagagacagACACAGGAGATGGATGACTCC |
| | R437 | gtctcgtgggctcggagatgtgtataagagacagCTGGCTTTCTCCACATGTCA |

TABLE 4-continued

Group B

| Marker | | Sequence (5'→3') |
|---|---|---|
| C14ORF43 | F215 | tcgtcggcagcgtcagatgtgtataagagacagGGTGTCTGGAAAACTGTAGCG |
| | R444 | gtctcgtgggctcggagatgtgtataagagacagCTGAGAGAAGCCAATGCAGG |
| FAM99A | F282 | tcgtcggcagcgtcagatgtgtataagagacagCCTGCCTGCTTTTCCTGAT |
| | R517 | gtctcgtgggctcggagatgtgtataagagacagGAGATGTCTCCTGGGCAGC |
| FRMD4A | F205 | tcgtcggcagcgtcagatgtgtataagagacagGCACAGCTTTGTTTTATCTGGA |
| | R443 | gtctcgtgggctcggagatgtgtataagagacagCCTATCCTGTTCTTTGGGTGAG |
| OR52S1P | F160 | tcgtcggcagcgtcagatgtgtataagagacagTCCATTTTGCTGACCTAAACCT |
| | R402 | gtctcgtgggctcggagatgtgtataagagacagAAAAAAACAAGTATAAGGGATGACA |
| ARHGAP27 | F222 | tcgtcggcagcgtcagatgtgtataagagacagGCCTGAGGAGGATAGCTTCA |
| | R470 | gtctcgtgggctcggagatgtgtataagagacagGTGTGCGATAGCGTGTGTG |
| LRRC63 | F257 | tcgtcggcagcgtcagatgtgtataagagacagATAGTCTCCGTAAGGCCTGG |
| | R510 | gtctcgtgggctcggagatgtgtataagagacagTGGTGTATTGCCAAACAGAAA |

TABLE 5

Group C

| Marker | | Sequence (5'→3') |
|---|---|---|
| KLK5 | F221 | tcgtcggcagcgtcagatgtgtataagagacagAGACAGACCCACTACGGGTG |
| | R335 | gtctcgtgggacggagatgtgtataagagacagTCAAGAAATCCAGGTAAGGG |
| USH2A | F167 | tcgtcggcagcgtcagatgtgtataagagacagAGAAACTTTGCCTTTTGACCA |
| | R290 | gtctcgtgggctcggagatgtgtataagagacagGCCCTGCCTTCTAGTTCTGA |
| D13S1320 | F226 | tcgtcggcagcgtcagatgtgtataagagacagTTCTCTACTAAGAAACCAACCACAC |
| | R379 | gtctcgtgggctcggagatgtgtataagagacagTGAAAAGGGAAGTGGAAAACA |
| SEMA6D | F224 | tcgtcggcagcgtcagatgtgtataagagacagCTCTCAAGCCCACTCTCTGG |
| | R395 | gtctcgtgggctcggagatgtgtataagagacagGAAGTAGAAAGCCTCCATTGTG |
| MYOSC | F215 | tcgtcggcagcgtcagatgtgtataagagacagAGGGTCCGACACAATTTTTTA |
| | R392 | gtctcgtgggctcggagatgtgtataagagccagACCTGCCAACATATTCACCA |
| TOM1L1 | F215 | tcgtcggcagcgtcagatgtgtataagagacagTCTCTCTCCATTATTCCCTGAAC |
| | R404 | gtctcgtgggctcggagatgtgtataagagacagGGAACATCACGGGAATCTTTT |
| HERC1 | F228 | tcgtcggcagcgtcagatgtgtataagagacagCAAAGGCCTATCTCAAAGGTG |
| | R422 | gtctcgtgggctcggagatgtgtataagagacagGGGGTGGATGGAGCAGTAG |
| DRD2NCAM | F219 | tcgtcggcagcgtcagatgtgtataagagacagATGCCCATGGGTGTCTGAG |
| | R421 | gtctcgtgggctcggagatgtgtataagagacagGTGATGAATGGGTGCCAAAT |
| ELK2B | F225 | tcgtcggcagcgtcagatgtgtataagagacagAAGTTAATCTTAAGAACAATCACCA |
| | R432 | gtctcgtgggctcggagatgtgtataagagacagCAAGAATCTCTACTTTTTAACTGATT |
| FRMD3 | F193 | tcgtcggcagcgtcagatgtgtataagagacagTGAATGTGGTAACTGAGACTAGGA |
| | R412 | gtctcgtgggctcggagatgtgtataagagacagTGATCCTTGGGGGAGCTTTA |
| CEBPB | F220 | tcgtcggcagcgtcagatgtgtataagagacagAGCAGGGCCAGGCATATAG |
| | R443 | gtctcgtgggctcggagatgtgtataagagacagCATCCTCACCACAAACCTCA |
| LINC01233 | F148 | tcgtcggcagcgtcagatgtgtataagagacagAAGGCCATGTTACATTGGAAA |
| | R334 | gtctcgtgggctcggagatgtgtataagagacagGGTCGCATGTCTCCTGGTAG |
| STATP1 | F221 | tcgtcggcagcgtcagatgtgtataagagacagAGCCATTGCAGTCATCTGAA |
| | R472 | gtctcgtgggctcggagatgtgtataagagacagTGGAAGCACCATACCACTCA |
| RBFOX1-1 | F201 | tcgtcggcagcgtcagatgtgtataagagacagGCCCGGAGATTGTTTCAAGT |
| | R455 | gtctcgtgggctcggagatgtgtataagagacagCCCGTTTCTGATTCTCTTTCA |

TABLE 6

Group D

| Marker | | Sequence (5'→3') |
|---|---|---|
| NELFA | F203 | tcgtcggcagcgtcagatgtgtataagagacagAGCCCATCTTGAGCACAGAA |
| | R324 | gtctcgtgggctcggagatgtgtataagagacagGGATAATAAGCTCCTTTCTTCCC |
| ZC3H7B | F213 | tcgtcggcagcgtcagatgtgtataagagacagCCAGAGCTTTGCAGCACTTT |
| | R357 | gtctcgtgggctcggagatgtgtataagagacagTGCTACAAAGGCAGATCATCA |
| EDAR | F230 | tcgtcggcagcgtcagatgtgtataagagacagTGAAGAGCTAACTTGTGCAGG |
| | R395 | gtctcgtgggctcggagatgtgtataagagacagGCTGGCTAGACCCTCCATTA |
| KANK1 | F172 | tcgtcggcagcgtcagatgtgtataagagacagTTTCTGCCCTCAAGGATTGT |
| | R347 | gtctcgtgggctcggagatgtgtataagagacagAGGGCAGGGGTGCAATCT |
| RBFOX1 | F228 | tcgtcggcagcgtcagatgtgtataagagacagCTTGGGTCCATCTCAGGAATA |
| | R416 | gtctcgtgggctcggagatgtgtataagagacagAATACCACGGATTTCCCCTC |
| PFKP | F199 | tcgtcggcagcgtcagatgtgtataagagacagCGTTCTTTTTTCCCCCAGA |
| | R391 | gtctcgtgggctcggagatgtgtataagagacagTGCTGGTACAATCACAGGAGA |
| LPPR1 | F228 | tcgtcggcagcgtcagatgtgtataagagacagGGGGATTGGCAGTCTTCAT |
| | R421 | gtctcgtgggctcggagatgtgtataagagacagTGGCCCAGTATCATACAGCC |
| CYYR1 | F228 | tcgtcggcagcgtcagatgtgtataagagacagCCAGGGAAGATATGTGCTCAA |
| | R431 | gtctcgtgggctcggagatgtgtataagagacagCCTTGGATTGCAAGAGACTCC |
| HRH4 | F202 | tcgtcggcagcgtcagatgtgtataagagacagCCAGGGGACTGATTTTTCCT |
| | R416 | gtctcgtgggctcggagatgtgtataagagacagTGGAACCTATAAATAATGCAAAG |
| LOC28716 | F225 | tcgtcggcagcgtcagatgtgtataagagacagCTGCTGGCTGTGTGGATGT |
| | R451 | gtctcgtgggctcggagatgtgtataagagacagTGTCAGATTTTCTTAGGACCGA |
| D12S290 | F222 | tcgtcggcagcgtcagatgtgtataagagacagCTTCAAGGTATTTCCAGTACCCA |
| | R453 | gtctcgtgggctcggagatgtgtataagagacagCCTGAGCCACTGATTTTTCC |
| TENM4 | F222 | tcgtcggcagcgtcagatgtgtataagagacagTGTCAGCACTCCAGTATCACTTT |
| | R458 | gtctcgtgggctcggagatgtgtataagagacagGCCGCAAGGGAGTCAGTAT |
| CNTN5 | F228 | tcgtcggcagcgtcagatgtgtataagagacagGGGAAACAAAGGTATGTAAAGGC |
| | R481 | gtctcgtgggctcggagatgtgtataagagacagCCAGTTTCCCTGTAACAACTCA |
| CEP104 | F230 | tcgtcggcagcgscagatgtgtataagagacagGTTTTCCATTCAGCTGGGAG |
| | R492 | gtctcgtgggctcggagatgtgtataagagacagCAACAGGCTCTCACTCACTCA |

A primer set, which indicates a PCR yield suitable for multiplex PCR amplification without observation of non-specific PCR amplification, was selected by performing the duplex PCR using a candidate primer set and a Y-M175 primer set for each microhaplotype marker, with respect to 2800M Control DNA (Promega, Madison, Wis., USA).

The PCR was performed after divided into four multiplex sets, a primer concentration was adjusted to uniform the PCR yield, it was confirmed that there was no interference between primers, and finally, a multiplex PCR system capable of amplifying 56 microhaplotypes at once was established.

Duplex PCR And Indexing PCR

A target specific primary duplex PCR was performed using 20 µl of a reaction solution by adding 1 ng of template DNA, 2.0 µl of Gold ST*R 10x Buffer (Promega), 0.5 µM of the candidate primer set, 1.0 µM of the Y-M175 primer set and 1.0 U of AmpliTaq Gold™ DNA Polymerase (Applied Biosystems®, Foster City, Calif., USA).

The template DNA was selected from 2800M ContrlolDNA (Promega) and random male DNA. The primary PCR was processed at 95° C. for 11 minutes, followed by 26 cycles of 94° C. for 20 seconds, 59° C. for 1 minute, and 72° C. for 45 seconds, and then reacted at 72° C. for 5 minutes.

A secondary PCR for generating the NGS library was performed using 20 µl of a reaction solution by adding 1/10-diluted primary PCR amplicon, 2.0 µl of Gold ST*R 10x Buffer (Promega), 0.5 µM of an index primer tagged with FAM or HEX, 1.0 U of AmpliTaq Gold™ DNA Polymerase (Applied Biosystems®).

The secondary PCR was processed at 95° C. for 15 minutes, followed by 15 cycles of 94° C. for 20 seconds, 59° C. for 30 seconds, and 72° C. for 45 seconds, and then reacted at 60° C. for 30 minutes.

For the generated PCR amplicon, after processed by capillary electrophoresis using an Applied Biosystems® 3130 xl Genetic Analyzer (Applied Biosystems®) according to an usual manner, a size of the amplicon was determined by using GeneMapper® ID Software Version 3.2 (Applied Biosystems®).

Multiplex PCR And Indexing PCR

Multiplex PCR tests were performed after the amplicons of 56 microhaplotype markers were divided into four groups without duplication of the size as shown in FIG. 7 with reference to the target amplicon size observed in the duplex PCR result for each microhaplotype marker.

TABLE 7

| | Marker | Target |
|---|---|---|
| Group A | | |
| 1 | COG2 | 151 |
| 2 | ITGB6 | 158 |
| 3 | D18S1122 | 169 |

TABLE 7-continued

| | Marker | Target |
|---|---|---|
| 4 | GFI1B | 195 |
| 5 | D21S1263 | 198 |
| 6 | D5S1970 | 210 |
| 7 | LOC642852 | 220 |
| 8 | COL4A1 | 226 |
| 9 | IGSF21 | 227 |
| 10 | RXRA | 233 |
| 11 | SGCG | 236 |
| 12 | LINC0111 | 240 |
| 13 | LRRN2 | 246 |
| 14 | CPNE4 | 247/252 |
| Group B | | |
| 1 | GNGT2 | 157 |
| 2 | COL4A3 | 167 |
| 3 | SUDS3 | 180 |
| 4 | D13S169 | 193 |
| 5 | PLCG2 | 205 |
| 6 | D22S1159 | 216 |
| 7 | KIF16B | 221 |
| 8 | ADH7 | 225 |
| 9 | C14ORF43 | 230 |
| 10 | FAM99A | 236 |
| 11 | FRMD4A | 239 |
| 12 | OR52S1P | 243 |
| 13 | ARHGAP27 | 249 |
| 14 | LRRC63 | 254 |
| Group C | | |
| 1 | KLK5 | 115 |
| 2 | USH2A | 124 |
| 3 | D13S1320 | 154 |
| 4 | SEMA6D | 172 |
| 5 | MYO5C | 178 |
| 6 | TOM1L1 | 190 |
| 7 | HERC1 | 195 |
| 8 | DRD2NCAM | 195 |
| 9 | ELK2B | 208 |
| 10 | FRMD3 | 220 |
| 11 | CEBPB | 224 |
| 12 | LINC01233 | 237 |
| 13 | STATP1 | 252 |
| 14 | RBFOX1-1 | 255 |
| Group D | | |
| 1 | NELFA | 122 |
| 2 | ZC3H7B | 145 |
| 3 | EDAR | 166 |
| 4 | KANK1 | 176 |
| 5 | RBFOX1 | 189 |
| 6 | PFKP | 193 |
| 7 | LPPR1 | 194 |
| 8 | CYYR1 | 204 |
| 9 | HRH4 | 215 |
| 10 | LOC28716 | 227 |
| 11 | D12S290 | 232 |
| 12 | TENM4 | 237 |
| 13 | CNTN5 | 254 |
| 14 | CEP104 | 263 |

The primary target specific multiplex PCR was performed after changing the duplex PCR condition for amplifying the candidate primer set into 3.33 μl of 6× primer mix and 4.0 U of AmpliTaq Gold™ DNA Polymerase (Applied Biosystems®), and applying the same thermal cycle.

The secondary PCR for generating the NGS library was performed after changing the duplex PCR condition for amplifying the candidate primer set into 2.5 U of AmpliTaq Gold™ DNA Polymerase (Applied Biosystems®), and applying the same thermal cycle.

The multiplex PCR system was established while confirming that there was no interference between the primers during the multiplex PCR amplification and adjusting a primer concentration so as to allow the PCR yield to be uniform (FIGS. 2 to 5). In this case, a coverage balancing was performed to prevent the maximum NGS read counts for each marker from exceeding two times the minimum NGS read counts in the NGS result.

Finally, final concentrations (μM) of the primers to amplify the 56 microhaplotypes are shown in Tables 8 to 11.

TABLE 8

| Group A | Marker | Primer | 2800 M Size | (uM) |
|---|---|---|---|---|
| 1 | COG2 | F190/R340 | 286.2 | 0.28 |
| 2 | ITGB6 | F201/R358 | 292.4 | 0.16 |
| 3 | D18S1122 | F222/R390 | 303.2 | 0.18 |
| 4 | GFI1B | F230/R424 | 328.2 | 0.18 |
| 5 | D21S1263 | F271/R468 | 333.5 | 0.50 |
| 6 | D5S1970 | F254/R463 | 345.0 | 0.90 |
| 7 | LOC642852 | F216/R435 | 354.0 | 0.32 |
| 8 | COL4A1 | F206/R431 | 358.2 | 0.25 |
| 9 | IGSF21 | F208/R434 | 360.6 | 0.40 |
| 10 | RXRA | F231/R463 | 365.6 | 0.25 |
| 11 | SGCG | F212/R447 | 370.4 | 0.50 |
| 12 | LINC0111 | F280/R519 | 374.7 | 0.40 |
| 13 | LRRN2 | F227/R472 | 378.9 | 0.25 |
| 14 | CPNE4 | F222/R473 | 386.0 | 2.00 |

TABLE 9

| Group B | Marker | Primer | 2800 M Size | (uM) |
|---|---|---|---|---|
| 1 | GNGT2 | F158/R314 | 291.1 | 0.24 |
| 2 | COL4A3 | F216/R382 | 300.0 | 0.36 |
| 3 | SUDS3 | F215/R394 | 314.3 | 0.28 |
| 4 | D13S169 | F277/R469 | 329.8 | 0.55 |
| 5 | PLCG2 | F212/R416 | 340.7 | 0.28 |
| 6 | D22S1159 | F220/R435 | 350.2 | 0.18 |
| 7 | KIF16B | F227/R447 | 354.8 | 0.29 |
| 8 | ADH7 | F213/R437 | 359.6 | 0.36 |
| 9 | C14ORF43 | F215/R444 | 365.5 | 0.38 |
| 10 | FAM99A | F282/R517 | 367.5 | 0.60 |
| 11 | FRMD4A | F205/R443 | 372.5 | 0.31 |
| 12 | OR52S1P | F160/R402 | 376.7 | 1.40 |
| 13 | ARHGAP27 | F222/R470 | 379.1 | 0.50 |
| 14 | LRRC63 | F257/R510 | 387.0 | 0.55 |

TABLE 10

| Group C | Marker | Primer | 2800 M Size | (uM) |
|---|---|---|---|---|
| 1 | KLK5 | F221/R335 | 248.6 | 0.29 |
| 2 | USH2A | F167/R290 | 257.4 | 0.45 |
| 3 | D13S1320 | F226/R379 | 287.6 | 0.36 |
| 4 | SEMA6D | F224/R395 | 307.5 | 0.25 |
| 5 | MYO5C | F215/R392 | 313.2 | 0.50 |
| 6 | TOM1L1 | F215/R404 | 325.7 | 0.50 |
| 7 | HERC1 | F228/R422 | 331.0 | 0.34 |
| 8 | DRD2NCAM | F219/R421 | 339.5 | 0.24 |
| 9 | ELK2B | F225/R432 | 342.6 | 1.00 |
| 10 | FRMD3 | F193/R412 | 353.9 | 0.50 |
| 11 | CEBPB | F220/R443 | 359.5 | 0.37 |
| 12 | LINC01233 | F148/R384 | 370.4 | 0.80 |
| 13 | STATP1 | F221/R472 | 386.0 | 0.45 |
| 14 | RBFOX1-1 | F201/R455 | 388.9 | 1.30 |

TABLE 11

| Group D | Marker | Primer | 2800 M Size | (uM) |
|---|---|---|---|---|
| 1 | NELFA | F203/R324 | 254.4 | 0.25 |
| 2 | ZC3H7B | F213/R357 | 277.2 | 0.34 |
| 3 | EDAR | F230/R395 | 300.0 | 0.15 |
| 4 | KANK1 | F172/R347 | 310.8 | 0.25 |
| 5 | RBFOX1 | F228/R416 | 324.7 | 0.27 |
| 6 | PFKP | F199/R391 | 327.3 | 0.60 |
| 7 | LPPR1 | F228/R421 | 331.5 | 0.31 |

TABLE 11-continued

| Group D | Marker | Primer | 2800 M Size | (uM) |
|---|---|---|---|---|
| 8 | CYYR1 | F228/R431 | 340.0 | 0.55 |
| 9 | HRH4 | F202/R416 | 350.4 | 1.80 |
| 10 | LOC28716 | F225/R451 | 361.7 | 0.27 |
| 11 | D12S290 | F222/R453 | 366.5 | 0.45 |
| 12 | TENM4 | F222/R458 | 371.2 | 0.38 |
| 13 | CNTN5 | F228/R481 | 385.9 | 0.70 |
| 14 | CEP104 | F230/R492 | 396.7 | 0.29 |

3. Generating NGS Library and Running NGS

The multiplex PCR system capable of simultaneously amplifying the 56 microhaplotypes was established, and the final PCR conditions for generating the NGS runnable library in the MiSeq™ system (Illumina) are set as Tables 8 and 9 based on the system. The primary PCR is a process for amplifying a microhaplotype specific sequence, and the secondary PCR is a process for attaching MiSeq™ (Illumina) adapter sequences to bar codes.

TABLE 12

1st PCR mixture

| Reagent | μl |
|---|---|
| H₂O | 2.07 |
| Gold STR buffer (10x) | 2.00 |
| Group A (6x) | 3.33 |
| Group B (6x) | 3.33 |
| Group C (6x) | 3.33 |
| Group D (6x) | 3.33 |
| Gold Taq (5.0 U/ul) | 1.60 |
| DNA template (1 ng/ul) | 1.00 |
| Total | 20.00 |

Thermal cycling

| | | |
|---|---|---|
| 95° C. | 11 min | |
| 94° C. | 20 sec | |
| 59° C. | 60 sec | x26 cycles |
| 72° C. | 45 sec | |
| 72° C. | 5 min | |
| 4° C. | forever | |

TABLE 13

2nd PCR mixture

| Reagent | μl |
|---|---|
| H₂O | 12.30 |
| Gold STR buffer (10x) | 2.00 |
| Index 1 (i7) | 2.00 |
| Index 2 (i5) | 2.00 |
| Gold Taq (5.0 U/ul) | 0.70 |
| DNA template (1/10 diluted) | 1.00 |
| Total | 20.00 |

Thermal cycling

| | | |
|---|---|---|
| 95° C. | 15 min | |
| 94° C. | 20 sec | |
| 61° C. | 30 sec | x15 cycles |
| 72° C. | 45 sec | |
| 72° C. | 5 min | |
| 4° C. | forever | |

Generating NGS Library from Samples Having Genes Mixed from Different Species

Figure 6:
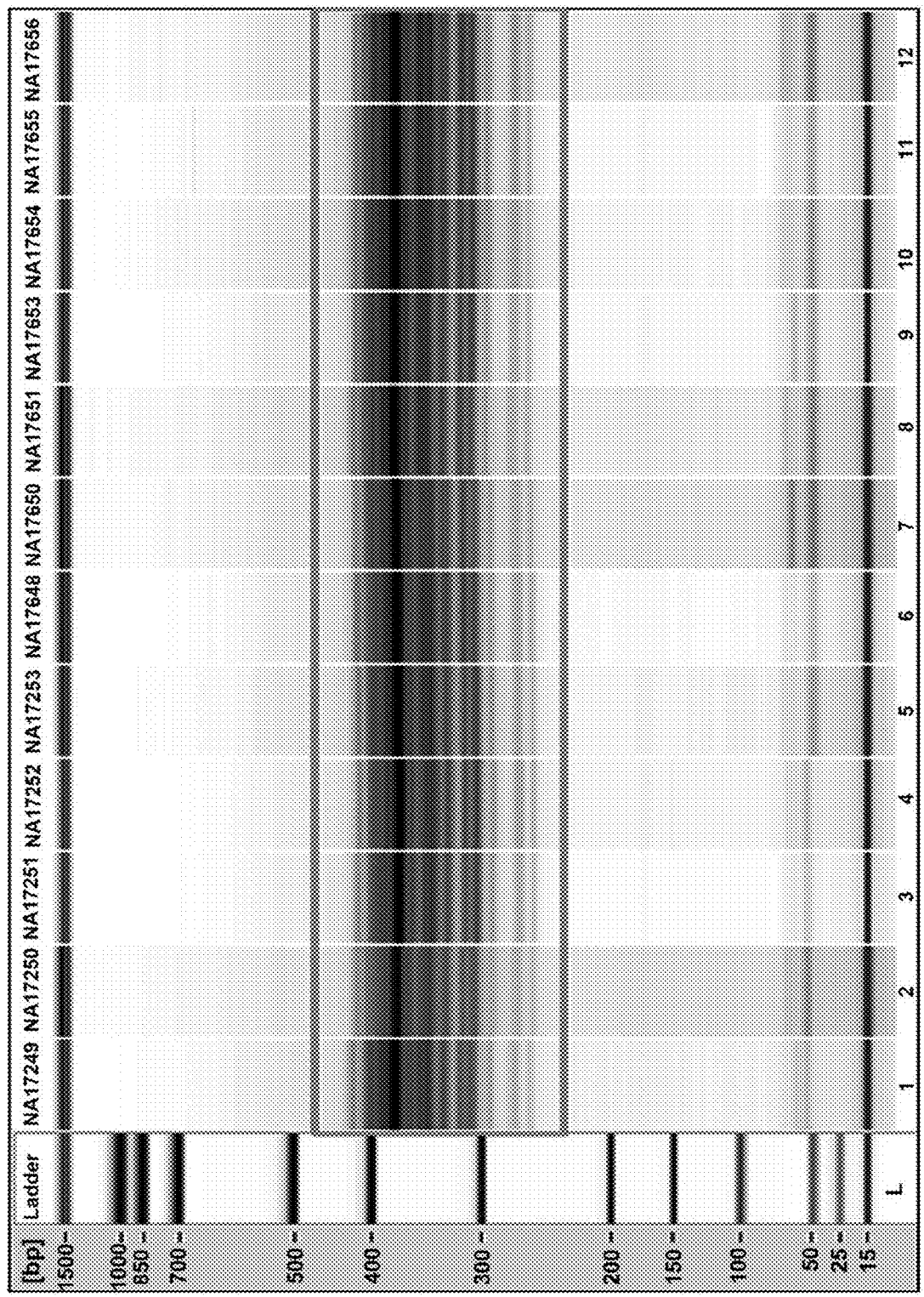
FIG. 6 is a result of electrophoresis for a generated library by using a Agilent™ DNA 1000 Kit on a Bioanalyzer.
Figure 7A:
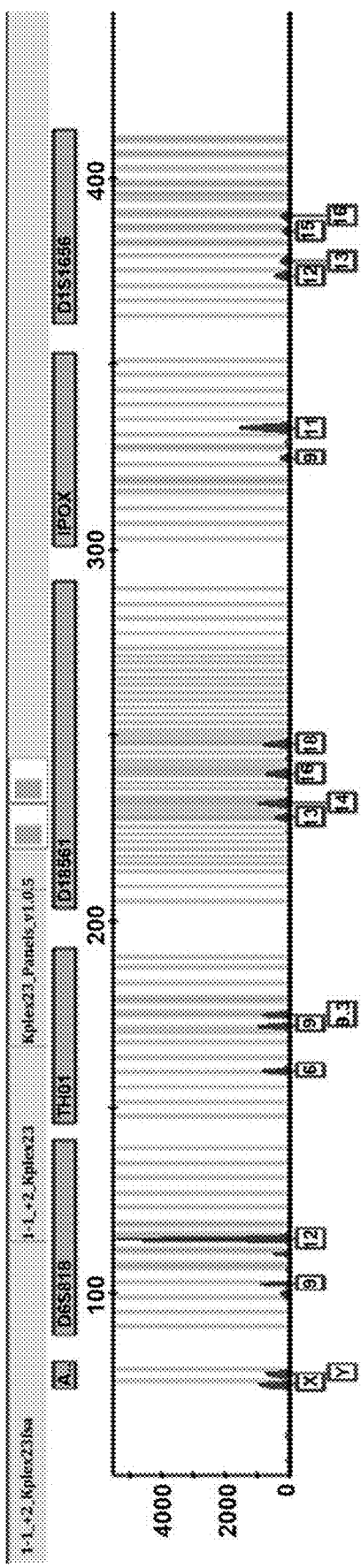
FIGS. 7A-7D show a genotype of a 1:1 mixed sample analyzed by an EzWay™ Kplex-23 PCR Kit.
Figure 7B:
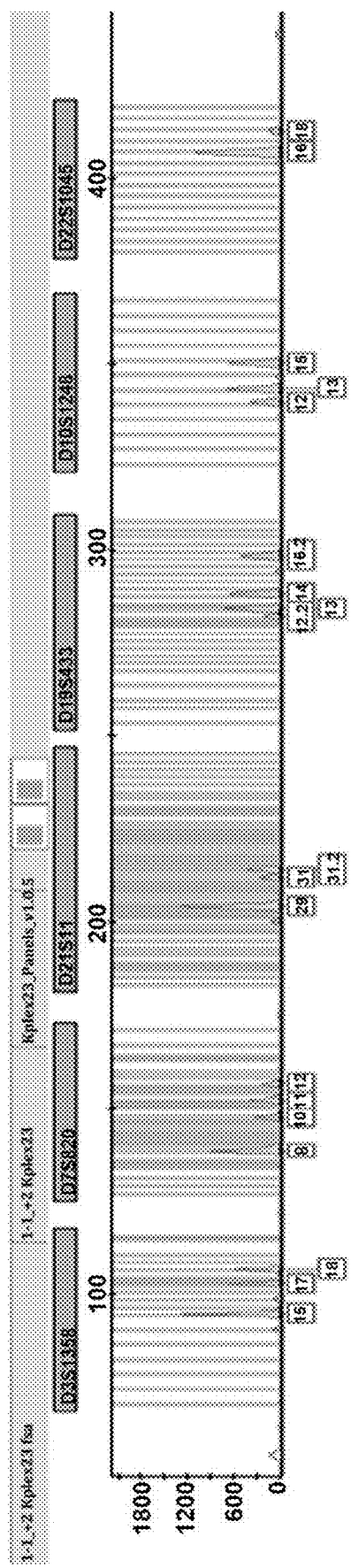
Figure 7C:
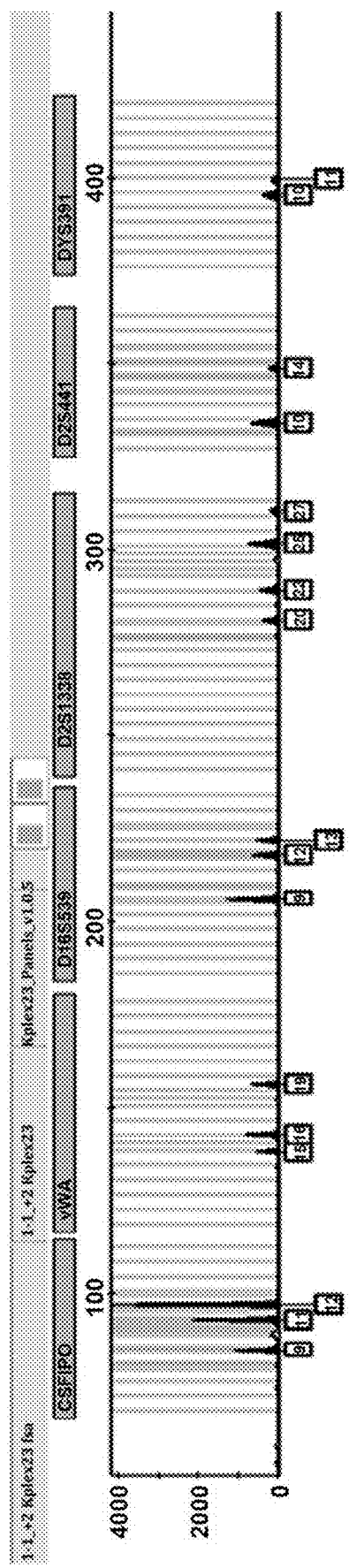
Figure 7D:
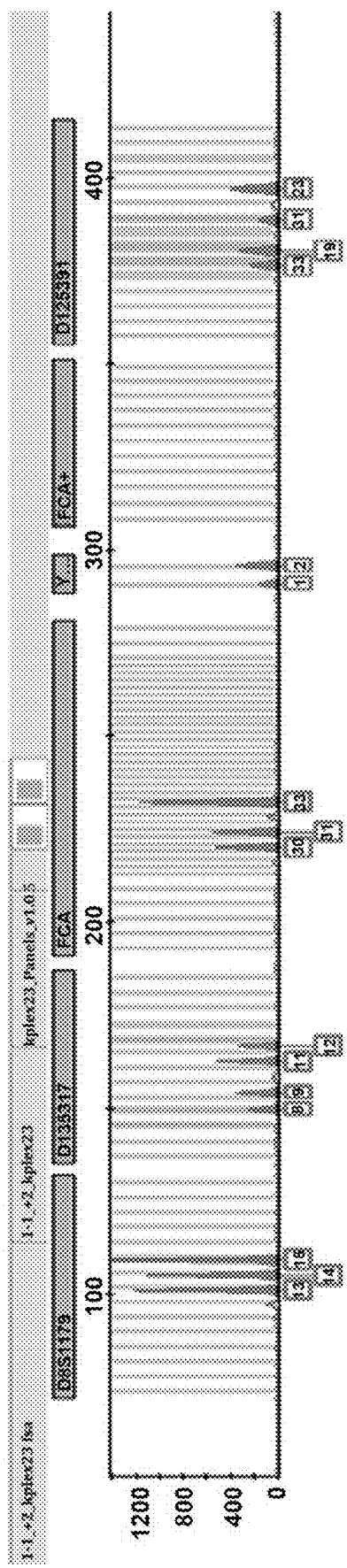

After the NGS library was generated through the primary and secondary PCRs subject to 2800M Control DNA (Promega) and 206 samples of Korean and foreigners, a size and a concentration for each library fragment was confirmed through electrophoresis using an Agilent™ DNA 1000 Kit (Agilent Technologies, Inc., Santa Clara, Calif., USA) on a Bioanalyzer (FIG. 6).

Generating NGS Library from Samples Mixed at Predetermined Ratio

After DNAs mixed at the ratio of 1:1, 1:3, 1:6, 1:9, 1:14, 1:19, 1:29, 1:49, and 1:99 were prepared, the NGS library was generated and confirmed in the same manner. In order to prepare DNAs having an accurate concentration during preparing the mixed DNAs, the DNAs were mixed after quantified by a Quantifiler® Trio DNA Quantification kit (Thermo Fisher Scientific, Waltham, Mass., USA), and a mixed state was confirmed by using an EzWay™ Kplex-23 PCR Kit (Komabiotech, Seoul, Korea) (FIG. 7).

Generating NGS Library from Degraded Samples

Figure 8:
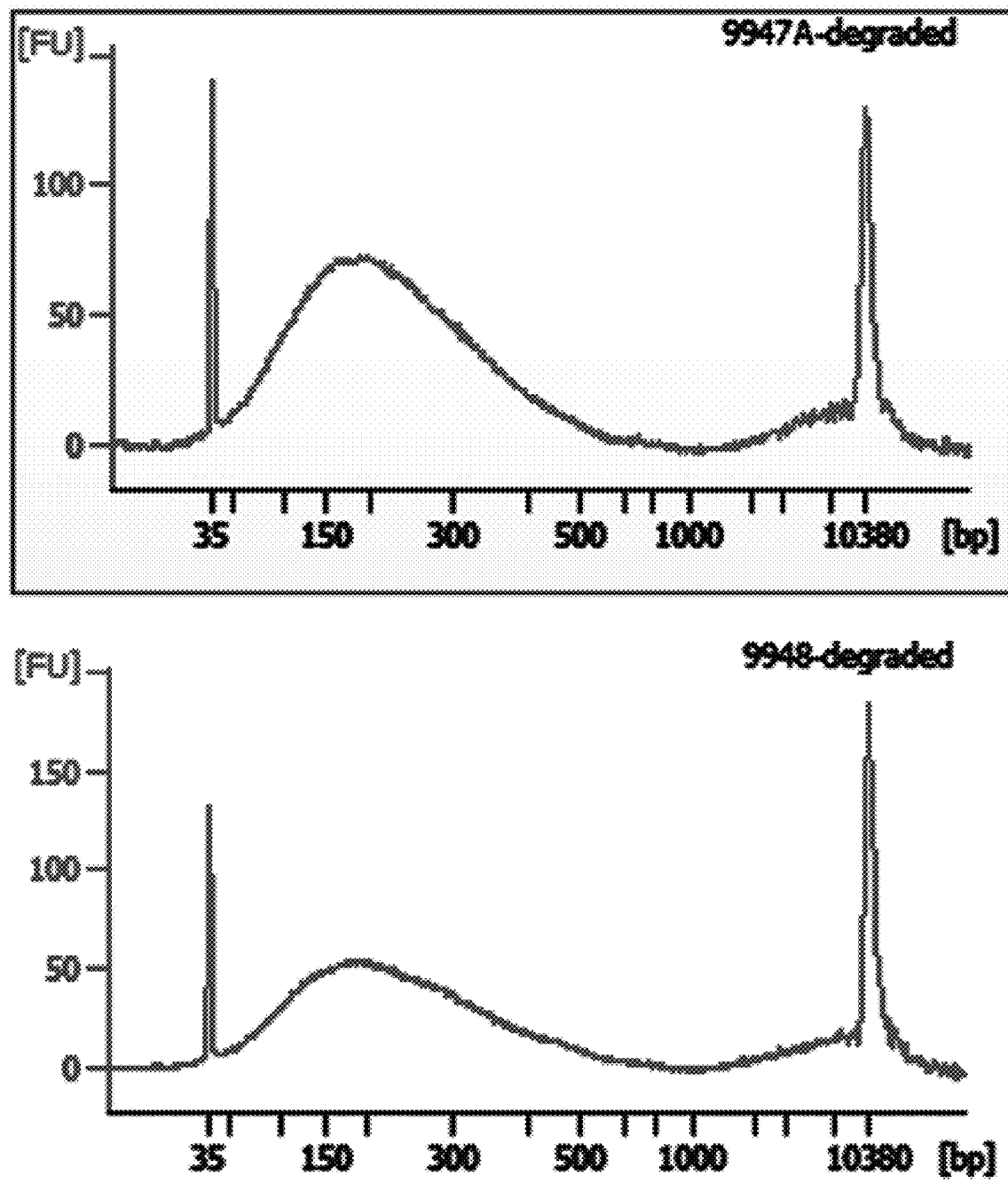
FIG. 8 shows images, of artificially degraded 9947A and 9948 standard DNAs, identified by a Bioanalyzer.

Subject to 9947A and 9948 standard DNAs (FIG. 8) artificially degraded to allow sizes of DNA fragments to be distributed within a range of 150 bp to 250 bp, the NGS library was generated in the same manner.

Purifying NGS Library

Figure 9:
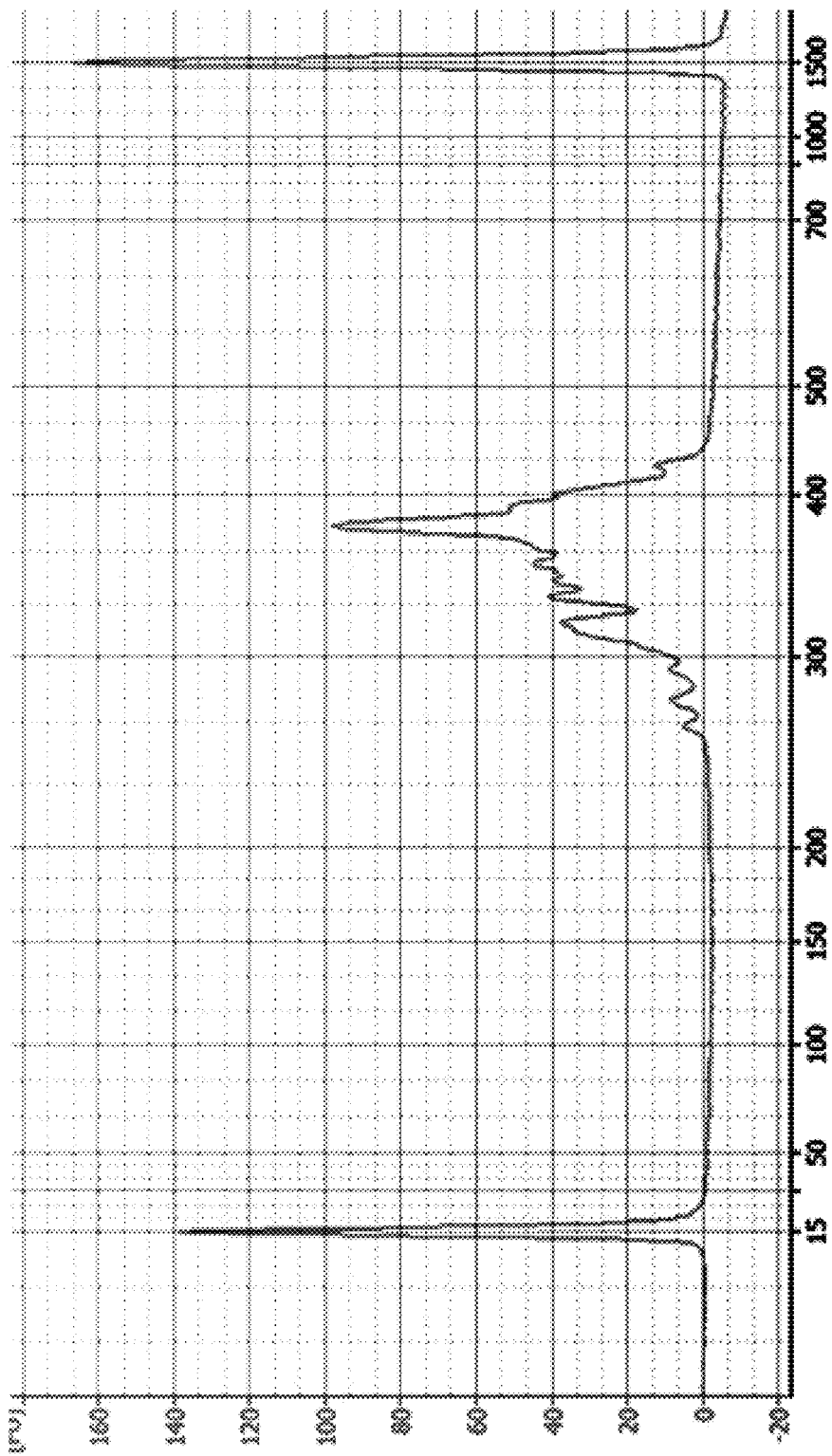
FIG. 9 shows a size and a distribution of a purified library fragment identified by using a Agilent™ DNA 100 Kit on a Bioanalyzer.

Each library was standardized to have a concentration of 10 ng/μl based on the concentration confirmed by the Agilent™ DNA 1000 kit on a Bioanalyzer. After the standardized libraries were pooled in units of 30 to 40, the purification was performed by using 1.1× Agencourt® AMPure® XP beads (Beckman Coulter, Indianapolis, Ind., USA). The sizes and distributions of the purified library fragments were confirmed through the electrophoresis using the Agilent™ DNA 1000 Kit on a Bioanalyzer (FIG. 9) and quantified by using a KAPA® Library Quantification Kit (Kapa Biosystems, Wilmington, Mass., USA).

Performing NGS Run

Primarily pooled NGS libraries were quantified at the same concentration of 10 nM, and finally pooled into one tube, and an NGS run was performed at 2×300 bp in the Miseq™ system by using a Miseq™ Reagent Kit v3 (Illumina).

Figure 10:
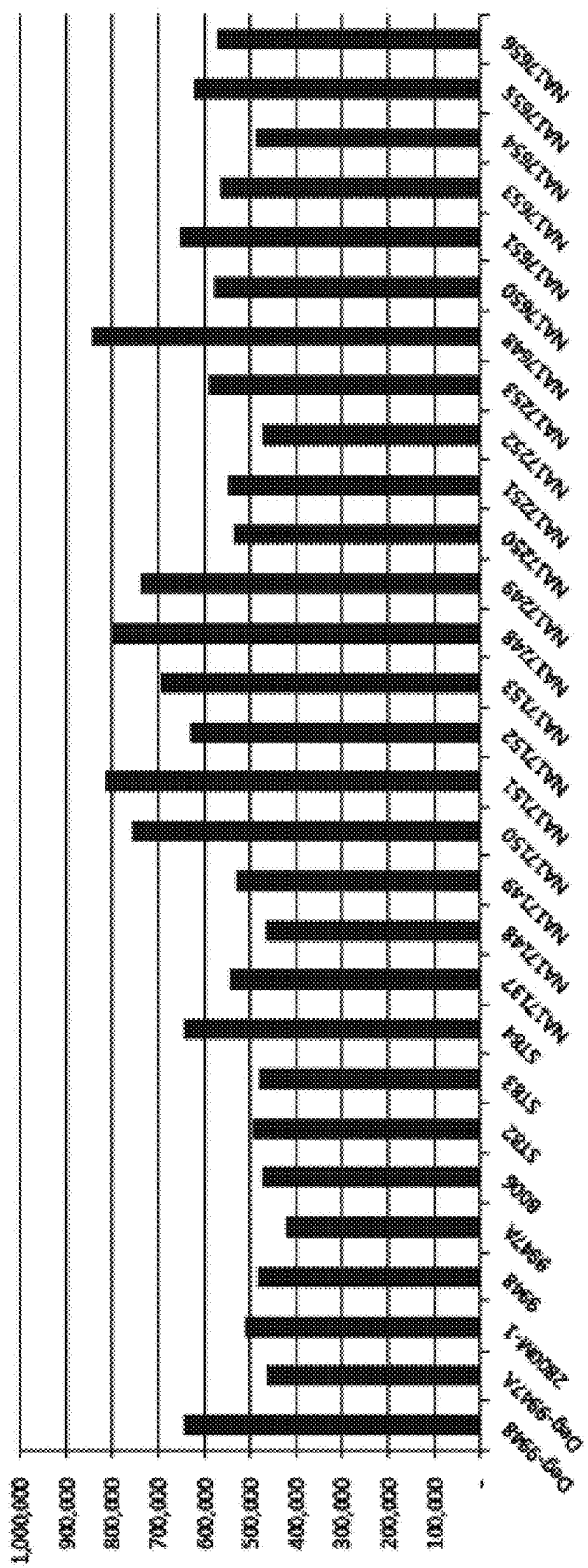
FIG. 10 shows an example of read counts for each sample obtained after performing an NGS.

Further, 13.0 GB sequence data was acquired as one of results obtained by performing the NGS and about 400,000 to about 800,000 read counts were found for each sample, in which relatively uniform read counts about 600,000 on average were obtained (Table 14 and FIG. 10).

TABLE 14

| | Yield | Read |
|---|---|---|
| Total | 13,434,390,434 | 52,167,804 |
| Undetermined | 1,388,721,676 | 4,925,702 |
| Ratio | 10.34% | 9.44% |

Analyzing NGS Results

For NGS data analysis, a haplotype sequence for each marker was extracted using a STRait Razor v3.0, and SNPs and haplotypes were analyzed with the help of a bioinformatics expert of Macrogen.

Figure 11:
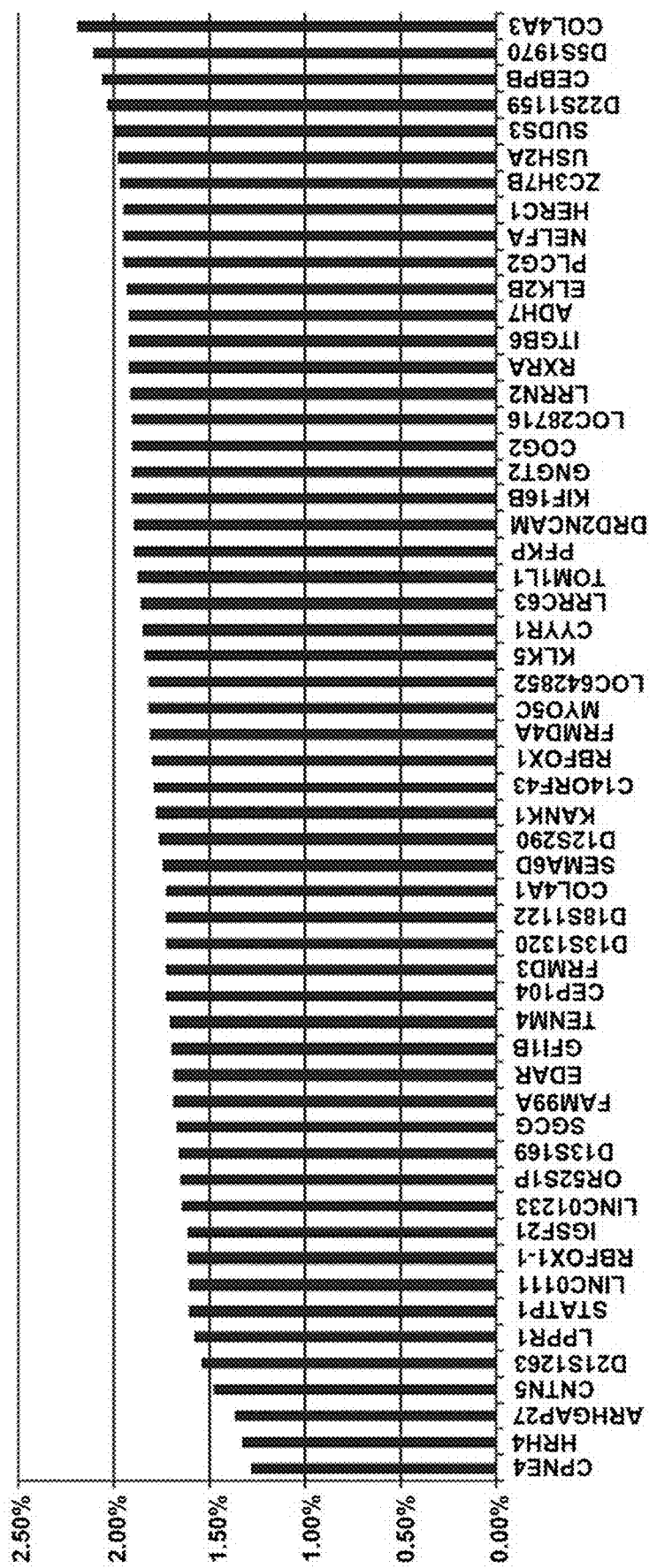
FIG. 11 shows an average read rate obtained for each microhaplotype.

It was represented that CPNE4 was the minimum and COL4A3 was the maximum among confirmed results of the relative average read rate obtained for each microhaplotype, and the coverage difference between the microhaplotypes was relatively uniform within the range of two times (FIG. 11).

Table 15 shows haplotype sequences of 56 microhaplotypes extracted from the 2800M ControlDNA using the STRait Razor v3.0.

TABLE 15

| Marker | Length | Allele Sequence | Read #1 | Read #2 |
|---|---|---|---|---|
| KLK5 | 75 | TTGATCTTAAGGATGATGACCCCCCGCCGAGGAGAACCAAGCGAAACACAGCCTGACG CCCTGTGTCTGGAGCTG (SEQ ID NO: 113) | 3385 | 3090 |
| USH2A | 83 | TTTCAACTATTATTATTATTACCCAGTTAGAAAGTGAATAAATGACCTAAATGGGAAA CCTGACATAGGTAGACATATTGGCT (SEQ ID NO: 114) | 2264 | 2115 |
|  | 83 | TTTCAACTATTATTATTATTACCCAGTTAGAAAGTGAATAAATGACCTAAATGAGAAA CCTGACATAGGTAGACATATTGGCT (SEQ ID NO: 171) | 1974 | 1822 |
| D13S1320 | 129 | GTATAAATTCATACACATTATGTGGTTCTGGTGTCTGCCATCTGCAGCACATAAGCAA ATTCCCCTAATTACTGACATCTCTCTACGAAGGCCCATA (SEQ ID NO: 115) | 1626 | 1471 |
|  | 129 | ATATAAATTCATACACATTATGTGGTTCTGGTGTCTGCCATCTGCAGCACATAAGCAA CTTCCCCTAATTACTGACATCTCTCTACGAAGGCCCATG (SEQ ID NO: 172) | 1400 | 1268 |
| SEMA6D | 132 | CTCTCCCTTATTTAAGAAGGGATATCCTGGCTCCTCAGCCTGCCATCTGGGGTTCTCT ACATTTTCACATCTTTTCCATAACTAGCCTTTACACTCTTC (SEQ ID NO: 116) | 1620 | 1380 |
|  | 137 | CTCTCCCGTATTTAAGAAGGGATATCCTGGCTCCTCAGCCTGCCATCTGGGGTTCTCT ACATTTTCACATCTTTTCCATAACTAGCCTTTACACTCTTC (SEQ ID NO: 173) | 1460 | 1270 |
| MYO5C:-1 | 132 | GTTACTTTTTGAGAACATTTAAAAATAAATACATTGAAATGCTGATTAGAGAGCGAAA GTAATTTAGGTTGCTTTTTCAATCTGAGGTTTTTTTAAAAA (SEQ ID NO: 117) | 2069 | 1938 |
| MYO5C | 137 | GTTACTTTTTGAGAAATTTAAAAATAAATACATTGAAATGCTGATTAGAGAGCGAAA GTAATTTAGGTTGCTTTTTCAATCTGAGGTTTTTTTAAAAA (SEQ ID NO: 118) | 1232 | 1123 |
| TOM1L1 | 146 | TCCGACGGCCCCACTGCGTTTCTCCCCTTTAATGTTTAATGCGATGATGACTATTGCT GATCAGGACTAAATTTTACCCCTAGGATGCCCAGGGAATA (SEQ ID NO: 119) | 1720 | 1157 |
|  | 146 | TCCGACGGCCCCATTGCGTTTCTCCCCTTTAATGTTTAATGCGATGATGACTATTGCT GATCAGGACTAAATTTTACCCTAGGATGCCCAGGGAATAA (SEQ ID NO: 174) | 1529 | 1060 |
| HERC1 | 155 | ACTTCTTCCATGAAGCTTTTCATGTTGTAATCACCCTACGCTCACCAACACAGATTTA ATCACTTCCTCCTCTAACTCTCTTACTTTTGCTTACACACA (SEQ ID NO: 120) | 2172 | 1588 |
|  | 155 | ACCTCTTCCATGAAGCTTTTCATGTTGTAATCACCCTACGCTCACCAACACAGATTTA ATCACTTCCTCCTCTAACTCTCTTACTTTTGCTTACACACA (SEQ ID NO: 175) | 1998 | 1470 |
| DRD2NCAM | 164 | GCCCTTGCCCCTCGCTTATCTTCTCCCAGATACATAAGACCACTTATTGCCAATTACT GTGCTAGAAGAAAGACAGCCAACTTATACGGAGGGCCT (SEQ ID NO: 121) | 3141 | 2185 |
| ELK2B | 157 | TGAAAGTTACAAGTACAATTTTTTAAACTAGTAAAAGAAGATGTAATCTATTCAATGG AAAACAGGAAATGTGGAAGAAACAAACAAAAAATAACT (SEQ ID NO: 122) | 1391 | 1159 |
| ELK2B | 157 | TGAAAGTTACAAGTACAATTTTTTAAACTAGTAAAAGAAGATGTAATCTATTCAATGG AAAACAGGAAATGTGGAAGAAACAAACAAAAAATAACT (SEQ ID NO: 122) | 1265 | 1017 |
| CEBPB | 185 | CTGGTGCACAACACATGCTAGCTATTTTCATTCTTACTAGTGGCATAGTAGAAAGCAC TGGAATTTTAGCTTCAGACAGACCTGGGTGTACATTTCAG (SEQ ID NO: 123) | 1935 | 1378 |
| CEBPB | 185 | CTGGTGCACAACACATGCTAGCTATTTTCATTCTTACTAGTGGCATAGTAGAAAGCAC TGGAATTTTAGCTTCAGACAGACCTGGGTGTACATTTCAG (SEQ ID NO: 176) | 1808 | 1284 |
| FRMD3 | 176 | GAATCATATATATCTTTGAAAGTAAGGACAGAGAATGTAAATCAGGCAATAAATGACT GAAGACAAATGGGCAGGGACCGAGGGATATAGCATGT (SEQ ID NO: 124) | 1821 | 1139 |
| FRMD3 | 176 | GAATCATATATATCTTTGAAAATAAGAACAGAGAGTGTAAATCAGGCAATAAATGACT GAAGACAAATGGGCAGGGACCGAGGGATATAGCATTT (SEQ ID NO: 177) | 1759 | 1071 |
| LINC01233 | 196 | AACATTCTCTATCATGTGGCCTGGCACAAGGATTGGCAGCAACAGAGCAGACAGAACC AAAGGAAGAAGGGCCTGAAAAACCTGCTAGTGCATT (SEQ ID NO: 125) | 2998 | 1069 |
| STATP1 | 212 | ATAAGCACTGCACTTTACCAAGTTGATGGATGCAGGTTCTTTATTTCAGCCAGTAACA GGTAAAAGTTAGAGGTTCAACTATTGTGTAGGGAAGTTAT (SEQ ID NO: 126) | 3323 | 1563 |
| RBFOX1-1 | 213 | TGTTGCGTGTGCTAATAGTTGATTGTCTTAGATTGCTGAGTAGTATTCTATGGTGTCA ATCTACCACCCAAGAATCTTTTTTCAGTAGACACCCTGAGG (SEQ ID NO: 127) | 1144 | 537 |
| RBFOX1-1 | 213 | TGTTGCGTGTGCTAATAGTTGATTGTCTTAGATTGCTGAGTAGTATTCTATGGTGTCA ATCTACCACCCAAGAATCTTTTTTCAGTAGACACCCTGAGG (SEQ ID NO: 178) | 1100 | 505 |
| NELFA | 79 | GGAGCGATGCTTTTTCTTACCACGAAGCGTTGATATAAAGGAAGATGCTCATGTTAAG AACACAGAACACGCAGCGGC (SEQ ID NO: 128) | 1879 | 1704 |
|  | 79 | GGAGCGATGCTTTTTCTTACCCAGAAGCATTGATATAAAGGAAGATGCTCATGTTAAG AACACAGAACACGCAGCGGC (SEQ ID NO: 179) | 1855 | 1647 |
| ZC3H7B | 104 | CTTTCATTCATTCCATAAGGAGGCCCACAAAAACACTCTCGGCCCTGGGCCTGAGAGAG CTGCGTCCTTGCCCTCAGGGACCTCCCAGCCTGCAAA (SEQ ID NO: 129) | 4325 | 3848 |
| EDAR | 125 | TATCCAAAAGGGGTGAAAGAATCACTGAGTTAGAGAAGGCTTCAGGAGAATCCAGAG TTCAATCTGGGTCATAAGAACATACAACTCAGATTTC (SEQ ID NO: 130) | 3276 | 2881 |

TABLE 15-continued

| Marker | Length | Allele Sequence | Read #1 | Read #2 |
|---|---|---|---|---|
| KANK1 | 138 | ACATTCTAGGGACAGTTAAAGTCTCCTGTGTACACGGTTGCCAGAAGAAAAAATACTA AGCACGTGTTCATCGTTTATCTAAAATTCGGTTTAATGG (SEQ ID NO: 131) | 3609 | 2771 |
| RBFOX1 | 148 | GTATTTGGAATTAACGCAGGAGCTAGAGACTAAGCAAACCCCGCCTCCACCCCAGTGC AGATTTCAGTTGAATGCAGACTAGAGCCTTTGAAAAT (SEQ ID NO: 132) | 3417 | 2595 |
| PFKP | 152 | AAAGTATGTTTTAAGACTCTGAAAATTTTTGAACTCACTCCCAGAAAGTTTTACCACC TCTTCTTCTGTGTGGCCACCAGGGGACGTAGTGTGGCCG (SEQ ID NO: 133) | 3470 | 2348 |
| LPPR1 | 155 | GCTCTGAACAATTGGGTATTCTTTTTTCTTAGAGCCCAGATGCATTTTTTGAAAGTC GTTCCAGGGGCCTGAGATGAAGTGGGGGTGTGAGAAGTAA (SEQ ID NO: 134) | 1457 | 946 |
|  | 155 | GCTCTGAACAATTGGGTATTCTTTTTTCTTAGAGCCCAGATGCATTTTTTTGAAAGTC GTTCCAGGGGCCTGAGATGAAGTGGGGGTGTGAGAAGTAA (SEQ ID NO: 134) | 1391 | 937 |
| CYYR1 | 162 | GAGAGTGCTCTTCCCTGAATCCCTCACGTCATATTGTTAGTGCCTCTTCTGCTTATTC ACAAGACCAGTCATCGTAGAGGTTGGATTTGAATCTTGTAT (SEQ ID NO: 135) | 2005 | 1366 |
|  | 162 | GAAAGTGCTCTTCCCTGAATCCCTCACGTCATATTGTTAGTGCCTCTTCTGCTTATTC ACAAGACCAGTCATCGTAGAGGTTGGATTTGAATCTTGTAT (SEQ ID NO: 180) | 1528 | 1105 |
| HRH4 | 172 | TCACATCATGACGTCTACTGGGCAGTGAACTTTAGCTACATATGAATACCCAGCCAGA TTCCAAGATTGTGGAAACCAAGATGGCAGCCTAGGAA (SEQ ID NO: 136) | 2454 | 1595 |
| LOC28716 | 186 | GAGCACGTCGCGTTCTGGAACCTCATTGTCTCACCCTTGTCAAACCATGGGCAGTGCC ATTTACTGTGCAGGCTTCAGAGGATTAACTGAGGCAGT (SEQ ID NO: 137) | 3808 | 2204 |
| D12S290 | 189 | GTACAAAATTCTATTGTTGGTCTTAACTCACTGCTTTCTATCGTTTATGTTGCTGTGT TTTCTGTTACTATGTAAGTTTCTTTGAGGCATGCACCATCTATT (SEQ ID NO: 138) | 1664 | 1091 |
|  | 189 | GTACAAACTTCTATTGTTGGTCTTAACTCACTGCTTTCTATCGTTTATGTTGCTGTGT TTTCTGTTACTATGTAAGTTTCTTTGAGGCATGCACCATCTATT (SEQ ID NO: 181) | 1463 | 1009 |
| TENM4 | 195 | GTGCTCGCTTTGTTGTGCTTGTGTCGGATGGTGAGCGAACCCTCAGAACACAACTGTA CAGCAGGACTTGGCTCACTGGACTCTCATTATCTGGCCA (SEQ ID NO: 139) | 1593 | 727 |
|  | 195 | GTGCTCCCTTTGTTGTGCTTGTGTCGGATGGTGAGCGAACCCTCAGAACACAACTCTA CAGCAGGACTTGGCTCACTGGACTCTCATTATCTGGCCA (SEQ ID NO: 182) | 1482 | 722 |
| CNTN5:-1 | 208 | TTGGGTAACACAGCAAAGTGTAAAAAAAAAATGGAGGGGGATTAATTAGTTGGAAAGA AAAGACTGGTTTAGACATATGGAAGGTTATTATCAAGA (SEQ ID NO: 140) | 1659 | 499 |
| CNTN5:-2 | 207 | TTGGGTAACACAGCAAAGTGTAAAAAAAAATGGAGGGGGATTAATTAGTTGGAAAGAA AAGACTGGTTTAGACATATGGAAGGTTATTATCAAGAG (SEQ ID NO: 141) | 491 | 2145 |
| CEP104 | 222 | ACGGCTGAGGTGCAGCAGGCATGCAGTGATACTTGCTGAATGGACAGAAGCCGTTCCC ACATGGAGCTTCCATGACATGCATTTACACACCCCGA (SEQ ID NO: 142) | 1461 | 540 |
|  | 222 | ACGGCTGAGGTGCAGCAGGCGTGCAGTGATACTTGCTGAATGGACAGAAGCCGTTCCC ACATGGAGCTTCCATGACATGCATTTACACACCCCGA (SEQ ID NO: 183) | 1257 | 2967 |
| COG2 | 112 | TGGTATGAAGTACCTATTAAACGTTATTTCTGAATGCTATATGTATTTGATGTTTATC CAAACACCTGGGAGATAGTGTCATGTAAAATTGTGCGTGGC (SEQ ID NO: 143) | 3584 | 841 |
| ITGB6 | 118 | ACCCTCTCTACCTAAGGATGGGCAATGGCTTATGAGTGAGAAACATGGAGCCGTGGGA ACTCAGAATGACATGTACCTGGAGATTGTGGTAACG (SEQ ID NO: 144) | 1885 | 1548 |
|  | 118 | ACCCTCACTACCTAAGGATGGGCAATGGCTCATGAGTGAGAAACATGGAGCCGTGGGA ACTCAGAATGACATGCTACCTGGAGATTGTGGTAACG (SEQ ID NO: 184) | 1833 | 1222 |
| D18S1122 | 127 | GAACTGGAGAGCAGGTGGATTAAATCTGGGGGGTGACTCCAGCACATCTCTAATGAAC ACTTCTTAACATTTAATTTCAAAGGGCCTGGTGACCCT (SEQ ID NO: 145) | 3164 | 903 |
| GFI1B | 155 | CGGGGTCTCCTCCTGGCCTCTTCTTGCCGCCGCCTGCTCTGGGCAGAGCCCGGGAGTG TGAGCCGCCAGAAGCAGCGGCACGTGGCTGTCTCTCT (SEQ ID NO: 146) | 1836 | 1045 |
|  | 155 | CGGGGTCTCCTCCTGGCCTCTTCTTGCCGCCGCCTGCTCTGGGCAGAGCCCGGGAGTG TGAGCCGCCAGAAGCAGCGGCACGTGGCTGTCVTCTC (SEQ ID NO: 185) | 1768 | 1608 |
| D21S1263 | 158 | GACCTATAGGGTAGGTTTTCAGGAGGGCTTAGCTGACTTCAGCTGAAATGCTCAGGT TGGGGCAGGGTGTTGGAGGTGTGAGAAAGCCTTCAGCT (SEQ ID NO: 147) | 1666 | 696 |
|  | 158 | GACCTATAGGGTAGGTTTTCAGGAGGGCTTAGCTGACTTCAGCTGAAATGCTCAGGT TGGGGCAGGGTGTTGGAGGTGTGCGAAAGCCTTCAGCT (SEQ ID NO: 186) | 923 | 1227 |
| D5S1970 | 168 | CTTGATTTTCTTAACAAAACTGAAGGCCACAGTTGAAGAGAGAGAGCATGAGACAGCT TGATCGAAATGGTGAAGCTTTGGAGAGATTTTGCGGGG (SEQ ID NO: 148) | 2293 | 1171 |
|  | 168 | CTTGATTTTCTTAACAAAACTGAAGGCCACAGTTGAAGAGAGAGAGCATGAGACAGCT TGATCGAAATGGTGAAGCTTTGGAGAGATTTTGCGGGG (SEQ ID NO: 148) | 2125 | 2450 |
| LOC642852 | 182 | GGGCGAGCAGGGGTCATGGATGGGGCTCACTGGGACTGTGAGAATCTGTCCCGCAGG ACTTTCTGGGATGGAAACGCTGGCAGAGGTGAAGCC (SEQ ID NO: 149) | 1692 | 420 |
|  | 182 | GGGCGAGCAGGGGTCATGGATGGGGCTCACTGGGACTGTGAGAATCTGTCCCGCAGG ACTTTCTGGGATGGAAACGCTGGCAGAGGTGAAGCC (SEQ ID NO: 149) | 1301 | 2362 |

TABLE 15-continued

| Marker | Length | Allele Sequence | Read #1 | Read #2 |
|---|---|---|---|---|
| COL4A1 | 185 | GTTTTCTGTTTCAGCTGGCTTTTGCGGGAAAGGGAAGCCCTGGGGCTAGGAGAGCAGT CCTTGCCCTGTGGGAAGGGTCCCAGGTGGCACTGCCCC (SEQ ID NO: 150) | 1513 | 670 |
| | 185 | GTTTTCTGTTTCAGCTGGCTTTTGCGGGAAAGGGAAGCCCTGGGGCTAGGAGAGCAGT CCTTGCCCTGTGGGAAGGGTCCCAGGTGGCACTGCCCC (SEQ ID NO: 150) | 1259 | 2044 |
| IGSF21 | 187 | CCAGTTCTCATGAATCTGAGGAATTCTTCCTCCTAGCTACTTCCTTCCTTTTCCCTCA TTACATCCCTGCCAAGGACAAATTCTGCCATTTGCATGGC (SEQ ID NO: 151) | 1644 | 1041 |
| | 187 | CCAGTTCTCATGAATCTGAGGAATTCTTCCTCCTAGCTACTTCCTCCTTTTCCCTCA TTACATCCCTGCCAAGGACAAATTCTGCCATTTGCATGGC (SEQ ID NO: 187) | 1598 | 1961 |
| RXRA | 195 | GTCACGAATGCGGCTCAGGAGGCCCAAGTGTGCACAGTGAGCTCACACCCACTTCCAG CCAACAACCCTCTTGCCTGGTGAAACTTCCCCTGGGC (SEQ ID NO: 152) | 4058 | 1942 |
| SGCG:1 | 195 | CTTCAGTTGTCAAGGTATTGGGTACAGGGGTCAGAAAGAAACATGACTCCATGGACCA CTGCTTGGCCCAAGACCAGATGTCAAAACCACAGAGC (SEQ ID NO: 153) | 3224 | 1978 |
| LINC0111 | 201 | CAACCTTTCCTGTGGGCTAAGGTAGGAAAGCAGAAAACAGTTAGTGTGAGATTCTTGG TGTCCTCAAGAGCAGCCTGTGTAACAGAAAAGACCGTT (SEQ ID NO: 154) | 3142 | 1929 |
| LRRN2 | 206 | TTGCCGAAGAAAACACGGAAGCCGCCAGCACTATTATGCATTCATGATTCCAGCTTCA ACCAGTCCTCTCTGCTGCAATCCCTTTATTCCTCCCTCTG (SEQ ID NO: 155) | 3361 | 247 |
| CPNE4:-1 | 196 | ACAAATAGTCATCATCATTCCTATTTTACAGATGGGTAAATTAAGATTCAAAGAATCT TTTTTGTTTTCTCGTTTGTTTTTTGGTTGGTTTTGTTTTGCTTTT (SEQ ID NO: 156) | 920 | 631 |
| CPNE4 | 203 | ACAAATAGTCATCATCATTCCTATTTTACAGATGGGTAAATTAAGATTCAAAGAATCT TTTTTGTTTTCTCGTTTGTTTTTTGGTTGGTTTTGTTTTGCTTTT (SEQ ID NO: 157) | 754 | 496 |
| GNGT2 | 117 | GACCCGCTGGAGGAGCAAAAGTTAAGGGACCAATATGGTCAATGGGAGGTCCTCTTAT TCTCCTGTCTCTAGGATGACAGGCTTGGTGGTGGGAGG (SEQ ID NO: 188) | 4222 | 3523 |
| COL4A3 | 126 | TAGGTTTCTCATCTATTAGATGGAGCTTATAACAGTACCTCCCTTACAGAATTGTTGT AAGATATAATGAGATAATATGAGACAGCCAGCACTGAAA (SEQ ID NO: 158) | 2607 | 2245 |
| | 126 | TAGGTTTCTCATCTAGTAGATGGAGCTTATAATAGTACCTCCCTTACAGAATTGTTGT AAGATATAATGAGATAATATGAGACAGCCAGCACTGAAA (SEQ ID NO: 189) | 2100 | 1793 |
| SUDS3 | 137 | TCATTTAAAAATCTGGTAGCCTGGTGGAAGGGAGGTAGCAGAACCAATGCTGATTGGG ACAGGAGATTATTTCACAAATAATTCATAACCTAGGTTT (SEQ ID NO: 159) | 3790 | 2885 |
| D13S169 | 148 | TTTCCAAGTTGTTCTAGTGAATTACTGAACTGGATAGGATTGTGGAAACCTGTGAATA ATAGCTAGGTAGTCAGAAGACATGGTGCGCTGGGGATCC (SEQ ID NO: 160) | 1470 | 1182 |
| | 148 | TTTCCAAGTTGTTCTAGTGAATTACTGAACTGGATAGGATTGTGGAAACCTGTGAATA ATAGCTAGGTAGTCAGAAGACATGGTGCGCTGGGGATCC (SEQ ID NO: 160) | 1391 | 1127 |
| PLCG2 | 165 | CTTCCAGAGACATTTACATACTGGCATAACTACCATACACAAACTTCTGGACACAAAG TGATCGCATAAATCACGGGGCTTTGTGCTTTTGTTGTTG (SEQ ID NO: 161) | 2040 | 1419 |
| | 165 | CTTCCAGAGACATTTACATGCTGGCATAACTAACATACACAAACTTCTGGACACAAAG TGATCGCATAAATCACGGGGCTTTGTGCTTTTGTTGTTG (SEQ ID NO: 190) | 1991 | 1287 |
| D22S1159 | 176 | CTCCCGGAAACGTGATTAGTGAAGACACATTAACAGCGAAACTGACAGAGAACCTCAA CATTCTCTGGTAGGAAAAGCCAGGATCCTGGCAGAG (SEQ ID NO: 162) | 4320 | 1776 |
| KIF16B | 179 | TTTACTTATATCACAGAACACCAAACCCAGATTCCTCCCATTCCCACAGTGGGTCCTT TTTTCTCAATCAATCACTAACCTATGCGTCTAGAGCTTT (SEQ ID NO: 163) | 3483 | 2560 |
| ADH7 | 184 | AGAGATGAAGAAAAGGGGCAGAAGATGAACATGGGGGATCACAAAGTGAAGGCCTTCT GTGTCTCAGAGTTGCCTAAACACCCTGCTTCCATATC (SEQ ID NO: 164) | 1972 | 1301 |
| | 184 | AGAGATGAAGAAAAGGGGCAGAAGATGAACATGGGGGATCACAAAGTGAAGGCCTTCT GTGTCTCAGAGTTGCCTAAACACCCTGCTTCCATATC (SEQ ID NO: 164) | 1868 | 1196 |
| C14ORF43 | 189 | TGTTCTTAAGCGACTGGAATGCCCTCTTTAGCTGGGGGTGTTCGGCCTCCTTTTTTGG AGGTGGGTTGTGATGTCAAAACACTGGGTTGTGGTATAGGA (SEQ ID NO: 165) | 1740 | 806 |
| FAM99A | 198 | AAGACCTCGTTCCATTGCCCTAGGTCAGGCATGGATTATTAACTCTCAGGGTTTTGGG GGACCAGCAGCCACAGATGTGGAGTCCTGGGGAAAGGG (SEQ ID NO: 166) | 1532 | 570 |
| | 198 | GAGACCTCGTTCCATTGCCCTAGGTCAGGCATGGATTATTAACTCTCAGGGTTTTGGG GGACCAGCAGCCACAGATGTGGAGTCCTGGGGAAAGGG (SEQ ID NO: 191) | 1418 | 491 |
| FRMD4A | 195 | AAATAATCATTTGCTTTTTCAACAGAAGTAAAGTCACTGAAACATTTTGGAATCTAAA GTTCCAAATGGAAGTCAGGGATAGCAGATGAACCCAAA (SEQ ID NO: 167) | 1969 | 1254 |
| | 195 | AAATAATCATTTGCTTTTTCAACAAAAGTAAAGTCACTGAAACATTTTGGAATCTAAA GTTCCAAATGGAAGTCAGGGATAGCAGATGAACCCAAA (SEQ ID NO: 192) | 1464 | 933 |

TABLE 15-continued

| Marker | Length | Allele Sequence | Read #1 | Read #2 |
|---|---|---|---|---|
| OR52S1P | 196 | AAATTATTTGTCATCATCTCCTTAGAAGCCAAAGCTCCCTAATAGCTCTCTCTTCCAG ATTCAAGGTTACCATTTTCATGCCTTATTGTTTTTTCAAAC (SEQ ID NO: 168) | 2680 | 1917 |
| ARHGAP27 | 210 | GCAGCCCACACTGAAGGCTGGGTCAGTCCTGTTTCCACAGTGGGGAAGTGATCAGAGC TGCCTCATGACTGGCACAGTGCCAGCACAGGGCCAG (SEQ ID NO: 169) | 1461 | 238 |
| LRRC63 | 213 | GCCAGCTACAGACAGTTTCACAAAGTCATTATCTAATTGGAAATATCTGCTGGGACAC CAGATTTCCCACTGACATTAACTGGGCATTCTCTTAGCC (SEQ ID NO: 170) | 3949 | 1958 |

Based on the NGS analysis results of the microhaplotypes subject to the artificially degraded DNA samples, read counts were found by 50% or more on average in all markers as compared to the non-degraded DNA samples, and thus a sufficient coverage for determining a genotype was obtained. KLK5, USH2A and D13S1320, which had a relatively small amplicon, showed read counts as twice or more.

TABLE 16

| Microhaplotype | 9947A | 9948 | Average |
|---|---|---|---|
| CNTNS | 61.42% | 43.31% | 52.36% |
| LINC0111 | 48.96% | 56.89% | 52.92% |
| LRRC63 | 52.72% | 57.01% | 54.86% |
| D12S290 | 58.13% | 61.24% | 59.68% |
| CEP104 | 59.73% | 67.99% | 63.86% |
| FBMD4A | 61.40% | 66.40% | 63.90% |
| STATP1 | 72.52% | 55.67% | 64.10% |
| IGSF21 | 71.04% | 57.39% | 64.21% |
| RBFOX1-1 | 59.18% | 69.59% | 64.39% |
| LOC642852 | 69.58% | 66.17% | 67.88% |
| SGCG | 59.67% | 80.04% | 69.86% |
| RXRA | 64.57% | 76.18% | 70.38% |
| TENM4 | 75.43% | 66.18% | 70.80% |
| LRRN2 | 79.72% | 62.01% | 70.87% |
| D22S1159 | 76.23% | 66.69% | 71.46% |
| KIF16B | 69.99% | 74.58% | 72.29% |
| OR52S1P | 63.95% | 82.63% | 73.29% |
| LINC01233 | 80.90% | 67.33% | 74.12% |
| ARHGAP27 | 76.57% | 72.51% | 74.54% |
| LOC28716 | 87.24% | 63.02% | 75.13% |
| CPNE4 | 87.52% | 63.37% | 75.45% |
| CEBPB | 77.47% | 74.63% | 76.05% |
| FAM99A | 83.59% | 72.76% | 78.17% |
| FRMD3 | 94.95% | 64.06% | 79.51% |
| COL4A1 | 95.83% | 67.07% | 81.45% |
| DRD2NCAM | 74.44% | 89.46% | 81.95% |
| ADH7 | 81.36% | 84.72% | 83.04% |
| D5S1970 | 86.35% | 84.57% | 85.46% |
| HRH4 | 86.62% | 95.10% | 90.86% |
| ELK2B | 117.47% | 65.46% | 91.47% |
| CYYR1 | 87.20% | 100.66% | 93.93% |
| GFI1B | 82.72% | 105.43% | 94.08% |
| PFKP | 106.86% | 84.80% | 95.83% |
| PLCG2 | 72.54% | 119.43% | 95.99% |
| HERC1 | 95.22% | 102.99% | 99.10% |
| KANK1 | 92.09% | 106.36% | 99.22% |
| TOM1L1 | 87.28% | 111.48% | 99.38% |
| C14ORF43 | 93.41% | 105.55% | 99.48% |
| SUDS3 | 102.68% | 102.55% | 102.62% |
| D21S1263 | 112.97% | 99.75% | 106.36% |
| LPPR1 | 100.57% | 120.68% | 110.62% |
| D13S169 | 91.66% | 133.14% | 112.40% |
| RBFOX1 | 110.30% | 116.19% | 113.25% |
| D18S1122 | 117.39% | 114.55% | 115.97% |
| SEMA6D | 106.69% | 136.90% | 121.79% |
| EDAR | 149.00% | 115.86% | 132.43% |
| MYOSC | 140.11% | 133.44% | 136.77% |
| ITGB6 | 145.53% | 144.18% | 144.85% |
| GNGT2 | 129.01% | 161.62% | 145.32% |
| COG2 | 155.02% | 149.97% | 152.50% |
| COL4A3 | 144.71% | 166.97% | 155.84% |
| ZC3H7B | 181.45% | 185.95% | 183.70% |
| NELFA | 194.95% | 185.76% | 190.36% |
| D13S1320 | 213.42% | 191.60% | 202.51% |
| USH2A | 219.94% | 226.01% | 222.97% |
| KLK5 | 263.52% | 306.86% | 285.19% |

Although the simple SNP for an identification or phenotypic analysis has been studied as a new marker corresponding to the STR with respect to various populations, the discriminating power for a simple SNP composed of two alleles is generally lower than that of the STR.

The discriminating power for analyzing a degraded sample or a mixed sample was low in the forensic science field, and the demand for simultaneously estimating an identification and a biogeographic origin has been increased, but the existing SNP analysis has a limit.

According to the present invention, the next-generation sequence analyzing system capable of analyzing the microhaplotypes is initiatively established, so that the cost required for analyzing the degraded sample or mixed sample found in the field can be reduced and the labor dependency can be reduced.

According to the present invention, information on the microhaplotypes including a clue for estimating a local origin of a sample is analyzed, so that microhaplotype data for different races (such as microhaplotype data for Korean and foreigners) can be obtained.

According to the present invention, the sufficient coverage for determining a genotype is shown even in a degraded DNA sample, so that a missing person having been left in nature for a long period of time due to war, corpse disposal or the like can be effectively identified.

According to the present invention, NGS-based microhaplotype data can be obtained subject to variously mixed samples (1:1 to 1:99).

The present invention has been specifically described in detail, but it will be apparent to those skilled in the art that the above specific description is provided only for a preferred embodiment and the scope of the present invention is not limited thereto. Accordingly, the substantial scope of the present invention will be defined by the appended claims and equivalents thereof.

What is claimed is:

1. A method of analyzing microhaplotypes by using a next generation sequencing (NGS), the method comprising:

(a) performing a multiplex PCR for simultaneously amplifying microhaplotypes of a DNA sample to have a size of 115 bp to 263 bp;

(b) performing an indexing PCR by using a product of the multiplex PCR; and (c) performing the NGS by using a product of the indexing PCR, wherein the performing the multiplex PCR comprises amplifying a specific sequence of each of the microhaplotypes by using first primers complementarily binding to the microhaplotypes, wherein the performing the indexing PCR comprises generating a bar-coded NGS library by using second primers complementarily binding to the product of the multiplex PCR, wherein in the performing the NGS, a maximum NGS read count obtained for each microhaplotype is less than two times a minimum NGS read count for the each microhaplotype, wherein the microhaplotypes comprise COG2, ITGB6, D18S1122, GFI1B, D21S1263, D5S1970, LOC642852, COL4A1, IGSF21, RXRA, SGCG, LINC0111, LRRN2, CPNE4, GNGT2, COL4A3, SUDS3, D13S169, PLCG2, D22S1159, KIF16B, ADH7, C14ORF43, FAM99A, FRMD4A, OR52S1P, ARHGAP27, LRRC63, KLK5, USH2A, D13S1320, SEMA6D, MYO5C, TOM1L1, HERC1, DRD2NCAM, ELK2B, FRMD3, CEBPB, LINC01233, STATP1, RBFOX1-1, NELFA, ZC3H7B, EDAR, KANK1, RBFOX1, PFKP, LPPR1, CYYR1, HRH4, LOC28716, D12S290, TENM4, CNTN5, and CEP104, and wherein the first primers comprise a plurality of primer sets including:

primer set 12 including primers of SEQ ID NO: 1 and SEQ ID NO: 2 complementarily binding to a locus of the COG2, wherein the primer set 12 has a concentration of 0.18 μM to 0.38 μM;

primer set 34 including primers of SEQ ID NO: 3 and SEQ ID NO: 4 complementarily binding to a locus of the ITGB6, wherein the primer set 34 has a concentration of 0.06 μM to 0.36 μM;

primer set 56 including primers of SEQ ID NO: 5 and SEQ ID NO: 6 complementarily binding to a locus of the D18S1122, wherein the primer set 56 has a concentration of 0.08 μM to 0.28 μM;

primer set 78 including primers of SEQ ID NO: 7 and SEQ ID NO: 8 complementarily binding to a locus of the GFI1B, wherein the primer set 78 has a concentration of 0.08 μM to 0.28 μM;

primer set 910 including primers of SEQ ID NO: 9 and SEQ ID NO: 10 complementarily binding to a locus of the D21S1263, wherein the primer set 910 has a concentration of 0.24 μM to 0.55 μM;

primer set 1112 including primers of SEQ ID NO: 11 and SEQ ID NO: 12 complementarily binding to a locus of the D5S1970, wherein the primer set 1112 has a concentration of 0.90 μM to 1.10 μM;

primer set 1314 including primers of SEQ ID NO: 13 and SEQ ID NO: 14 complementarily binding to a locus of the LOC642852, wherein the primer set 1314 has a concentration of 0.22 μM to 0.42 μM;

primer set 1516 including primers of SEQ ID NO: 15 and SEQ ID NO: 16 complementarily binding to a locus of the COL4A1, wherein the primer set 1516 has a concentration of 0.15 μM to 0.35 μM;

primer set 1718 including primers of SEQ ID NO: 17 and SEQ ID NO: 18 complementarily binding to a locus of the IGSF21, wherein the primer set 1718 has a concentration of 0.30 μM to 0.50 μM;

primer set 1920 including primers of SEQ ID NO: 19 and SEQ ID NO: 20 complementarily binding to a locus of the RXRA, wherein the primer set 1920 has a concentration of 0.15 μM to 0.35 μM;

primer set 2122 including primers of SEQ ID NO: 21 and SEQ ID NO: 22 complementarily binding to a locus of the SGCG, wherein the primer set 2122 has a concentration of 0.40 μM to 0.60 μM;

primer set 2324 including primers of SEQ ID NO: 23 and SEQ ID NO: 24 complementarily binding to a locus of the LINC0111, wherein the primer set 2324 has a concentration of 0.30 μM to 0.60 μM;

primer set 2526 including primers of SEQ ID NO: 25 and SEQ ID NO: 26 complementarily binding to a locus of the LRRN2, wherein the primer set 2526 has a concentration of 0.15 μM to 0.35 μM;

primer set 2728 including primers of SEQ ID NO: 27 and SEQ ID NO: 28 complementarily binding to a locus of the CPNE4, wherein the primer set 2728 has a concentration of 1.90 μM to 2.10 μM;

primer set 2930 including primers of SEQ ID NO: 29 and SEQ ID NO: 30 complementarily binding to a locus of the GNGT2, wherein the primer set 2930 has a concentration of 0.14 μM to 0.34 μM;

primer set 3132 including primers of SEQ ID NO: 31 and SEQ ID NO: 32 complementarily binding to a locus of the COL4A3, wherein the primer set 3132 has a concentration of 0.27 μM to 0.47 μM;

primer set 3334 including primers of SEQ ID NO: 33 and SEQ ID NO: 34 complementarily binding to a locus of the SUDS3, wherein the primer set 3334 has a concentration of 0.19 μM to 0.39 μM;

primer set 3536 including primers of SEQ ID NO: 35 and SEQ ID NO: 36 complementarily binding to a locus of the D13S169, wherein the primer set 3536 has a concentration of 0.45 μM to 0.65 μM;

primer set 3738 including primers of SEQ ID NO: 37 and SEQ ID NO: 38 complementarily binding to a locus of the PLCG2, wherein the primer set 3738 has a concentration of 0.18 μM to 0.38 μM;

primer set 3940 including primers of SEQ ID NO: 39 and SEQ ID NO: 40 complementarily binding to a locus of the D22S1159, wherein the primer set 3940 has a concentration of 0.08 μM to 0.28 μM;

primer set 4142 including primers of SEQ ID NO: 41 and SEQ ID NO: 42 complementarily binding to a locus of the KIF16B, wherein the primer set 4142 has a concentration of 0.19 μM to 0.39 μM;

primer set 4344 including primers of SEQ ID NO: 43 and SEQ ID NO: 44 complementarily binding to a locus of the ADH7, wherein the primer set 4344 has a concentration of 0.26 μM to 0.46 μM;

primer set 4546 including primers of SEQ ID NO: 45 and SEQ ID NO: 46 complementarily binding to a locus of the C14ORF43, wherein the primer set 4546 has a concentration of 0.28 μM to 0.48 μM;

primer set 4748 including primers of SEQ ID NO: 47 and SEQ ID NO: 48 complementarily binding to a locus of the FAM99A, wherein the primer set 4748 has a concentration of 0.50 μM to 0.70 μM;

primer set 4950 including primers of SEQ ID NO: 49 and SEQ ID NO: 50 complementarily binding to a locus of the FRMD4A, wherein the primer set 4950 has a concentration of 0.21 μM to 0.41 μM;

primer set 5152 including primers of SEQ ID NO: 51 and SEQ ID NO: 52 complementarily binding to a locus of the OR5251P, wherein the primer set 5152 has a concentration of 1.30 μM to 1.50 μM;

primer set 5354 including primers of SEQ ID NO: 53 and SEQ ID NO: 54 complementarily binding to a locus of the ARHGAP27, wherein the primer set 5354 has a concentration of 0.40 μM to 0.60 μM;

primer set 5556 including primers of SEQ ID NO: 55 and SEQ ID NO: 56 complementarily binding to a locus of the LRRC63, wherein the primer set 5556 has a concentration of 0.45 μM to 0.65 μM;

primer set 5758 including primers of SEQ ID NO: 57 and SEQ ID NO: 58 complementarily binding to a locus of the KLK5, wherein the primer set 5758 has a concentration of 0.19 μM to 0.39 μM;

primer set 5960 including primers of SEQ ID NO: 59 and SEQ ID NO: 60 complementarily binding to a locus of the USH2A, wherein the primer set 5960 has a concentration of 0.35 μM to 0.55 μM;

primer set 6162 including primers of SEQ ID NO: 61 and SEQ ID NO: 62 complementarily binding to a locus of the D1351320, wherein the primer set 6162 has a concentration of 0.26 μM to 0.46 μM;

primer set 6364 including primers of SEQ ID NO: 63 and SEQ ID NO: 64 complementarily binding to a locus of the SEMA6D, wherein the primer set 6364 has a concentration of 0.15 μM to 0.35 μM;

primer set 6566 including primers of SEQ ID NO: 65 and SEQ ID NO: 66 complementarily binding to a locus of the MYO5C, wherein the primer set 6566 has a concentration of 0.40 μM to 0.60 μM;

primer set 6768 including primers of SEQ ID NO: 67 and SEQ ID NO: 68 complementarily binding to a locus of the TOM1L1, wherein the primer set 6768 has a concentration of 0.40 μM to 0.60 μM;

primer set 6970 including primers of SEQ ID NO: 69 and SEQ ID NO: 70 complementarily binding to a locus of the HERC1, wherein the primer set 6970 has a concentration of 0.25 μM to 0.45 μM;

primer set 7172 including primers of SEQ ID NO: 71 and SEQ ID NO: 72 complementarily binding to a locus of the DRD2NCAM, wherein the primer set 7172 has a concentration of 0.14 μM to 0.34 μM;

primer set 7374 including primers of SEQ ID NO: 73 and SEQ ID NO: 74 complementarily binding to a locus of the ELK2B, wherein the primer set 7374 has a concentration of 1.00 μM to 1.20 μM;

primer set 7576 including primers of SEQ ID NO: 75 and SEQ ID NO: 76 complementarily binding to a locus of the FRMD3, wherein the primer set 7576 has a concentration of 0.40 μM to 0.60 μM;

primer set 7778 including primers of SEQ ID NO: 77 and SEQ ID NO: 78 complementarily binding to a locus of the CEBPB, wherein the primer set 7778 has a concentration of 0.28 μM to 0.48 μM;

primer set 7980 including primers of SEQ ID NO: 79 and SEQ ID NO: 80 complementarily binding to a locus of the LINC01233, wherein the primer set 7980 has a concentration of 0.70 μM to 0.90 μM;

primer set 8182 including primers of SEQ ID NO: 81 and SEQ ID NO: 82 complementarily binding to a locus of the STATP1, wherein the primer set 8182 has a concentration of 0.30 μM to 0.50 μM;

primer set 8384 including primers of SEQ ID NO: 83 and SEQ ID NO: 84 complementarily binding to a locus of the RBFOX1-1, wherein the primer set 8384 has a concentration of 1.20 μM to 1.40 μM;

primer set 8586 including primers of SEQ ID NO: 85 and SEQ ID NO: 86 complementarily binding to a locus of the NELFA, wherein the primer set 8586 has a concentration of 0.18 μM to 0.38 μM;

primer set 8788 including primers of SEQ ID NO: 87 and SEQ ID NO: 88 complementarily binding to a locus of the ZC3H7B, wherein the primer set 8788 has a concentration of 0.25 μM to 0.45 μM;

primer set 8990 including primers of SEQ ID NO: 89 and SEQ ID NO: 90 complementarily binding to a locus of the EDAR, wherein the primer set 8990 has a concentration of 0.05 μM to 0.25 μM;

primer set 9192 including primers of SEQ ID NO: 91 and SEQ ID NO: 92 complementarily binding to a locus of the KANK1, wherein the primer set 9192 has a concentration of 0.15 μM to 0.35 μM;

primer set 9394 including primers of SEQ ID NO: 93 and SEQ ID NO: 94 complementarily binding to a locus of the RBFOX1, wherein the primer set 9394 has a concentration of 0.17 μM to 0.37 μM;

primer set 9596 including primers of SEQ ID NO: 95 and SEQ ID NO: 96 complementarily binding to a locus of the PFKP, wherein the primer set 9596 has a concentration of 0.50 μM to 0.70 μM;

primer set 9798 including primers of SEQ ID NO: 97 and SEQ ID NO: 98 complementarily binding to a locus of the LPPR1, wherein the primer set 9798 has a concentration of 0.20 μM to 0.40 μM;

primer set 99100 including primers of SEQ ID NO: 99 and SEQ ID NO: 100 complementarily binding to a locus of the CYYR1, wherein the primer set 99100 has a concentration of 0.45 μM to 0.65 μM;

primer set 101102 including primers of SEQ ID NO: 101 and SEQ ID NO: 102 complementarily binding to a locus of the HRH4, wherein the primer set 101102 has a concentration of 1.70 μM to 1.90 μM;

primer set 103104 including primers of SEQ ID NO: 103 and SEQ ID NO: 104 complementarily binding to a locus of the LOC28716, wherein the primer set 103104 has a concentration of 0.17 μM to 0.37 μM;

primer set 105106 including primers of SEQ ID NO: 105 and SEQ ID NO: 106 complementarily binding to a locus of the D12S290, wherein the primer set 105106 has a concentration of 0.35 μM to 0.55 μM;

primer set 107108 including primers of SEQ ID NO: 107 and SEQ ID NO: 108 complementarily binding to a locus of the TENM4, wherein the primer set 107108 has a concentration of 0.28 μM to 0.48 μM;

primer set 109110 including primers of SEQ ID NO: 109 and SEQ ID NO: 110 complementarily binding to a locus of the CNTN5, wherein the primer set 109110 has a concentration of 0.55 μM to 0.75 μM; and primer set 111112 including primers of SEQ ID NO: 111 and SEQ ID NO: 112 complementarily binding to a locus of the CEP104, wherein the primer set 111112 has a concentration of 0.19 μM to 0.39 μM.

2. A gene identifying method of identifying a human subject by using the method according to claim 1.

3. The method of claim 1, wherein an average NGS read count of a degraded DNA sample is 50% or more compared to an average NGS read count of a non-degraded DNA sample.

* * * * *

SEQUENCE LISTING

<160> NUMBER OF SEQ ID NOS: 192

<210> SEQ ID NO 1
<211> LENGTH: 52
<212> TYPE: DNA
<213> ORGANISM: Artificial Sequence
<220> FEATURE:
<223> OTHER INFORMATION: COG2_F190

<400> SEQUENCE: 1
tcgtcggcag cgtcagatgt gtataagaga cagcagccca tgtttgtcga tt        52

<210> SEQ ID NO 2
<211> LENGTH: 54
<212> TYPE: DNA
<213> ORGANISM: Artificial Sequence
<220> FEATURE:
<223> OTHER INFORMATION: COG2_R340

<400> SEQUENCE: 2
gtctcgtggg ctcggagatg tgtataagag acaggccaca atccaagttc ccta      54

<210> SEQ ID NO 3
<211> LENGTH: 53
<212> TYPE: DNA
<213> ORGANISM: Artificial Sequence
<220> FEATURE:
<223> OTHER INFORMATION: ITGB6_F201

<400> SEQUENCE: 3
tcgtcggcag cgtcagatgt gtataagaga caggaactgt acccttggca gga       53

<210> SEQ ID NO 4
<211> LENGTH: 54
<212> TYPE: DNA
<213> ORGANISM: Artificial Sequence
<220> FEATURE:
<223> OTHER INFORMATION: ITGB6_R358

<400> SEQUENCE: 4
gtctcgtggg ctcggagatg tgtataagag acagcaatgt ccttgaggct cgta      54

<210> SEQ ID NO 5
<211> LENGTH: 53
<212> TYPE: DNA
<213> ORGANISM: Artificial Sequence
<220> FEATURE:
<223> OTHER INFORMATION: D18S1122_F222

<400> SEQUENCE: 5
tcgtcggcag cgtcagatgt gtataagaga cagcacccac tgaagtttga gca       53

<210> SEQ ID NO 6
<211> LENGTH: 56
<212> TYPE: DNA
<213> ORGANISM: Artificial Sequence
<220> FEATURE:
<223> OTHER INFORMATION: D18S1122_R390

<400> SEQUENCE: 6
gtctcgtggg ctcggagatg tgtataagag acagtgatcc taatcaaggc tatgga    56

<210> SEQ ID NO 7
<211> LENGTH: 53
<212> TYPE: DNA
<213> ORGANISM: Artificial Sequence

```
<220> FEATURE:
<223> OTHER INFORMATION: GFI1B_F230

<400> SEQUENCE: 7
tcgtcggcag cgtcagatgt gtataagaga caggactggt ccaaagtctt ccc       53

<210> SEQ ID NO 8
<211> LENGTH: 54
<212> TYPE: DNA
<213> ORGANISM: Artificial Sequence
<220> FEATURE:
<223> OTHER INFORMATION: GFI1B_R424

<400> SEQUENCE: 8
gtctcgtggg ctcggagatg tgtataagag acagccatca gcatcaatag ccac      54

<210> SEQ ID NO 9
<211> LENGTH: 54
<212> TYPE: DNA
<213> ORGANISM: Artificial Sequence
<220> FEATURE:
<223> OTHER INFORMATION: D21S1263_F271

<400> SEQUENCE: 9
tcgtcggcag cgtcagatgt gtataagaga cagggagcct aaaagaaggt caca      54

<210> SEQ ID NO 10
<211> LENGTH: 53
<212> TYPE: DNA
<213> ORGANISM: Artificial Sequence
<220> FEATURE:
<223> OTHER INFORMATION: D21S1263_R468

<400> SEQUENCE: 10
gtctcgtggg ctcggagatg tgtataagag acagcctgaa cactttgggg cag       53

<210> SEQ ID NO 11
<211> LENGTH: 54
<212> TYPE: DNA
<213> ORGANISM: Artificial Sequence
<220> FEATURE:
<223> OTHER INFORMATION: D5S1970_F254

<400> SEQUENCE: 11
tcgtcggcag cgtcagatgt gtataagaga cagcacatgg aggacaaaag tgaa      54

<210> SEQ ID NO 12
<211> LENGTH: 55
<212> TYPE: DNA
<213> ORGANISM: Artificial Sequence
<220> FEATURE:
<223> OTHER INFORMATION: D5S1970_R463

<400> SEQUENCE: 12
gtctcgtggg ctcggagatg tgtataagag acaggtgctg gtgatgacaa gtgag     55

<210> SEQ ID NO 13
<211> LENGTH: 52
<212> TYPE: DNA
<213> ORGANISM: Artificial Sequence
<220> FEATURE:
<223> OTHER INFORMATION: LOC642852_F216

<400> SEQUENCE: 13
tcgtcggcag cgtcagatgt gtataagaga caggtcatct gggaaacgtg gg        52
```

<210> SEQ ID NO 14
<211> LENGTH: 53
<212> TYPE: DNA
<213> ORGANISM: Artificial Sequence
<220> FEATURE:
<223> OTHER INFORMATION: LOC642852_R435

<400> SEQUENCE: 14
gtctcgtggg ctcggagatg tgtataagag acagcgtctg catttccgct gac       53

<210> SEQ ID NO 15
<211> LENGTH: 54
<212> TYPE: DNA
<213> ORGANISM: Artificial Sequence
<220> FEATURE:
<223> OTHER INFORMATION: COL4A1_F206

<400> SEQUENCE: 15
tcgtcggcag cgtcagatgt gtataagaga cagagtgtat caaacagggg cctt      54

<210> SEQ ID NO 16
<211> LENGTH: 54
<212> TYPE: DNA
<213> ORGANISM: Artificial Sequence
<220> FEATURE:
<223> OTHER INFORMATION: COL4A1_R431

<400> SEQUENCE: 16
gtctcgtggg ctcggagatg tgtataagag acagcacgtg gggagtacac attc      54

<210> SEQ ID NO 17
<211> LENGTH: 53
<212> TYPE: DNA
<213> ORGANISM: Artificial Sequence
<220> FEATURE:
<223> OTHER INFORMATION: IGSF21_F208

<400> SEQUENCE: 17
tcgtcggcag cgtcagatgt gtataagaga caggtaattt ggggtccaga gca       53

<210> SEQ ID NO 18
<211> LENGTH: 54
<212> TYPE: DNA
<213> ORGANISM: Artificial Sequence
<220> FEATURE:
<223> OTHER INFORMATION: IGSF21_R434

<400> SEQUENCE: 18
gtctcgtggg ctcggagatg tgtataagag acagaattcg caacagtgaa agca      54

<210> SEQ ID NO 19
<211> LENGTH: 52
<212> TYPE: DNA
<213> ORGANISM: Artificial Sequence
<220> FEATURE:
<223> OTHER INFORMATION: RXRA_F231

<400> SEQUENCE: 19
tcgtcggcag cgtcagatgt gtataagaga cagcacagca atccccttg ag         52

<210> SEQ ID NO 20
<211> LENGTH: 53
<212> TYPE: DNA
<213> ORGANISM: Artificial Sequence
<220> FEATURE:
<223> OTHER INFORMATION: RXRA_R463

```
<400> SEQUENCE: 20
gtctcgtggg ctcggagatg tgtataagag acagggctct gatctgacgg caa        53

<210> SEQ ID NO 21
<211> LENGTH: 54
<212> TYPE: DNA
<213> ORGANISM: Artificial Sequence
<220> FEATURE:
<223> OTHER INFORMATION: SGCG_F212

<400> SEQUENCE: 21
tcgtcggcag cgtcagatgt gtataagaga caggaggaga gacagcaagg agaa       54

<210> SEQ ID NO 22
<211> LENGTH: 55
<212> TYPE: DNA
<213> ORGANISM: Artificial Sequence
<220> FEATURE:
<223> OTHER INFORMATION: SGCG_R447

<400> SEQUENCE: 22
gtctcgtggg ctcggagatg tgtataagag acagtctgcc aagtgatcaa ctcaa      55

<210> SEQ ID NO 23
<211> LENGTH: 53
<212> TYPE: DNA
<213> ORGANISM: Artificial Sequence
<220> FEATURE:
<223> OTHER INFORMATION: LINC0111_F280

<400> SEQUENCE: 23
tcgtcggcag cgtcagatgt gtataagaga caggagggtg tgtttaggat ggg        53

<210> SEQ ID NO 24
<211> LENGTH: 53
<212> TYPE: DNA
<213> ORGANISM: Artificial Sequence
<220> FEATURE:
<223> OTHER INFORMATION: LINC0111_R519

<400> SEQUENCE: 24
gtctcgtggg ctcggagatg tgtataagag acagctcccc tggccaaaca tta        53

<210> SEQ ID NO 25
<211> LENGTH: 53
<212> TYPE: DNA
<213> ORGANISM: Artificial Sequence
<220> FEATURE:
<223> OTHER INFORMATION: LRRN2_F227

<400> SEQUENCE: 25
tcgtcggcag cgtcagatgt gtataagaga caggtttgtc tccccacaaa gca        53

<210> SEQ ID NO 26
<211> LENGTH: 54
<212> TYPE: DNA
<213> ORGANISM: Artificial Sequence
<220> FEATURE:
<223> OTHER INFORMATION: LRRN2_R472

<400> SEQUENCE: 26
gtctcgtggg ctcggagatg tgtataagag acaggtcaca tcaccatctc cgtc       54

<210> SEQ ID NO 27
```

```
<211> LENGTH: 62
<212> TYPE: DNA
<213> ORGANISM: Artificial Sequence
<220> FEATURE:
<223> OTHER INFORMATION: CPNE4_F222

<400> SEQUENCE: 27
tcgtcggcag cgtcagatgt gtataagaga cagctatctt atttaatatt cataacaacc      60
tt                                                                    62

<210> SEQ ID NO 28
<211> LENGTH: 54
<212> TYPE: DNA
<213> ORGANISM: Artificial Sequence
<220> FEATURE:
<223> OTHER INFORMATION: CPNE4_R473

<400> SEQUENCE: 28
gtctcgtggg ctcggagatg tgtataagag acaggaaagt gcctgggatc cact            54

<210> SEQ ID NO 29
<211> LENGTH: 53
<212> TYPE: DNA
<213> ORGANISM: Artificial Sequence
<220> FEATURE:
<223> OTHER INFORMATION: GNGT2_F158

<400> SEQUENCE: 29
tcgtcggcag cgtcagatgt gtataagaga cagacaccca tccaatgaca agg             53

<210> SEQ ID NO 30
<211> LENGTH: 54
<212> TYPE: DNA
<213> ORGANISM: Artificial Sequence
<220> FEATURE:
<223> OTHER INFORMATION: GNGT2_R314

<400> SEQUENCE: 30
gtctcgtggg ctcggagatg tgtataagag acaggagcac ggaagttagg atgg            54

<210> SEQ ID NO 31
<211> LENGTH: 53
<212> TYPE: DNA
<213> ORGANISM: Artificial Sequence
<220> FEATURE:
<223> OTHER INFORMATION: COL4A3_F216

<400> SEQUENCE: 31
tcgtcggcag cgtcagatgt gtataagaga cagtccttag cctctcaaaa tcc             53

<210> SEQ ID NO 32
<211> LENGTH: 55
<212> TYPE: DNA
<213> ORGANISM: Artificial Sequence
<220> FEATURE:
<223> OTHER INFORMATION: COL4A3_R382

<400> SEQUENCE: 32
gtctcgtggg ctcggagatg tgtataagag acagggaaat gaacttccat cagca           55

<210> SEQ ID NO 33
<211> LENGTH: 56
<212> TYPE: DNA
<213> ORGANISM: Artificial Sequence
<220> FEATURE:
<223> OTHER INFORMATION: SUDS3_F215
```

-continued

<400> SEQUENCE: 33
tcgtcggcag cgtcagatgt gtataagaga cagaggaaca ctggtatagg aggaga    56

<210> SEQ ID NO 34
<211> LENGTH: 54
<212> TYPE: DNA
<213> ORGANISM: Artificial Sequence
<220> FEATURE:
<223> OTHER INFORMATION: SUDS3_R394

<400> SEQUENCE: 34
gtctcgtggg ctcggagatg tgtataagag acagggaggg ttgtttcctt tgtg    54

<210> SEQ ID NO 35
<211> LENGTH: 55
<212> TYPE: DNA
<213> ORGANISM: Artificial Sequence
<220> FEATURE:
<223> OTHER INFORMATION: D13S169_F277

<400> SEQUENCE: 35
tcgtcggcag cgtcagatgt gtataagaga cagctggaat cataagcata gcaca    55

<210> SEQ ID NO 36
<211> LENGTH: 57
<212> TYPE: DNA
<213> ORGANISM: Artificial Sequence
<220> FEATURE:
<223> OTHER INFORMATION: D13S169_R469

<400> SEQUENCE: 36
gtctcgtggg ctcggagatg tgtataagag acagaatgca gaactcacat gttaagg    57

<210> SEQ ID NO 37
<211> LENGTH: 53
<212> TYPE: DNA
<213> ORGANISM: Artificial Sequence
<220> FEATURE:
<223> OTHER INFORMATION: PLCG2_F212

<400> SEQUENCE: 37
tcgtcggcag cgtcagatgt gtataagaga caggggcttt ctgctcagac ttt    53

<210> SEQ ID NO 38
<211> LENGTH: 54
<212> TYPE: DNA
<213> ORGANISM: Artificial Sequence
<220> FEATURE:
<223> OTHER INFORMATION: PLCG2_R416

<400> SEQUENCE: 38
gtctcgtggg ctcggagatg tgtataagag acaggttcca ttctgtggaa tccg    54

<210> SEQ ID NO 39
<211> LENGTH: 53
<212> TYPE: DNA
<213> ORGANISM: Artificial Sequence
<220> FEATURE:
<223> OTHER INFORMATION: D22S1159_F220

<400> SEQUENCE: 39
tcgtcggcag cgtcagatgt gtataagaga cagctccttt aggggtggca agt    53

<210> SEQ ID NO 40

<211> LENGTH: 54
<212> TYPE: DNA
<213> ORGANISM: Artificial Sequence
<220> FEATURE:
<223> OTHER INFORMATION: D22S1159_R435

<400> SEQUENCE: 40
gtctcgtggg ctcggagatg tgtataagag acagtaggga ctggggaact cctt    54

<210> SEQ ID NO 41
<211> LENGTH: 53
<212> TYPE: DNA
<213> ORGANISM: Artificial Sequence
<220> FEATURE:
<223> OTHER INFORMATION: KIF16B_F227

<400> SEQUENCE: 41
tcgtcggcag cgtcagatgt gtataagaga cagaagagaa caaaccacct ggg    53

<210> SEQ ID NO 42
<211> LENGTH: 56
<212> TYPE: DNA
<213> ORGANISM: Artificial Sequence
<220> FEATURE:
<223> OTHER INFORMATION: KIF16B_R447

<400> SEQUENCE: 42
gtctcgtggg ctcggagatg tgtataagag acagcaagtc aatgtgagca ttacca    56

<210> SEQ ID NO 43
<211> LENGTH: 54
<212> TYPE: DNA
<213> ORGANISM: Artificial Sequence
<220> FEATURE:
<223> OTHER INFORMATION: ADH7_F213

<400> SEQUENCE: 43
tcgtcggcag cgtcagatgt gtataagaga cagacacagg agatggatga ctcc    54

<210> SEQ ID NO 44
<211> LENGTH: 54
<212> TYPE: DNA
<213> ORGANISM: Artificial Sequence
<220> FEATURE:
<223> OTHER INFORMATION: ADH7_R437

<400> SEQUENCE: 44
gtctcgtggg ctcggagatg tgtataagag acagctggct ttctccacat gtca    54

<210> SEQ ID NO 45
<211> LENGTH: 54
<212> TYPE: DNA
<213> ORGANISM: Artificial Sequence
<220> FEATURE:
<223> OTHER INFORMATION: C14ORF43_F215

<400> SEQUENCE: 45
tcgtcggcag cgtcagatgt gtataagaga cagggtgtct ggaaaactgt agcg    54

<210> SEQ ID NO 46
<211> LENGTH: 54
<212> TYPE: DNA
<213> ORGANISM: Artificial Sequence
<220> FEATURE:
<223> OTHER INFORMATION: C14ORF43_R444

<400> SEQUENCE: 46
gtctcgtggg ctcggagatg tgtataagag acagctgaga gaagccaatg cagg        54

<210> SEQ ID NO 47
<211> LENGTH: 52
<212> TYPE: DNA
<213> ORGANISM: Artificial Sequence
<220> FEATURE:
<223> OTHER INFORMATION: FAM99A_F282

<400> SEQUENCE: 47
tcgtcggcag cgtcagatgt gtataagaga cagcctgcct gcttttcctg at          52

<210> SEQ ID NO 48
<211> LENGTH: 53
<212> TYPE: DNA
<213> ORGANISM: Artificial Sequence
<220> FEATURE:
<223> OTHER INFORMATION: FAM99A_R517

<400> SEQUENCE: 48
gtctcgtggg ctcggagatg tgtataagag acaggagatg tctcctgggc agc         53

<210> SEQ ID NO 49
<211> LENGTH: 55
<212> TYPE: DNA
<213> ORGANISM: Artificial Sequence
<220> FEATURE:
<223> OTHER INFORMATION: FRMD4A_F205

<400> SEQUENCE: 49
tcgtcggcag cgtcagatgt gtataagaga caggcacagc tttgttttat ctgga       55

<210> SEQ ID NO 50
<211> LENGTH: 56
<212> TYPE: DNA
<213> ORGANISM: Artificial Sequence
<220> FEATURE:
<223> OTHER INFORMATION: FRMD4A_R443

<400> SEQUENCE: 50
gtctcgtggg ctcggagatg tgtataagag acagcctatc ctgttctttg ggtgag      56

<210> SEQ ID NO 51
<211> LENGTH: 55
<212> TYPE: DNA
<213> ORGANISM: Artificial Sequence
<220> FEATURE:
<223> OTHER INFORMATION: OR52S1P_F160

<400> SEQUENCE: 51
tcgtcggcag cgtcagatgt gtataagaga cagtccattt tgctgaccta aacct       55

<210> SEQ ID NO 52
<211> LENGTH: 59
<212> TYPE: DNA
<213> ORGANISM: Artificial Sequence
<220> FEATURE:
<223> OTHER INFORMATION: OR52S1P_R402

<400> SEQUENCE: 52
gtctcgtggg ctcggagatg tgtataagag acagaaaaaa acaagtataa gggatgaca   59

<210> SEQ ID NO 53

```
<211> LENGTH: 53
<212> TYPE: DNA
<213> ORGANISM: Artificial Sequence
<220> FEATURE:
<223> OTHER INFORMATION: ARHGAP27_F222

<400> SEQUENCE: 53
tcgtcggcag cgtcagatgt gtataagaga caggcctgag gaggatagct tca         53

<210> SEQ ID NO 54
<211> LENGTH: 53
<212> TYPE: DNA
<213> ORGANISM: Artificial Sequence
<220> FEATURE:
<223> OTHER INFORMATION: ARHGAP27_R470

<400> SEQUENCE: 54
gtctcgtggg ctcggagatg tgtataagag acaggtgtgc gatagcgtgt gtg         53

<210> SEQ ID NO 55
<211> LENGTH: 53
<212> TYPE: DNA
<213> ORGANISM: Artificial Sequence
<220> FEATURE:
<223> OTHER INFORMATION: LRRC63_F257

<400> SEQUENCE: 55
tcgtcggcag cgtcagatgt gtataagaga cagatagtct ccgtaaggcc tgg         53

<210> SEQ ID NO 56
<211> LENGTH: 55
<212> TYPE: DNA
<213> ORGANISM: Artificial Sequence
<220> FEATURE:
<223> OTHER INFORMATION: LRRC63_R510

<400> SEQUENCE: 56
gtctcgtggg ctcggagatg tgtataagag acagtggtgt attgccaaac agaaa       55

<210> SEQ ID NO 57
<211> LENGTH: 53
<212> TYPE: DNA
<213> ORGANISM: Artificial Sequence
<220> FEATURE:
<223> OTHER INFORMATION: KLK5_F221

<400> SEQUENCE: 57
tcgtcggcag cgtcagatgt gtataagaga cagagacaga cccactacgg gtg         53

<210> SEQ ID NO 58
<211> LENGTH: 54
<212> TYPE: DNA
<213> ORGANISM: Artificial Sequence
<220> FEATURE:
<223> OTHER INFORMATION: KLK5_R335

<400> SEQUENCE: 58
gtctcgtggg ctcggagatg tgtataagag acagtcaaga aatccaggta aggg        54

<210> SEQ ID NO 59
<211> LENGTH: 54
<212> TYPE: DNA
<213> ORGANISM: Artificial Sequence
<220> FEATURE:
<223> OTHER INFORMATION: USH2A_F167
```

```
<400> SEQUENCE: 59
tcgtcggcag cgtcagatgt gtataagaga cagagaaact ttgccttttg acca         54

<210> SEQ ID NO 60
<211> LENGTH: 54
<212> TYPE: DNA
<213> ORGANISM: Artificial Sequence
<220> FEATURE:
<223> OTHER INFORMATION: USH2A_R290

<400> SEQUENCE: 60
gtctcgtggg ctcggagatg tgtataagag acaggccctg ccttctagtt ctga         54

<210> SEQ ID NO 61
<211> LENGTH: 58
<212> TYPE: DNA
<213> ORGANISM: Artificial Sequence
<220> FEATURE:
<223> OTHER INFORMATION: D13S1320_F226

<400> SEQUENCE: 61
tcgtcggcag cgtcagatgt gtataagaga cagttctcta ctaagaaacc aaccacac    58

<210> SEQ ID NO 62
<211> LENGTH: 55
<212> TYPE: DNA
<213> ORGANISM: Artificial Sequence
<220> FEATURE:
<223> OTHER INFORMATION: D13S1320_R379

<400> SEQUENCE: 62
gtctcgtggg ctcggagatg tgtataagag acagtgaaaa gggaagtgga aaaca        55

<210> SEQ ID NO 63
<211> LENGTH: 53
<212> TYPE: DNA
<213> ORGANISM: Artificial Sequence
<220> FEATURE:
<223> OTHER INFORMATION: SEMA6D_F224

<400> SEQUENCE: 63
tcgtcggcag cgtcagatgt gtataagaga cagctctcaa gcccactctc tgg          53

<210> SEQ ID NO 64
<211> LENGTH: 57
<212> TYPE: DNA
<213> ORGANISM: Artificial Sequence
<220> FEATURE:
<223> OTHER INFORMATION: SEMA6D_R395

<400> SEQUENCE: 64
gtctcgtggg ctcggagatg tgtataagag acaggaagta gaaagccttc cattgtg     57

<210> SEQ ID NO 65
<211> LENGTH: 54
<212> TYPE: DNA
<213> ORGANISM: Artificial Sequence
<220> FEATURE:
<223> OTHER INFORMATION: MYO5C_F215

<400> SEQUENCE: 65
tcgtcggcag cgtcagatgt gtataagaga cagagggtcc gacacaattt ttta         54

<210> SEQ ID NO 66
```

<211> LENGTH: 54
<212> TYPE: DNA
<213> ORGANISM: Artificial Sequence
<220> FEATURE:
<223> OTHER INFORMATION: MYO5C_R392

<400> SEQUENCE: 66
gtctcgtggg ctcggagatg tgtataagag acagacctgc aacatattc acca                54

<210> SEQ ID NO 67
<211> LENGTH: 56
<212> TYPE: DNA
<213> ORGANISM: Artificial Sequence
<220> FEATURE:
<223> OTHER INFORMATION: TOM1L1_F215

<400> SEQUENCE: 67
tcgtcggcag cgtcagatgt gtataagaga cagtctctct ccattattcc ctgaac            56

<210> SEQ ID NO 68
<211> LENGTH: 55
<212> TYPE: DNA
<213> ORGANISM: Artificial Sequence
<220> FEATURE:
<223> OTHER INFORMATION: TOM1L1_R404

<400> SEQUENCE: 68
gtctcgtggg ctcggagatg tgtataagag acagggaaca tcacgggaat ctttt             55

<210> SEQ ID NO 69
<211> LENGTH: 54
<212> TYPE: DNA
<213> ORGANISM: Artificial Sequence
<220> FEATURE:
<223> OTHER INFORMATION: HERC1_F228

<400> SEQUENCE: 69
tcgtcggcag cgtcagatgt gtataagaga cagcaaaggc ctatctcaaa ggtg              54

<210> SEQ ID NO 70
<211> LENGTH: 53
<212> TYPE: DNA
<213> ORGANISM: Artificial Sequence
<220> FEATURE:
<223> OTHER INFORMATION: HERC1_R422

<400> SEQUENCE: 70
gtctcgtggg ctcggagatg tgtataagag acaggggggtg gatggagcag tag              53

<210> SEQ ID NO 71
<211> LENGTH: 52
<212> TYPE: DNA
<213> ORGANISM: Artificial Sequence
<220> FEATURE:
<223> OTHER INFORMATION: DRD2NCAM_F219

<400> SEQUENCE: 71
tcgtcggcag cgtcagatgt gtataagaga cagatgccca tgggtgtctg ag                52

<210> SEQ ID NO 72
<211> LENGTH: 54
<212> TYPE: DNA
<213> ORGANISM: Artificial Sequence
<220> FEATURE:
<223> OTHER INFORMATION: DRD2NCAM_R421

<400> SEQUENCE: 72
gtctcgtggg ctcggagatg tgtataagag acaggtgatg aatgggtgcc aaat    54

<210> SEQ ID NO 73
<211> LENGTH: 58
<212> TYPE: DNA
<213> ORGANISM: Artificial Sequence
<220> FEATURE:
<223> OTHER INFORMATION: ELK2B_F225

<400> SEQUENCE: 73
tcgtcggcag cgtcagatgt gtataagaga cagaagttaa tcttaagaac aatcacca    58

<210> SEQ ID NO 74
<211> LENGTH: 60
<212> TYPE: DNA
<213> ORGANISM: Artificial Sequence
<220> FEATURE:
<223> OTHER INFORMATION: ELK2B_R432

<400> SEQUENCE: 74
gtctcgtggg ctcggagatg tgtataagag acagcaagaa tctctacttt ttaactgatt    60

<210> SEQ ID NO 75
<211> LENGTH: 57
<212> TYPE: DNA
<213> ORGANISM: Artificial Sequence
<220> FEATURE:
<223> OTHER INFORMATION: FRMD3_F193

<400> SEQUENCE: 75
tcgtcggcag cgtcagatgt gtataagaga cagtgaatgt ggtaactgag actagga    57

<210> SEQ ID NO 76
<211> LENGTH: 54
<212> TYPE: DNA
<213> ORGANISM: Artificial Sequence
<220> FEATURE:
<223> OTHER INFORMATION: FRMD3_R412

<400> SEQUENCE: 76
gtctcgtggg ctcggagatg tgtataagag acagtgatcc ttgggggagc ttta    54

<210> SEQ ID NO 77
<211> LENGTH: 52
<212> TYPE: DNA
<213> ORGANISM: Artificial Sequence
<220> FEATURE:
<223> OTHER INFORMATION: CEBPB_F220

<400> SEQUENCE: 77
tcgtcggcag cgtcagatgt gtataagaga cagagcaggg ccaggcatat ag    52

<210> SEQ ID NO 78
<211> LENGTH: 54
<212> TYPE: DNA
<213> ORGANISM: Artificial Sequence
<220> FEATURE:
<223> OTHER INFORMATION: CEBPB_R443

<400> SEQUENCE: 78
gtctcgtggg ctcggagatg tgtataagag acagcatcct caccacaaac ctca    54

<210> SEQ ID NO 79

<210> SEQ ID NO 79
<211> LENGTH: 54
<212> TYPE: DNA
<213> ORGANISM: Artificial Sequence
<220> FEATURE:
<223> OTHER INFORMATION: LINC01233_F148

<400> SEQUENCE: 79
tcgtcggcag cgtcagatgt gtataagaga cagaaggcca tgttacattg gaaa      54

<210> SEQ ID NO 80
<211> LENGTH: 54
<212> TYPE: DNA
<213> ORGANISM: Artificial Sequence
<220> FEATURE:
<223> OTHER INFORMATION: LINC01233_R384

<400> SEQUENCE: 80
gtctcgtggg ctcggagatg tgtataagag acagggtcgc atgtctcctg gtag      54

<210> SEQ ID NO 81
<211> LENGTH: 53
<212> TYPE: DNA
<213> ORGANISM: Artificial Sequence
<220> FEATURE:
<223> OTHER INFORMATION: STATP1_F221

<400> SEQUENCE: 81
tcgtcggcag cgtcagatgt gtataagaga cagagccatt gcagtcatct gaa       53

<210> SEQ ID NO 82
<211> LENGTH: 54
<212> TYPE: DNA
<213> ORGANISM: Artificial Sequence
<220> FEATURE:
<223> OTHER INFORMATION: STATP1_R472

<400> SEQUENCE: 82
gtctcgtggg ctcggagatg tgtataagag acagtggaag caccatacca ctca      54

<210> SEQ ID NO 83
<211> LENGTH: 54
<212> TYPE: DNA
<213> ORGANISM: Artificial Sequence
<220> FEATURE:
<223> OTHER INFORMATION: RBFOX1-1_F201

<400> SEQUENCE: 83
tcgtcggcag cgtcagatgt gtataagaga caggccctgg agattgtttc aagt      54

<210> SEQ ID NO 84
<211> LENGTH: 55
<212> TYPE: DNA
<213> ORGANISM: Artificial Sequence
<220> FEATURE:
<223> OTHER INFORMATION: RBFOX1-1_R455

<400> SEQUENCE: 84
gtctcgtggg ctcggagatg tgtataagag acagcccgtt tctgattctc tttca     55

<210> SEQ ID NO 85
<211> LENGTH: 53
<212> TYPE: DNA
<213> ORGANISM: Artificial Sequence
<220> FEATURE:
<223> OTHER INFORMATION: NELFA_F203

-continued

<400> SEQUENCE: 85
tcgtcggcag cgtcagatgt gtataagaga cagagcccat cttgagcaca gaa        53

<210> SEQ ID NO 86
<211> LENGTH: 57
<212> TYPE: DNA
<213> ORGANISM: Artificial Sequence
<220> FEATURE:
<223> OTHER INFORMATION: NELFA_R324

<400> SEQUENCE: 86
gtctcgtggg ctcggagatg tgtataagag acagggataa taagctcctt tcttccc     57

<210> SEQ ID NO 87
<211> LENGTH: 53
<212> TYPE: DNA
<213> ORGANISM: Artificial Sequence
<220> FEATURE:
<223> OTHER INFORMATION: ZC3H7B_F213

<400> SEQUENCE: 87
tcgtcggcag cgtcagatgt gtataagaga cagccagagc tttgcagcac ttt        53

<210> SEQ ID NO 88
<211> LENGTH: 55
<212> TYPE: DNA
<213> ORGANISM: Artificial Sequence
<220> FEATURE:
<223> OTHER INFORMATION: ZC3H7B_R357

<400> SEQUENCE: 88
gtctcgtggg ctcggagatg tgtataagag acagtgctac aaaggcagat catca       55

<210> SEQ ID NO 89
<211> LENGTH: 54
<212> TYPE: DNA
<213> ORGANISM: Artificial Sequence
<220> FEATURE:
<223> OTHER INFORMATION: EDAR_F230

<400> SEQUENCE: 89
tcgtcggcag cgtcagatgt gtataagaga cagtgaagag ctaacttgtg cagg        54

<210> SEQ ID NO 90
<211> LENGTH: 54
<212> TYPE: DNA
<213> ORGANISM: Artificial Sequence
<220> FEATURE:
<223> OTHER INFORMATION: EDAR_R395

<400> SEQUENCE: 90
gtctcgtggg ctcggagatg tgtataagag acaggctggc tagaccctcc atta        54

<210> SEQ ID NO 91
<211> LENGTH: 53
<212> TYPE: DNA
<213> ORGANISM: Artificial Sequence
<220> FEATURE:
<223> OTHER INFORMATION: KANK1_F172

<400> SEQUENCE: 91
tcgtcggcag cgtcagatgt gtataagaga cagtttctgc cctcaaggat tgt        53

<210> SEQ ID NO 92

-continued

<210> SEQ ID NO 92
<211> LENGTH: 52
<212> TYPE: DNA
<213> ORGANISM: Artificial Sequence
<220> FEATURE:
<223> OTHER INFORMATION: KANK1_R347

<400> SEQUENCE: 92
gtctcgtggg ctcggagatg tgtataagag acagagggca ggggtgcaat ct         52

<210> SEQ ID NO 93
<211> LENGTH: 54
<212> TYPE: DNA
<213> ORGANISM: Artificial Sequence
<220> FEATURE:
<223> OTHER INFORMATION: RBFOX1_F228

<400> SEQUENCE: 93
tcgtcggcag cgtcagatgt gtataagaga cagcttgggt ccatctcagg aata       54

<210> SEQ ID NO 94
<211> LENGTH: 54
<212> TYPE: DNA
<213> ORGANISM: Artificial Sequence
<220> FEATURE:
<223> OTHER INFORMATION: RBFOX1_R416

<400> SEQUENCE: 94
gtctcgtggg ctcggagatg tgtataagag acagaatacc acggatttcc cctc       54

<210> SEQ ID NO 95
<211> LENGTH: 53
<212> TYPE: DNA
<213> ORGANISM: Artificial Sequence
<220> FEATURE:
<223> OTHER INFORMATION: PFKP_F199

<400> SEQUENCE: 95
tcgtcggcag cgtcagatgt gtataagaga cagcgttctt tttttccccc aga        53

<210> SEQ ID NO 96
<211> LENGTH: 55
<212> TYPE: DNA
<213> ORGANISM: Artificial Sequence
<220> FEATURE:
<223> OTHER INFORMATION: PFKP_R391

<400> SEQUENCE: 96
gtctcgtggg ctcggagatg tgtataagag acagtgctgg tacaatcaca ggaga      55

<210> SEQ ID NO 97
<211> LENGTH: 52
<212> TYPE: DNA
<213> ORGANISM: Artificial Sequence
<220> FEATURE:
<223> OTHER INFORMATION: LPPR1_F228

<400> SEQUENCE: 97
tcgtcggcag cgtcagatgt gtataagaga caggggggatt ggcagtcttc at        52

<210> SEQ ID NO 98
<211> LENGTH: 54
<212> TYPE: DNA
<213> ORGANISM: Artificial Sequence
<220> FEATURE:
<223> OTHER INFORMATION: LPPR1_R421

<400> SEQUENCE: 98
gtctcgtggg ctcggagatg tgtataagag acagtggccc agtatcatac agcc    54

<210> SEQ ID NO 99
<211> LENGTH: 54
<212> TYPE: DNA
<213> ORGANISM: Artificial Sequence
<220> FEATURE:
<223> OTHER INFORMATION: CYYR1_F228

<400> SEQUENCE: 99
tcgtcggcag cgtcagatgt gtataagaga cagccaggga agatatgtgc tcaa    54

<210> SEQ ID NO 100
<211> LENGTH: 55
<212> TYPE: DNA
<213> ORGANISM: Artificial Sequence
<220> FEATURE:
<223> OTHER INFORMATION: CYYR1_R431

<400> SEQUENCE: 100
gtctcgtggg ctcggagatg tgtataagag acagccttgg attgcaagag actcc    55

<210> SEQ ID NO 101
<211> LENGTH: 53
<212> TYPE: DNA
<213> ORGANISM: Artificial Sequence
<220> FEATURE:
<223> OTHER INFORMATION: HRH4_F202

<400> SEQUENCE: 101
tcgtcggcag cgtcagatgt gtataagaga cagccagggg actgattttt cct    53

<210> SEQ ID NO 102
<211> LENGTH: 57
<212> TYPE: DNA
<213> ORGANISM: Artificial Sequence
<220> FEATURE:
<223> OTHER INFORMATION: HRH4_R416

<400> SEQUENCE: 102
gtctcgtggg ctcggagatg tgtataagag acagtggaac ctataaataa tgcaaag    57

<210> SEQ ID NO 103
<211> LENGTH: 52
<212> TYPE: DNA
<213> ORGANISM: Artificial Sequence
<220> FEATURE:
<223> OTHER INFORMATION: LOC28716_F225

<400> SEQUENCE: 103
tcgtcggcag cgtcagatgt gtataagaga cagctgctgg ctgtgtggat gt    52

<210> SEQ ID NO 104
<211> LENGTH: 56
<212> TYPE: DNA
<213> ORGANISM: Artificial Sequence
<220> FEATURE:
<223> OTHER INFORMATION: LOC28716_R451

<400> SEQUENCE: 104
gtctcgtggg ctcggagatg tgtataagag acagtgtcag attttcttag gaccga    56

<210> SEQ ID NO 105

<210> SEQ ID NO 105
<211> LENGTH: 56
<212> TYPE: DNA
<213> ORGANISM: Artificial Sequence
<220> FEATURE:
<223> OTHER INFORMATION: D12S290_F222

<400> SEQUENCE: 105
tcgtcggcag cgtcagatgt gtataagaga cagcttcaag gtatttccag tacccacccc 56

<210> SEQ ID NO 106
<211> LENGTH: 54
<212> TYPE: DNA
<213> ORGANISM: Artificial Sequence
<220> FEATURE:
<223> OTHER INFORMATION: D12S290_R453

<400> SEQUENCE: 106
gtctcgtggg ctcggagatg tgtataagag acagcctgag ccactgattt ttcc 54

<210> SEQ ID NO 107
<211> LENGTH: 56
<212> TYPE: DNA
<213> ORGANISM: Artificial Sequence
<220> FEATURE:
<223> OTHER INFORMATION: TENM4_F222

<400> SEQUENCE: 107
tcgtcggcag cgtcagatgt gtataagaga cagtgtcagc actccagtat cacttt 56

<210> SEQ ID NO 108
<211> LENGTH: 53
<212> TYPE: DNA
<213> ORGANISM: Artificial Sequence
<220> FEATURE:
<223> OTHER INFORMATION: TENM4_R458

<400> SEQUENCE: 108
gtctcgtggg ctcggagatg tgtataagag acaggccgca agggagtcag tat 53

<210> SEQ ID NO 109
<211> LENGTH: 56
<212> TYPE: DNA
<213> ORGANISM: Artificial Sequence
<220> FEATURE:
<223> OTHER INFORMATION: CNTN5_F228

<400> SEQUENCE: 109
tcgtcggcag cgtcagatgt gtataagaga cagggggaaac aaaggtatgt aaaggc 56

<210> SEQ ID NO 110
<211> LENGTH: 56
<212> TYPE: DNA
<213> ORGANISM: Artificial Sequence
<220> FEATURE:
<223> OTHER INFORMATION: CNTN5_R481

<400> SEQUENCE: 110
gtctcgtggg ctcggagatg tgtataagag acagccagtt tccctgtaac aactca 56

<210> SEQ ID NO 111
<211> LENGTH: 53
<212> TYPE: DNA
<213> ORGANISM: Artificial Sequence
<220> FEATURE:
<223> OTHER INFORMATION: CEP104_F230

<400> SEQUENCE: 111
tcgtcggcag cgtcagatgt gtataagaga caggtttcc attcagctgg gag    53

<210> SEQ ID NO 112
<211> LENGTH: 55
<212> TYPE: DNA
<213> ORGANISM: Artificial Sequence
<220> FEATURE:
<223> OTHER INFORMATION: CEP104_R492

<400> SEQUENCE: 112
gtctcgtggg ctcggagatg tgtataagag acagcaacag gctctcactc actca    55

<210> SEQ ID NO 113
<211> LENGTH: 75
<212> TYPE: DNA
<213> ORGANISM: Artificial Sequence
<220> FEATURE:
<223> OTHER INFORMATION: KLK5

<400> SEQUENCE: 113
ttgatcttaa ggatgatgac cccccgccga ggagaaccaa gcgaaacaca gcctgacgcc    60
ctgtgtctgg agctg    75

<210> SEQ ID NO 114
<211> LENGTH: 83
<212> TYPE: DNA
<213> ORGANISM: Artificial Sequence
<220> FEATURE:
<223> OTHER INFORMATION: USH2A

<400> SEQUENCE: 114
tttcaactat tattattatt acccagttag aaagtgaata aatgacctaa atgggaaacc    60
tgacataggt agacatattg gct    83

<210> SEQ ID NO 115
<211> LENGTH: 97
<212> TYPE: DNA
<213> ORGANISM: Artificial Sequence
<220> FEATURE:
<223> OTHER INFORMATION: D13S1320

<400> SEQUENCE: 115
gtataaattc atacacatta tgtggttctg gtgtctgcca tctgcagcac ataagcaaat    60
tcccctaatt actgacatct ctctacgaag gcccata    97

<210> SEQ ID NO 116
<211> LENGTH: 99
<212> TYPE: DNA
<213> ORGANISM: Artificial Sequence
<220> FEATURE:
<223> OTHER INFORMATION: SEMA6D

<400> SEQUENCE: 116
ctctccctta tttaagaagg gatatcctgg ctcctcagcc tgccatctgg ggttctctac    60
attttcacat cttttccata actagccttt acactcttc    99

<210> SEQ ID NO 117
<211> LENGTH: 99
<212> TYPE: DNA
<213> ORGANISM: Artificial Sequence
<220> FEATURE:

<223> OTHER INFORMATION: MYO5C:-1

<400> SEQUENCE: 117 gttactttt gagaacattt aaaaataaat acattgaaat gctgattaga gagcgaaagt    60
aatttaggtt gcttttcaa tctgaggttt ttttaaaaa                          99

<210> SEQ ID NO 118
<211> LENGTH: 99
<212> TYPE: DNA
<213> ORGANISM: Artificial Sequence
<220> FEATURE:
<223> OTHER INFORMATION: MYO5C

<400> SEQUENCE: 118 gttactttt gagaaaattt aaaaataaat acattgaaat gctgattaga gagcgaaagt    60
aatttaggtt gcttttcaa tctgaggttt ttttaaaaa                          99

<210> SEQ ID NO 119
<211> LENGTH: 97
<212> TYPE: DNA
<213> ORGANISM: Artificial Sequence
<220> FEATURE:
<223> OTHER INFORMATION: TOM1L1

<400> SEQUENCE: 119
tccgacggcc ccactgcgtt tctcccttt aatgtttaat gcgatgatga ctattgctga    60
tcaggactaa attttacccct aggatgccca gggaata                          97

<210> SEQ ID NO 120
<211> LENGTH: 99
<212> TYPE: DNA
<213> ORGANISM: Artificial Sequence
<220> FEATURE:
<223> OTHER INFORMATION: HERC1

<400> SEQUENCE: 120
acttcttcca tgaagctttt catgttgtaa tcaccctacg ctcaccaaca cagatttaat    60
cacttcctcc tctaactctc ttactttgc ttacacaca                          99

<210> SEQ ID NO 121
<211> LENGTH: 96
<212> TYPE: DNA
<213> ORGANISM: Artificial Sequence
<220> FEATURE:
<223> OTHER INFORMATION: DRD2NCAM

<400> SEQUENCE: 121
gcccttgccc ctcgcttatc ttctcccaga tacataagac cacttattgc caattactgt    60
gctagaagaa agacagccaa cttatacgga gggcct                            96

<210> SEQ ID NO 122
<211> LENGTH: 96
<212> TYPE: DNA
<213> ORGANISM: Artificial Sequence
<220> FEATURE:
<223> OTHER INFORMATION: ELK2B

<400> SEQUENCE: 122
tgaaagttac aagtacaatt ttttaaacta gtaaagaag atgtaatcta ttcaatggaa    60
aacaggaaat gtggaagaaa caaacaaaaa ataact                            96

```
<210> SEQ ID NO 123
<211> LENGTH: 98
<212> TYPE: DNA
<213> ORGANISM: Artificial Sequence
<220> FEATURE:
<223> OTHER INFORMATION: CEBPB

<400> SEQUENCE: 123
ctggtgcaca acacatgcta gctattttca ttcttactag tggcatagta gaaagcactg      60 gaatttagc ttcagacaga cctgggtgta catttcag                               98

<210> SEQ ID NO 124
<211> LENGTH: 95
<212> TYPE: DNA
<213> ORGANISM: Artificial Sequence
<220> FEATURE:
<223> OTHER INFORMATION: FRMD3

<400> SEQUENCE: 124
gaatcatata tatctttgaa agtaaggaca gagaatgtaa atcaggcaat aaatgactga      60
agacaaatgg gcagggaccg agggatatag catgt                                 95

<210> SEQ ID NO 125
<211> LENGTH: 94
<212> TYPE: DNA
<213> ORGANISM: Artificial Sequence
<220> FEATURE:
<223> OTHER INFORMATION: LINC01233

<400> SEQUENCE: 125
aacattctct atcatgtggc ctggcacaag gattggcagc aacagagcag acagaaccaa      60
aggaagaagg gcctgaaaaa cctgctagtg catt                                  94

<210> SEQ ID NO 126
<211> LENGTH: 98
<212> TYPE: DNA
<213> ORGANISM: Artificial Sequence
<220> FEATURE:
<223> OTHER INFORMATION: STATP1

<400> SEQUENCE: 126
ataagcactg cactttacca agttgatgga tgcaggttct ttatttcagc cagtaacagg      60
taaaagttag aggttcaact attgtgtagg gaagttat                              98

<210> SEQ ID NO 127
<211> LENGTH: 99
<212> TYPE: DNA
<213> ORGANISM: Artificial Sequence
<220> FEATURE:
<223> OTHER INFORMATION: RBFOX1-1

<400> SEQUENCE: 127
tgttgcatgt gctaatagtt gattgtctta gattgctgag tagtattcta tggtgtcaat      60
ctaccaccca agaatctttt ttcagtagac accctgagg                             99

<210> SEQ ID NO 128
<211> LENGTH: 79
<212> TYPE: DNA
<213> ORGANISM: Artificial Sequence
<220> FEATURE:
<223> OTHER INFORMATION: NELFA
```

<400> SEQUENCE: 128
ggagcgatgc tttttcttac cacgaagcgt tgatataaag gaagatgctc atgttaagaa    60
acacagaaca cgcagcggc                                                 79

<210> SEQ ID NO 129
<211> LENGTH: 95
<212> TYPE: DNA
<213> ORGANISM: Artificial Sequence
<220> FEATURE:
<223> OTHER INFORMATION: ZC3H7B

<400> SEQUENCE: 129
ctttcattca ttccataagg aggcccacaa aacactctcg gccctgggcc tgagagagct    60
gcgtccttgc cctcagggac ctcccagcct gcaaa                                95

<210> SEQ ID NO 130
<211> LENGTH: 95
<212> TYPE: DNA
<213> ORGANISM: Artificial Sequence
<220> FEATURE:
<223> OTHER INFORMATION: EDAR

<400> SEQUENCE: 130
tatccaaaaa ggggtgaaag aatcactgag ttagagaagg cttcaggaga atccagagtt    60
caatctgggt cataagaaca tacaactcag atttc                                95

<210> SEQ ID NO 131
<211> LENGTH: 97
<212> TYPE: DNA
<213> ORGANISM: Artificial Sequence
<220> FEATURE:
<223> OTHER INFORMATION: KANK1

<400> SEQUENCE: 131
acattctagg gacagttaaa gtctcctgtg tacacggttg ccagaagaaa aaatactaag    60
cacgtgttca tcgtttatct aaaattcggt ttaatgg                              97

<210> SEQ ID NO 132
<211> LENGTH: 95
<212> TYPE: DNA
<213> ORGANISM: Artificial Sequence
<220> FEATURE:
<223> OTHER INFORMATION: RBFOX1

<400> SEQUENCE: 132
gtatttggaa ttaacgcagg agctagagac taagcaaacc ccgcctccac cccagtgcag    60
atttcagttg aatgcagact agagcctttg aaaat                                95

<210> SEQ ID NO 133
<211> LENGTH: 98
<212> TYPE: DNA
<213> ORGANISM: Artificial Sequence
<220> FEATURE:
<223> OTHER INFORMATION: PFKP

<400> SEQUENCE: 133
aaagtatgtt ttaagactct gaaaattttt gaactcactc ccagaaagtt ttaccacctc    60
ttcttctgtg tggccaccag ggggacgtag tgtggccg                             98

<210> SEQ ID NO 134

```
<211> LENGTH: 98
<212> TYPE: DNA
<213> ORGANISM: Artificial Sequence
<220> FEATURE:
<223> OTHER INFORMATION: LPPR1

<400> SEQUENCE: 134
gctctgaaca attgggtatt cttttttctt agagcccaga tgcattttt tgaaagtcgt    60 tccaggggcc tgagatgaag tgggggtgtg agaagtaa                            98

<210> SEQ ID NO 135
<211> LENGTH: 99
<212> TYPE: DNA
<213> ORGANISM: Artificial Sequence
<220> FEATURE:
<223> OTHER INFORMATION: CYYR1

<400> SEQUENCE: 135
gagagtgctc ttccctgaat ccctcacgtc atattgttag tgcctcttct gcttattcac    60
aagaccagtc atcgtagagg ttggatttga atcttgtat                           99

<210> SEQ ID NO 136
<211> LENGTH: 95
<212> TYPE: DNA
<213> ORGANISM: Artificial Sequence
<220> FEATURE:
<223> OTHER INFORMATION: HRH4

<400> SEQUENCE: 136
tcacatcatg acgtctactg ggcagtgaac tttagctaca tatgaatacc cagccagatt    60
ccaagattgt ggaaaccaag atggcagcct aggaa                               95

<210> SEQ ID NO 137
<211> LENGTH: 96
<212> TYPE: DNA
<213> ORGANISM: Artificial Sequence
<220> FEATURE:
<223> OTHER INFORMATION: LOC28716

<400> SEQUENCE: 137
gagcacgtcg cgttctggaa cctcattgtc tcacccttgt caaaccatgg gcagtgccat    60
ttactgtgca ggcttcagag gattaactga ggcagt                              96

<210> SEQ ID NO 138
<211> LENGTH: 102
<212> TYPE: DNA
<213> ORGANISM: Artificial Sequence
<220> FEATURE:
<223> OTHER INFORMATION: D12S290

<400> SEQUENCE: 138
gtacaaaatt ctattgttgg tcttaactca ctgctttcta tcgtttatgt tgctgtgttt    60
tctgttacta tgtaagtttc tttgaggcat gcaccatcta tt                      102

<210> SEQ ID NO 139
<211> LENGTH: 97
<212> TYPE: DNA
<213> ORGANISM: Artificial Sequence
<220> FEATURE:
<223> OTHER INFORMATION: TENM4
```

```
<400> SEQUENCE: 139
gtgctcgctt tgttgtgctt gtgtcggatg gtgagcgaac cctcagaaca caactgtaca    60
gcaggacttg gctcactgga ctctcattat ctggcca                            97

<210> SEQ ID NO 140
<211> LENGTH: 96
<212> TYPE: DNA
<213> ORGANISM: Artificial Sequence
<220> FEATURE:
<223> OTHER INFORMATION: CNTN5:-1

<400> SEQUENCE: 140
ttgggtaaca cagcaaagtg taaaaaaaaa atggaggggg attaattagt tggaaagaaa    60
agactggttt agacatatgg aaggttatta tcaaga                             96

<210> SEQ ID NO 141
<211> LENGTH: 96
<212> TYPE: DNA
<213> ORGANISM: Artificial Sequence
<220> FEATURE:
<223> OTHER INFORMATION: CNTN5:-2

<400> SEQUENCE: 141
ttgggtaaca cagcaaagtg taaaaaaaaa tggaggggga ttaattagtt ggaaagaaaa    60
gactggttta gacatatgga aggttattat caagag                             96

<210> SEQ ID NO 142
<211> LENGTH: 95
<212> TYPE: DNA
<213> ORGANISM: Artificial Sequence
<220> FEATURE:
<223> OTHER INFORMATION: CEP104

<400> SEQUENCE: 142
acggctgagg tgcagcaggc atgcagtgat acttgctgaa tggacagaag ccgttcccac    60
atggagcttc catgacatgc atttacacac cccga                              95

<210> SEQ ID NO 143
<211> LENGTH: 99
<212> TYPE: DNA
<213> ORGANISM: Artificial Sequence
<220> FEATURE:
<223> OTHER INFORMATION: COG2

<400> SEQUENCE: 143
tggtatgaag tacctattaa acgttatttc tgaatgctat atgtatttga tgtttatcca    60
aacacctggg agatagtgtc atgtaaaatt gtgcgtggc                          99

<210> SEQ ID NO 144
<211> LENGTH: 95
<212> TYPE: DNA
<213> ORGANISM: Artificial Sequence
<220> FEATURE:
<223> OTHER INFORMATION: ITGB6

<400> SEQUENCE: 144
accctctcta cctaaggatg ggcaatggct tatgagtgag aaacatggag ccgtgggaac    60
tcagaatgac atgctacctg gagattgtgg taacg                              95

<210> SEQ ID NO 145
```

```
<211> LENGTH: 96
<212> TYPE: DNA
<213> ORGANISM: Artificial Sequence
<220> FEATURE:
<223> OTHER INFORMATION: D18S1122

<400> SEQUENCE: 145
gaactggaga gcaggtggat taaatctggg gggtgactcc agcacatctc taatgaacac    60
ttcttaacat ttaatttcaa agggcctggt gaccct                              96

<210> SEQ ID NO 146
<211> LENGTH: 95
<212> TYPE: DNA
<213> ORGANISM: Artificial Sequence
<220> FEATURE:
<223> OTHER INFORMATION: GFI1B

<400> SEQUENCE: 146
cggggtctcc tcctggcttc ttcttgccgc cgcctgctct gggcagagcc cgggagtgtg    60
agccgccaga agcagcggca cgtggctgtc tctct                               95

<210> SEQ ID NO 147
<211> LENGTH: 96
<212> TYPE: DNA
<213> ORGANISM: Artificial Sequence
<220> FEATURE:
<223> OTHER INFORMATION: D21S1263

<400> SEQUENCE: 147
gacctatagg gtagggtttt caggagggct tagctgactt cagctgaaat gctcaggttg    60
gggcagggtg ttggaggtgt gagaaagcct tcagct                              96

<210> SEQ ID NO 148
<211> LENGTH: 96
<212> TYPE: DNA
<213> ORGANISM: Artificial Sequence
<220> FEATURE:
<223> OTHER INFORMATION: D5S1970

<400> SEQUENCE: 148
cttgattttc ttaacaaaac tgaaggccac agttgaagag agagagcatg agacagcttg    60
atcgaaatgg tgaagctttg gagagatttt gcgggg                              96

<210> SEQ ID NO 149
<211> LENGTH: 94
<212> TYPE: DNA
<213> ORGANISM: Artificial Sequence
<220> FEATURE:
<223> OTHER INFORMATION: LOC642852

<400> SEQUENCE: 149
gggcgagcag gggtcatgga tggggctcac tggggactgt gagaatctgt cccgcaggac    60
tttctgggat ggaaacgctg gcagaggtga agcc                                94

<210> SEQ ID NO 150
<211> LENGTH: 96
<212> TYPE: DNA
<213> ORGANISM: Artificial Sequence
<220> FEATURE:
<223> OTHER INFORMATION: COL4A1
```

<400> SEQUENCE: 150 gtttctgtt tcagctggct tttgcgggaa agggaagccc tggggctagg agagcagtcc    60
ttgccctgtg ggaagggtcc caggtggcac tgcccc    96

<210> SEQ ID NO 151
<211> LENGTH: 98
<212> TYPE: DNA
<213> ORGANISM: Artificial Sequence
<220> FEATURE:
<223> OTHER INFORMATION: IGSF21

<400> SEQUENCE: 151
ccagttctca tgaatctgag gaattcttcc tcctagctac ttccttcctt ttccctcatt    60
acatccctgc caaggacaaa ttctgccatt tgcatggc    98

<210> SEQ ID NO 152
<211> LENGTH: 94
<212> TYPE: DNA
<213> ORGANISM: Artificial Sequence
<220> FEATURE:
<223> OTHER INFORMATION: RXRA

<400> SEQUENCE: 152
gtcacgaatg cggctcagga ggcccaagtg tgcacagtga gctcacaccc acttccagcc    60
aacaaccctc ttgcctggtg aaacttccct gggc    94

<210> SEQ ID NO 153
<211> LENGTH: 95
<212> TYPE: DNA
<213> ORGANISM: Artificial Sequence
<220> FEATURE:
<223> OTHER INFORMATION: SGCG:1

<400> SEQUENCE: 153
cttcagttgt caaggtattg ggtacagggg tcagaaagaa acatgactcc atggaccact    60
gcttggccca agaccagatg tcaaaaccac agagc    95

<210> SEQ ID NO 154
<211> LENGTH: 96
<212> TYPE: DNA
<213> ORGANISM: Artificial Sequence
<220> FEATURE:
<223> OTHER INFORMATION: LINC0111

<400> SEQUENCE: 154
caacctttcc tgtgggctaa ggtaggaaag cagaaaacag ttagtgtgag attcttggtg    60
tcctcaagag cagcctgtgt aacagaaaag accgtt    96

<210> SEQ ID NO 155
<211> LENGTH: 97
<212> TYPE: DNA
<213> ORGANISM: Artificial Sequence
<220> FEATURE:
<223> OTHER INFORMATION: LRRN2

<400> SEQUENCE: 155
ttgccgaaga aaacacggaa gccgccagca ctattatgca ttcatgattc cagcttcaac    60
cagtcctctc tgctgcaatc cctttattcc tcctctg    97

<210> SEQ ID NO 156

```
<211> LENGTH: 103
<212> TYPE: DNA
<213> ORGANISM: Artificial Sequence
<220> FEATURE:
<223> OTHER INFORMATION: CPNE4:-1

<400> SEQUENCE: 156
acaaatagtc atcatcattc ctattttaca gatgggtaaa ttaagattca aagaatcttt      60
tttgttttct cgtttgtttt ttggttggtt ttgttttgct ttt                       103

<210> SEQ ID NO 157
<211> LENGTH: 103
<212> TYPE: DNA
<213> ORGANISM: Artificial Sequence
<220> FEATURE:
<223> OTHER INFORMATION: CPNE4

<400> SEQUENCE: 157
acaaatagtc atcatcattc ctattttaca gatgggtaaa ttaagattca aagaatcttt      60
tttgttttct cgtttgtttt ttggttggtt ttgttttgct ttt                       103

<210> SEQ ID NO 158
<211> LENGTH: 97
<212> TYPE: DNA
<213> ORGANISM: Artificial Sequence
<220> FEATURE:
<223> OTHER INFORMATION: COL4A3

<400> SEQUENCE: 158
taggtttctc atctattaga tggagcttat aacagtacct cccttacaga attgttgtaa      60
gatataatga gataatatga gacagccagc actgaaa                              97

<210> SEQ ID NO 159
<211> LENGTH: 97
<212> TYPE: DNA
<213> ORGANISM: Artificial Sequence
<220> FEATURE:
<223> OTHER INFORMATION: SUDS3

<400> SEQUENCE: 159
tcatttaaaa atctggtagc ctggtggaag ggaggtagca gaaccaatgc tgattgggac      60
aggagattat ttcacaaata attcataacc taggttt                              97

<210> SEQ ID NO 160
<211> LENGTH: 97
<212> TYPE: DNA
<213> ORGANISM: Artificial Sequence
<220> FEATURE:
<223> OTHER INFORMATION: D13S169

<400> SEQUENCE: 160
tttccaagtt gttctagtga attactgaac tggataggat tgtggaaacc tgtgaataat      60
agctaggtag tcagaagaca tggtgcgctg gggatcc                              97

<210> SEQ ID NO 161
<211> LENGTH: 97
<212> TYPE: DNA
<213> ORGANISM: Artificial Sequence
<220> FEATURE:
<223> OTHER INFORMATION: PLCG2
```

<400> SEQUENCE: 161
cttccagaga catttacata ctggcataac taccatacac aaacttctgg acacaaagtg    60
atcgcataaa tcacggggct ttgtgctttt gttgttg                            97

<210> SEQ ID NO 162
<211> LENGTH: 94
<212> TYPE: DNA
<213> ORGANISM: Artificial Sequence
<220> FEATURE:
<223> OTHER INFORMATION: D22S1159

<400> SEQUENCE: 162
ctcccggaaa cgtgattagt gaagacacat taacagcgaa actgacagag aacctcaaca    60
ttctctggta ggaaaagcca ggatcctggc agag                               94

<210> SEQ ID NO 163
<211> LENGTH: 98
<212> TYPE: DNA
<213> ORGANISM: Artificial Sequence
<220> FEATURE:
<223> OTHER INFORMATION: KIF16B

<400> SEQUENCE: 163
tttacttata tcacagaaca ccaaacccag attcctccca ttcccacagt gggtcctttt    60
ttctcaatca atcactaacc taatgcgtct agagctttt                          98

<210> SEQ ID NO 164
<211> LENGTH: 95
<212> TYPE: DNA
<213> ORGANISM: Artificial Sequence
<220> FEATURE:
<223> OTHER INFORMATION: ADH7

<400> SEQUENCE: 164
agagatgaag aaaaggggca gaagatgaac atgggggatc acaaagtgaa ggccttctgt    60
gtctcagagt tgcctaaaca ccctgcttcc atatc                              95

<210> SEQ ID NO 165
<211> LENGTH: 99
<212> TYPE: DNA
<213> ORGANISM: Artificial Sequence
<220> FEATURE:
<223> OTHER INFORMATION: C14ORF43

<400> SEQUENCE: 165
tgttcttaag cgactggaat gccctcttta gctgggggtg ttcggcctcc ttttttggag    60
gtgggttgtg atgtcaaaac actgggttgt ggtatagga                          99

<210> SEQ ID NO 166
<211> LENGTH: 96
<212> TYPE: DNA
<213> ORGANISM: Artificial Sequence
<220> FEATURE:
<223> OTHER INFORMATION: FAM99A

<400> SEQUENCE: 166
aagacctcgt tccattgccc taggtcaggc atggattatt aactctcagg gttttggggg    60
accagcagcc acagatgtgg agtcctgggg aaaggg                             96

<210> SEQ ID NO 167

```
<211> LENGTH: 96
<212> TYPE: DNA
<213> ORGANISM: Artificial Sequence
<220> FEATURE:
<223> OTHER INFORMATION: FRMD4A

<400> SEQUENCE: 167
aaataatcat ttgctttttc aacagaagta aagtcactga acatttttgg aatctaaagt    60
tccaaatgga agtcagggat agcagatgaa cccaaa                              96

<210> SEQ ID NO 168
<211> LENGTH: 100
<212> TYPE: DNA
<213> ORGANISM: Artificial Sequence
<220> FEATURE:
<223> OTHER INFORMATION: OR52S1P

<400> SEQUENCE: 168
aaattatttg tcatcatctc cttagaagcc aaagctccct aatagctctc tcttccagat    60
tcaaggttac cattttttcat gccttattgt tttttcaaac                         100

<210> SEQ ID NO 169
<211> LENGTH: 94
<212> TYPE: DNA
<213> ORGANISM: Artificial Sequence
<220> FEATURE:
<223> OTHER INFORMATION: ARHGAP27

<400> SEQUENCE: 169
gcagcccaca ctgaaggctg ggtcagtcct gtttccacag tggggaagtg atcagagctg    60
cctcatgact ggcacagtgc cagcacaggg ccag                                94

<210> SEQ ID NO 170
<211> LENGTH: 97
<212> TYPE: DNA
<213> ORGANISM: Artificial Sequence
<220> FEATURE:
<223> OTHER INFORMATION: LRRC63

<400> SEQUENCE: 170
gccagctaca gacagtttca caaagtcatt atctaattgg aaatatctgc tgggacacca    60
gatttcccac tgacattaac tgggcattct cttagcc                             97

<210> SEQ ID NO 171
<211> LENGTH: 83
<212> TYPE: DNA
<213> ORGANISM: Artificial Sequence
<220> FEATURE:
<223> OTHER INFORMATION: USH2A

<400> SEQUENCE: 171
tttcaactat tattattatt acccagttag aaagtgaata aatgacctaa atgagaaacc    60
tgacataggt agacatattg gct                                            83

<210> SEQ ID NO 172
<211> LENGTH: 97
<212> TYPE: DNA
<213> ORGANISM: Artificial Sequence
<220> FEATURE:
<223> OTHER INFORMATION: D13S1320
```

<400> SEQUENCE: 172
atataaattc atacacatta tgtggttctg gtgtctgcca tctgcagcac ataagcaact    60
tcccctaatt actgacatct ctctacgaag gcccatg    97

<210> SEQ ID NO 173
<211> LENGTH: 99
<212> TYPE: DNA
<213> ORGANISM: Artificial Sequence
<220> FEATURE:
<223> OTHER INFORMATION: SEMA6D

<400> SEQUENCE: 173
ctctcccgta tttaagaagg gatatcctgg ctcctcagcc tgccatctgg ggttctctac    60
attttcacat cttttccata actagccttt acactcttc    99

<210> SEQ ID NO 174
<211> LENGTH: 98
<212> TYPE: DNA
<213> ORGANISM: Artificial Sequence
<220> FEATURE:
<223> OTHER INFORMATION: TOM1L1

<400> SEQUENCE: 174
tccgacggcc ccattgcgtt tctcccctttt aatgtttaat gcgatgatga ctattgctga    60
tcaggactaa attttaccct aggatgccca gggaataa    98

<210> SEQ ID NO 175
<211> LENGTH: 99
<212> TYPE: DNA
<213> ORGANISM: Artificial Sequence
<220> FEATURE:
<223> OTHER INFORMATION: HERC1

<400> SEQUENCE: 175
acctcttcca tgaagctttt catgttgtaa tcaccctacg ctcaccaaca cagatttaat    60
cacttcctcc tctaactctc ttacttttgc ttacacaca    99

<210> SEQ ID NO 176
<211> LENGTH: 98
<212> TYPE: DNA
<213> ORGANISM: Artificial Sequence
<220> FEATURE:
<223> OTHER INFORMATION: CEBPB

<400> SEQUENCE: 176
ctggtgcaca atacatgcta gctatttca ttcttactag tggcatagta gaaagcactg    60
gaattttagc ttcagacaga cctgggtgta catttcag    98

<210> SEQ ID NO 177
<211> LENGTH: 95
<212> TYPE: DNA
<213> ORGANISM: Artificial Sequence
<220> FEATURE:
<223> OTHER INFORMATION: FRMD3

<400> SEQUENCE: 177
gaatcatata tatctttgaa aataaggaca gagagtgtaa atcaggcaat aaatgactga    60
agacaaatgg gcagggaccg agggatatag cattt    95

<210> SEQ ID NO 178

```
<211> LENGTH: 99
<212> TYPE: DNA
<213> ORGANISM: Artificial Sequence
<220> FEATURE:
<223> OTHER INFORMATION: RBFOX1-1

<400> SEQUENCE: 178
tgttgcgtgt gctaatagtt gattgtctta gattgctgag tagtattcta tggtgtcaat      60
ctaccaccca agaatctttt ttcagtagac accctgagg                             99

<210> SEQ ID NO 179
<211> LENGTH: 79
<212> TYPE: DNA
<213> ORGANISM: Artificial Sequence
<220> FEATURE:
<223> OTHER INFORMATION: NELFA

<400> SEQUENCE: 179
ggagcgatgc tttttcttac cacgaagcat tgatataaag gaagatgctc atgttaagaa      60
acacagaaca cgcagcggc                                                   79

<210> SEQ ID NO 180
<211> LENGTH: 99
<212> TYPE: DNA
<213> ORGANISM: Artificial Sequence
<220> FEATURE:
<223> OTHER INFORMATION: CYYR1

<400> SEQUENCE: 180
gaaagtgctc ttccctgaat ccctcacgtc atattgttag tgcctcttct gcttattcac      60
aagaccagtc atcgtagagg ttggatttga atcttgtat                             99

<210> SEQ ID NO 181
<211> LENGTH: 102
<212> TYPE: DNA
<213> ORGANISM: Artificial Sequence
<220> FEATURE:
<223> OTHER INFORMATION: D12S290

<400> SEQUENCE: 181
gtacaaactt ctattgttgg tcttaactca ctgctttcta tcgtttatgt tgctgtgttt      60
tctgttacta tgtaagtttc tttgaggcat gcaccatcta tt                        102

<210> SEQ ID NO 182
<211> LENGTH: 97
<212> TYPE: DNA
<213> ORGANISM: Artificial Sequence
<220> FEATURE:
<223> OTHER INFORMATION: TENM4

<400> SEQUENCE: 182 gtgctcccctt tgttgtgctt gtgtcggatg gtgagcgaac cctcagaaca caactctaca    60
gcaggacttg gctcactgga ctctcattat ctggcca                               97

<210> SEQ ID NO 183
<211> LENGTH: 95
<212> TYPE: DNA
<213> ORGANISM: Artificial Sequence
<220> FEATURE:
<223> OTHER INFORMATION: CEP104
```

<400> SEQUENCE: 183
acggctgagg tgcagcaggc gtgcagtgat acttgctgaa tggacagaag ccgttcccac    60
atggagcttc catgacatgc atttacacac cccga                              95

<210> SEQ ID NO 184
<211> LENGTH: 95
<212> TYPE: DNA
<213> ORGANISM: Artificial Sequence
<220> FEATURE:
<223> OTHER INFORMATION: ITGB6

<400> SEQUENCE: 184
accctcacta cctaaggatg ggcaatggct catgagtgag aaacatggag ccgtgggaac    60
tcagaatgac atgctacctg gagattgtgg taacg                              95

<210> SEQ ID NO 185
<211> LENGTH: 95
<212> TYPE: DNA
<213> ORGANISM: Artificial Sequence
<220> FEATURE:
<223> OTHER INFORMATION: GFI1B

<400> SEQUENCE: 185
cggggtctcc tcctggcctc ttcttgccgc cgcctgctct gggcagagcc cgggagtgtg    60
agccgccaga agcagcggca cgtggctgtc tctct                              95

<210> SEQ ID NO 186
<211> LENGTH: 96
<212> TYPE: DNA
<213> ORGANISM: Artificial Sequence
<220> FEATURE:
<223> OTHER INFORMATION: D21S1263

<400> SEQUENCE: 186
gacctatagg gtagggtttt caggagggct tagctgactt cagctgaaat gctcaggttg    60
gggcagggtg ttggaggtgt gcgaaagcct tcagct                             96

<210> SEQ ID NO 187
<211> LENGTH: 98
<212> TYPE: DNA
<213> ORGANISM: Artificial Sequence
<220> FEATURE:
<223> OTHER INFORMATION: IGSF21

<400> SEQUENCE: 187
ccagttctca tgaatctgag gaattcttcc tcctagctac ttccctcctt ttccctcatt    60
acatccctgc caaggacaaa ttctgccatt tgcatggc                           98

<210> SEQ ID NO 188
<211> LENGTH: 96
<212> TYPE: DNA
<213> ORGANISM: Artificial Sequence
<220> FEATURE:
<223> OTHER INFORMATION: GNGT2

<400> SEQUENCE: 188
gacccgctgg aggagcaaaa gttaagggac caatatggtc aatgggaggt cctcttattc    60
tcctgtctct aggatgacag gcttggtggt gggagg                             96

<210> SEQ ID NO 189

```
<211> LENGTH: 97
<212> TYPE: DNA
<213> ORGANISM: Artificial Sequence
<220> FEATURE:
<223> OTHER INFORMATION: COL4A3

<400> SEQUENCE: 189
taggtttctc atctagtaga tggagcttat aatagtacct cccttacaga attgttgtaa      60
gatataatga gataatatga gacagccagc actgaaa                              97

<210> SEQ ID NO 190
<211> LENGTH: 97
<212> TYPE: DNA
<213> ORGANISM: Artificial Sequence
<220> FEATURE:
<223> OTHER INFORMATION: PLCG2

<400> SEQUENCE: 190
cttccagaga catttacatg ctggcataac taacatacac aaacttctgg acacaaagtg      60
atcgcataaa tcacggggct ttgtgctttt gttgttg                              97

<210> SEQ ID NO 191
<211> LENGTH: 96
<212> TYPE: DNA
<213> ORGANISM: Artificial Sequence
<220> FEATURE:
<223> OTHER INFORMATION: FAM99A

<400> SEQUENCE: 191
gagacctcgt tccattgccc taggtcaggc atggattatt aactctcagg gttttggggg      60
accagcagcc acagatgtgg agtcctgggg aaaggg                               96

<210> SEQ ID NO 192
<211> LENGTH: 96
<212> TYPE: DNA
<213> ORGANISM: Artificial Sequence
<220> FEATURE:
<223> OTHER INFORMATION: FRMD4A

<400> SEQUENCE: 192
aaataatcat ttgcttttc aacaaaagta aagtcactga aacattttgg aatctaaagt       60
tccaaatgga agtcagggat agcagatgaa cccaaa                               96
```